(12) United States Patent
Peacock, III et al.

(10) Patent No.: US 10,646,135 B2
(45) Date of Patent: *May 12, 2020

(54) MAGNETIC RESONANCE SPECTROSCOPY PULSE SEQUENCE, ACQUISITION, AND PROCESSING SYSTEM AND METHOD

(71) Applicant: NOCIMED, INC., Redwood City, CA (US)

(72) Inventors: James Clayton Peacock, III, San Carlos, CA (US); John Patrick Claude, Redwood City, CA (US); Paul Henry Kane, Albuquerque, NM (US); Ricardo Dario Pradenas, Irvine, CA (US)

(73) Assignee: NOCIMED, INC., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/100,788

(22) Filed: Aug. 10, 2018

(65) Prior Publication Data

US 2019/0175051 A1    Jun. 13, 2019

Related U.S. Application Data

(63) Continuation of application No. 15/160,423, filed on May 20, 2016, now Pat. No. 10,045,711, which is a (Continued)

(51) Int. Cl.
*A61B 5/055* (2006.01)
*A61B 5/00* (2006.01)
(Continued)

(52) U.S. Cl.
CPC ............ *A61B 5/055* (2013.01); *A61B 5/0075* (2013.01); *A61B 5/4566* (2013.01);
(Continued)

(58) Field of Classification Search
CPC ..... A61B 5/055; A61B 5/4824; A61B 5/4566; A61B 5/0075
(Continued)

(56) References Cited

U.S. PATENT DOCUMENTS 4,983,920 A    1/1991   Lampman et al.
5,068,098 A   11/1991   Schweighardt et al.
(Continued)

FOREIGN PATENT DOCUMENTS

JP    S63-204143    8/1988
JP    H05-509162   12/1993
(Continued)

OTHER PUBLICATIONS

U.S. Appl. No. 16/376,879 Including its prosecution history, filed Apr. 5, 2019, Peacock, III et al.
(Continued)

*Primary Examiner* — Yosef Kassa
(74) *Attorney, Agent, or Firm* — Knobbe, Martens, Olson & Bear, LLP

(57) ABSTRACT

Systems and methods are provided for processing a set of multiple serially acquired magnetic resonance spectroscopy (MRS) free induction decay (FID) frames from a multi-frame MRS acquisition series from a region of interest (ROI) in a subject, and for providing a post-processed MRS spectrum. Processing parameters are dynamically varied while measuring results to determine the optimal post-processed results. Spectral regions opposite water from chemical regions of interest are evaluated and used in at least one processing operation. Frequency shift error is estimated via spectral correlation between free induction decay (FID) frames and a reference spectrum. Multiple groups of FID frames within the acquired set are identified to different phases corresponding with a phase step cycle of the acqui-
(Continued)

sition. Baseline correction is also performed via rank order filter (ROF) estimate and a polynomial fit. Sections of the ROF may be excluded from the polynomial fit, such as for example sections determined to be associated with relevant spectral peaks.

20 Claims, 63 Drawing Sheets

Related U.S. Application Data continuation of application No. 14/625,918, filed on Feb. 19, 2015, now Pat. No. 9,345,421, which is a continuation of application No. 13/843,117, filed on Mar. 15, 2013, now Pat. No. 8,965,094.

(60) Provisional application No. 61/624,284, filed on Apr. 14, 2012.

(51) Int. Cl.
  *G01R 33/483* (2006.01)
  *G01R 33/46* (2006.01)
  *G01R 33/48* (2006.01)
  *G01R 33/56* (2006.01)
  *G06T 7/00* (2017.01)

(52) U.S. Cl.
  CPC .......... *A61B 5/4824* (2013.01); *A61B 5/7257* (2013.01); *G01R 33/4625* (2013.01); *G01R 33/483* (2013.01); *G01R 33/4828* (2013.01); *G01R 33/5608* (2013.01); *G06T 7/0012* (2013.01); *Y10S 128/922* (2013.01); *Y10S 128/923* (2013.01)

(58) Field of Classification Search
  USPC ....... 382/128, 130, 131, 132, 209, 260, 278, 382/282, 312; 128/922, 923
  See application file for complete search history.

(56) References Cited

U.S. PATENT DOCUMENTS

| | | | |
|---|---|---|---|
| 5,190,039 A | 3/1993 | Takeuchi | |
| 5,201,311 A | 4/1993 | Bottomley et al. | |
| 5,207,715 A | 5/1993 | Fossel | |
| 5,270,651 A | 12/1993 | Wehrli | |
| 5,617,861 A | 4/1997 | Ross et al. | |
| 5,844,097 A | 12/1998 | Cameron, Sr. et al. | |
| 5,903,149 A | 5/1999 | Gonen et al. | |
| 6,018,675 A | 1/2000 | Apkarian et al. | |
| 6,069,478 A | 5/2000 | Hurd | |
| 6,278,891 B1 | 8/2001 | Reiderman et al. | |
| 6,418,335 B2 | 7/2002 | Avrin | |
| 6,472,871 B2 | 10/2002 | Ryner | |
| 6,552,541 B2 | 4/2003 | Nauerth | |
| 6,617,169 B2 | 9/2003 | Ke et al. | |
| 6,639,405 B2 | 10/2003 | Liu et al. | |
| 6,674,282 B2 | 1/2004 | Pines et al. | |
| 6,683,455 B2 | 1/2004 | Ebbels et al. | |
| 6,686,348 B2 | 2/2004 | De Nanteuil et al. | |
| 6,795,567 B1 | 9/2004 | Cham et al. | |
| 6,835,572 B1 | 12/2004 | Mountford et al. | |
| 6,836,114 B2 | 12/2004 | Reddy et al. | |
| 6,943,033 B2 | 9/2005 | Van Zijl et al. | |
| 6,987,997 B1 | 1/2006 | Hurd et al. | |
| 7,027,054 B1 | 4/2006 | Cheiky et al. | |
| 7,042,214 B2 | 5/2006 | Cunningham et al. | |
| 7,116,104 B2 | 10/2006 | Reddy et al. | |
| 7,123,009 B1 | 10/2006 | Scott | |
| 7,181,348 B2 | 2/2007 | Wishart et al. | |
| 7,184,813 B1 | 2/2007 | Hurd et al. | |
| 7,288,521 B2 | 10/2007 | Franco | |
| 7,319,784 B2 | 1/2008 | Ryner et al. | |
| 7,323,871 B2 | 1/2008 | Foo | |
| 7,411,396 B1 * | 8/2008 | Schirmer | G01R 33/485 324/307 |
| 7,499,745 B2 | 3/2009 | Littrup et al. | |
| 7,514,074 B2 * | 4/2009 | Pittenger | C12N 5/0657 424/93.1 |
| 7,676,254 B2 * | 3/2010 | Siddall | A61B 5/055 600/410 |
| 7,705,596 B2 | 4/2010 | Witschey et al. | |
| 7,741,844 B2 | 6/2010 | Hancu et al. | |
| 7,749,275 B2 | 7/2010 | Lambrecht et al. | |
| 7,940,264 B2 | 5/2011 | Jojic et al. | |
| 8,018,570 B2 | 9/2011 | Kameyama | |
| 8,076,936 B2 | 12/2011 | Borthakur et al. | |
| 8,208,709 B2 | 6/2012 | Ding et al. | |
| 8,263,043 B2 * | 9/2012 | Ahrens | A61B 5/411 424/9.34 |
| 8,344,728 B2 * | 1/2013 | Majumdar | A61B 5/055 324/309 |
| 8,478,380 B2 | 7/2013 | Soher | |
| 8,553,037 B2 | 10/2013 | Smith et al. | |
| 8,569,485 B2 * | 10/2013 | Yamakawa | C07D 251/24 544/180 |
| 8,609,334 B2 | 12/2013 | Buser et al. | |
| 8,615,285 B2 | 12/2013 | Ehman | |
| 8,668,647 B2 | 3/2014 | Eskandari | |
| 8,690,057 B2 | 4/2014 | Schoening et al. | |
| 8,761,860 B2 | 6/2014 | Peacock, III et al. | |
| 8,798,351 B2 | 8/2014 | Ding et al. | |
| 8,825,131 B2 | 9/2014 | Peacock, III et al. | |
| 8,838,201 B2 * | 9/2014 | Mori | A61B 5/055 600/410 |
| 8,965,094 B2 | 2/2015 | Peacock, III et al. | |
| 9,161,735 B2 | 10/2015 | Bradford et al. | |
| 9,280,718 B2 | 3/2016 | Claude et al. | |
| 9,345,421 B2 | 5/2016 | Peacock, III et al. | |
| 9,392,959 B2 | 7/2016 | Peacock, III et al. | |
| 9,724,013 B2 | 8/2017 | Peacock, III et al. | |
| 9,808,177 B2 | 11/2017 | Claude et al. | |
| 9,901,285 B2 | 2/2018 | Majumdar et al. | |
| 10,045,711 B2 | 8/2018 | Peacock, III et al. | |
| 10,123,759 B2 | 11/2018 | Bradford et al. | |
| 10,251,578 B2 | 4/2019 | Peacock, III et al. | |
| 10,285,622 B2 | 5/2019 | Peacock, III et al. | |
| 2001/0003423 A1 | 6/2001 | Wald | |
| 2002/0037251 A1 | 3/2002 | Driehuys | |
| 2004/0006376 A1 | 1/2004 | Falci | |
| 2004/0214348 A1 | 10/2004 | Nicholson et al. | |
| 2005/0024051 A1 | 3/2005 | Doddrell et al. | |
| 2005/0054910 A1 | 3/2005 | Tremblay et al. | |
| 2005/0240104 A1 | 10/2005 | Shim et al. | |
| 2005/0251025 A1 | 11/2005 | Hancu et al. | |
| 2007/0167729 A1 | 7/2007 | Mistretta et al. | |
| 2007/0249928 A1 | 10/2007 | Blezek et al. | |
| 2007/0253910 A1 | 11/2007 | Ahrens et al. | |
| 2008/0220530 A1 | 9/2008 | Bahn et al. | |
| 2008/0226148 A1 | 9/2008 | Gu et al. | |
| 2009/0076481 A1 | 3/2009 | Stegmann et al. | |
| 2009/0134869 A1 | 5/2009 | Lee | |
| 2009/0191131 A1 | 7/2009 | Fossheim et al. | |
| 2009/0232378 A1 | 9/2009 | Nakamura | |
| 2009/0261823 A1 | 10/2009 | Yu et al. | |
| 2010/0086185 A1 | 4/2010 | Weiss | |
| 2010/0121210 A1 | 5/2010 | Lindner | |
| 2010/0136588 A1 | 6/2010 | Colgin | |
| 2010/0166278 A1 | 7/2010 | Witschey | |
| 2010/0244834 A1 | 9/2010 | Mori et al. | |
| 2010/0264920 A1 | 10/2010 | Witschey et al. | |
| 2010/0268225 A1 | 10/2010 | Coe et al. | |
| 2011/0230755 A1 | 9/2011 | MacFarlane et al. | |
| 2011/0286630 A1 | 11/2011 | Harder | |
| 2012/0155731 A1 | 6/2012 | Weersink et al. | |
| 2014/0119631 A1 | 5/2014 | Mostafavi | |
| 2014/0194364 A1 | 7/2014 | Buser et al. | |
| 2015/0119688 A1 | 4/2015 | Peacock, III et al. | |
| 2017/0035844 A1 | 2/2017 | Buser et al. | |
| 2017/0105650 A1 | 4/2017 | Peacock, III et al. | |

(56) References Cited

U.S. PATENT DOCUMENTS

| | | | |
|---|---|---|---|
| 2018/0192910 | A1 | 7/2018 | Claude et al. |
| 2018/0317802 | A1 | 11/2018 | Majumdar et al. |
| 2019/0216418 | A1 | 7/2019 | Bradford et al. |

FOREIGN PATENT DOCUMENTS

| | | |
|---|---|---|
| JP | H06-503418 | 4/1994 |
| JP | 2003524490 | 8/2003 |
| JP | 2004526130 | 8/2004 |
| JP | 2004528559 | 9/2004 |
| KR | 10-2011-0100046 | 9/2011 |
| WO | WO 2006-081471 | 8/2006 |
| WO | WO 2007-035906 | 3/2007 |
| WO | WO 2009-058915 | 5/2009 |
| WO | WO 2009-148550 | 12/2009 |
| WO | WO 2011-047197 | 4/2011 |
| WO | WO 2011-060237 | 5/2011 |
| WO | WO 2011-146798 | 11/2011 |
| WO | WO 2012-071566 | 5/2012 |

OTHER PUBLICATIONS

U.S. Appl. No. 16/408,188 Including its prosecution history, filed May 9, 2019, Peacock, III et al.
U.S. Appl. No. 16/224,590 Including its prosecution history, filed Dec. 18, 2018, Lotz et al.
Bartels, E.M., J.C. Fairbank, et al. (1998) "Oxygen and lactate concentrations measured in vivo in the intervertebral discs of patients with scoliosis and back pain." Spine 23 (1): 1-7; discussion 8.
Bottomley PA. "Spatial localization in NMR spectroscopy in vivo." Ann N Y Acad Sci 1987; 508:333-348.
Brown TR, Kincaid BM, Ugurbil K. "NMR chemical shift imaging in three dimensions." Proc. Natl. Acad. Sci. USA 1982; 79:3523-3526.
Brown, M.F., M.V. Hukkanen, et al. (1997). "Sensory and sympathetic innervation of the vertebral endplate in patients with degenerative disc disease." J Bone Joint Surg Br 79(1): 147-53.
Buenaventura, R.M., R.V. Shah, et al. (2007). "Systematic review of discography as a diagnostic test for spinal pain: an update." Pain Physician 10(1): 147-64.
Carragee et al., "2009 ISSLS Prize Winner: Does Discography Cause Accelerated Progression of Degeneration Changes in the Lumbar Disc," SPINE vol. 34, No. 21, pp. 2338-2345, 2009.
Carragee, E. J., T. Lincoln, et al. (2006). "A gold standard evaluation of the "discogenic pain" diagnosis and determined by provocative discography." Spine 31(18): 2115-23.
Carragee, E.J. and T.F. Alamin (2001). "Discography, a review." Spine J 1(5): 364-72.
Carragee, E.J., T.F. Alamin. et al. (2006). "Low-pressure positive Discography in subjects asymptomatic of significant low back pain illness." Spine 31(5): 505-9.
Cohen, S.P., T.M. Larkin, et al. (2005). "Lumbar discography: a comprehensive review of outcome studies, diagnostic accuracy, and principles." Reg Anesth Pain Med 30(2): 163-83.
Coppes, M.H., E. Marani, et al. (1997). "Innervation of "painful" lumbar discs." Spine 22(20): 2342-49.
Cunningham CH, Vigneron DB, Chen AP, Xu D, Hurd RE, Sailasuta N, Pauly JM. "Design of symmetric-sweep spectral-spatial RF pulses for spectral editing." Magn Reson Med 2004; 52: 147-153.
Derby, R., R.M. Baker, et al. (2008). "Analgesic Discography: Can Analgesic Testing Identify a Painful Disc?" SpineLine (November-December): 17-24.
Diamant, B., J. Karlsson, et al. (1968). "Correlation between lactate levels and pH in discs of patients with lumbar rhizopathies." Experientia 24(12): 1195-6.
Jiru, F., "Introduction to Post-Processing Techniques," Europeant Journal of Radiology 67, (2008) 202-217.
Frahm J, Bruhn H, Gyngell ML, Merboldt KD, Hanicke W, Sauter R. "Localized high-resolution proton NMR spectroscopy using stimulated echoes: initial applications to human brain in vivo." Magn Reson Med 1989; 9:79-93.
Freemont, A.J., A. Watkins, et al. (2002). "Nerve growth factor expression and innervation of the painful intervertebral disc." J Pathol 197(3): 286-92.
Freemont, A.J., T.E. Peacock, et al. (1997). "Nerve ingrowth into diseased intervertebral disc in chronic back pain." Lancet 350(9072): 178-81.
Grunhagen, T., G. Wilde, et al. (2006). "Nutrient supply and intervertebral disc metabolism." J Bone Joint Surg Am 88 Suppl 2: 30-5.
Guyer, R.D. and D.D. Ohnmeiss (2003). "Lumbar discography." Spine J 3(3 Suppl): 11S-27S.
Immke, D. C. and E.W. McCleskey (2001). "Lactate enhances the acid-sensing Na+ channel on ischemia-sensing neurons." Nat Neurosci 4(9): 869-70.
Ishihara, H. and J.P. Urban (1999). "Effects of low oxygen concentrations and metabolic inhibitors on proteoglycan and protein synthesis rates in the intervertebral disc." J Orthop Res 17(6): 829-35.
Jain, A., S.M Brady-Kalnay, et al. (2004). "Modulation of Rho GTPase activity alleviates chondroitin sulfate proteoglycan-dependent inhibition of neurite extension." J Neurosci Res 77(2): 299-307.
Jones, L.L., D. Sajed, et al. (2003). "Axonal regeneration through regions of chondroitin sulfate proteoglycan deposition after spinal cord injury: a balance of permissiveness and inhibition." J Neurosci 23(28): 9276-88.
Keshari, K. R., A. S. Zektzer, et al. (2005). "Characterization of intervertebral disc degeneration by high-resolution magic angle spinning (HR-MAS) spectroscopy." Magn Reson Med 53(3): 519-27.
Keshari, K.R., J.C. Lotz, et al. (Dec. 1, 2005). "Correlation of HR-MAS spectroscopy derived metabolite concentrations with collagen and proteoglycan levels and Thompson grade in the degenerative disc." Spine 30(23): 2683-88.
Keshari, K.R., J.C. Lotz, et al. (2008). "Lactic acid and proteoglycans as metabolic markers for discogenic back pain." Spine 33(3): 312-317.
Klapka, N. and H. W. Muller (2006). "Collagen matrix in spinal cord injury." J Neurotrauma 23(3-4): 422-35.
Molliver, D. C., D. C. Immke, et al. (2005). "ASIC3, an acid-sensing ion channel, is expressed in metaboreceptive sensory neurons." Mol Pain 1: 35.
Nachemson, A. (1969). "Intradiscal measurements of pH in patients with lumbar rhizopathies." Acta Orthop Scand 40(1): 23-42.
Naves, L. A. and E. W. McCleskey (2005). "An acid-sensing ion channel that detects ischemic pain." Braz J Med Biol Res 38(11): 1561-9.
O'Neill, C. and M. Kurgansky (2004). "Subgroups of positive discs on discography." Spine 29(19): 2134-9.
Pauly J, Le Roux P, Nishimura D, Macovski A. "Parameter relations for the Shinnar-Le Roux selective excitation pulse design algorithm [NMR imaging]." IEEE Trans Med Imaging 1991; 10: 53-65.
Properzi, F., R. A. Asher, et al. (2003). "Chondroitin sulphate proteoglycans in the central nervous system: changes and synthesis after injury." Biochem Soc Trans 31(2): 335-6.
Roberts, S., H. Evans, et al. (2006). "Histology and pathology of the human intervertebral disc." J Bone Joint Surg Am 88 Suppl 2: 10-14.
Roughley, P. J., M. Alini, et al. (2002). "The role of proteoglycans in aging, degeneration and repair of the intervertebral disc." Biochem Soc Trans 30(Pt 6): 869-74.
Rukwied, R., B. A. Chizh, et al. (2007). "Potentiation of nociceptive responses to low pH injections in humans by prostaglandin E2." J Pain 8(5): 443-51.
Scuderi, G. J., G. V. Brusovanik, et al. (2008). "A critical evaluation of discography in patients with lumbar intervertebral disc disease." Spine J 8(4): 624-9.

(56) References Cited

OTHER PUBLICATIONS

Star-Lack J, Nelson SJ, Kurhanewicz J, Huang LR, Vigneron DB. "Improved water and lipid suppression for 3D PRESS CSI using RF bank selective inversion with gradient dephasing (BASING)." Magn Reson Med 1997; 38: 311-321.
Sutherland, S. P., C. J. Benson, et al. (2001). "Acid-sensing ion channel 3 matches the acid-gated current in cardiac ischemia-sensing neurons." Proc Natl Acad Sci U S A 98(2): 711-6.
Urban, J. P., S. Smith, et al. (2004). "Nutrition of the intervertebral disc." Spine 29(23): 2700-9.
Wichman, H. J. (2007). "Discography: over 50 years of controversy." Wmj 106(1): 27-9.
Wolfer, L. R., R. Derby, et al. (2008). "Systematic review of lumbar provocation discography in asymptomatic subjects with a meta-analysis of false-positive rates." Pain Physician 11(4): 513-38.
Mari Garseth et al. "Metabolic changes in the cerebrospinal fluid of patients with lumbar disc herniation or spinal stenois." Journal of Neuroscience Research, vol. 69, No. 5, Sep. 1, 2002, pp. 692-695.
Henning A. et al. "Spinal cord MRS in and beyond the cerival spine", Proceedings of the International Society for Magnetic Resonance in Medicine, May 6, 2006, p. 889.
Zuo, J., D. Neubauer, et al. (1998). "Degradation of chondroitin sulfate proteoglycan enhances the neurite-promoting potential of spinal cord tissue." Exp Neurol 154(2): 654-62.
Zuo, J., Y. J. Hernandez, et al. (1998). "Chondroitin sulfate proteoglycan with neurite-inhibiting activity is up-regulated following peripheral nerve injury." J Neurobiol 34(1): 41-54.
Zuo, J., et al. "MR Spectroscopy in intervertebral disc and correlation with biochemical analysis." Proceedings of the International Society for Magnetic Resonance in Medicine, Apr. 18, 2009, p. 2002.
Zuo, J. et al. "Quantification of relaxation times of metabolite resonance in intervertebral disc using MR Spectroscopy", Proceedings of the International Society for Magnetic Resonance in Medicine, Apr. 18, 2009, p. 2001.
Haro, H. et al. "Matrix metalloproteinase-7-dependent release of tumor necrosis factor in a model of herniated disc resorption," Jour. of Clinical Inv., vol. 105, No. 2, Jan. 2000, pp. 143-150.
Mow, V.C. et al. "Basic Orthopaedic Biomechanics—Chapter 10—Bomechanics of the Human Spine," 1997, pp. 353-393.
Thompson, J. et al. "Preliminary Evaluation of a Scheme for Grading the Gross Morphology of the Human Intervertebral Disc," Spine, vol. 15, 1990, pp. 411-415.
Iatridis, J. et al. "Alterations in the Mechanical Behavior of the Human Lumbar Nucleas Pulposus with Degeneration and Aging," Jour. of Ortho Research, vol. 15, 1997, pp. 318-322.
Beall, et al. "NMR Data Handbook for Biomedical Applications," New York, Pergamon Press, 1984, 11 pages.
Boos, N. et al.—Quantitative Magnetic Resonance Imaging of the Lumbar Spine, Spine, vol. 20, No. 21, pp. 2358-2366.
Bottomley, P. et al. "A review of normal tissue hydrogen NMR relaxation times and relaxation mechanisms from 1-100 MHz: Dependence on tissue type, NMR frequency, temperature, species, excision and age," Med. Phys., vol. 11, No. 4, Jul./Aug. 1984, pp. 425-448.
Lyons, G. et al. "Biochemical Changes in Intervertebral Disc Degeneration," Biochimica Biophys Acta, vol. 673, 1981, pp. 443-453.
Maroudas, A.—"The Biology of the Intervertebral Disc"—In: Ghosh, P. el. The Biology of the Intervertebral Disc, vol. II, Chapter 9, 1988.
Pearce, R. et al.—"Degeneration and the Chemical Composition of the Human Lumbar Intervertebral Disc"—Jour. of Ortho. Research, vol. 5, 1987, pp. 198-205.
Tertti, M. et al.—"Disc Degeneration in Magnetic Resonance Imaging: A Comparative Biochemical, Histologic, and Radiologic Study in Cadaver Spines"—Spine, 1991, pp. 629-634.

Chiu, E. et al.—"Magnetic Resonance Imaging Measurement of Relaxation and Water Diffusion in the Human Lumbar Intervertebral Disc Under Compression in Vitro"—Spine, vol. 26, No. 19,2001, pp. E437-E444.
Gundry, C. et al.—"Magnetic Resonance Imaging of the Musculoskeletal System, Part 8. The Spine, Section 1", Clinical Ortho. and Related Research, vol. 338, May 1997, pp. 275-287.
Gunzburg, R. et al.—"A Cadaveric Study Comparing Discography, Magnetic Resonance Imaging, Histology, and Mechanical Behavior of the Human Lumbar Disc"—Spine, 1991, pp. 417-426.
Modic, M. et al.—"Magnetic Resonance Imaging of Intervertebral Disk Disease"—Radiology, vol. 152, 1984, pp. I03-111.
Modic, M. et al.—"Lumbar Herniated Disk Disease and Canal Stenosis: Prospective Evaluation by Surface Coil MR, CT, and Myelography"—AJR, vol. 147, Oct. 1986, pp. 757-765.
Modic, M. et al.—"Imaging of Degenerative Disk Disease"—Radiology, vol. 168, 1988, pp. 177-186.
Sether, L. et al.—"Intervertebral Disk: Normal Age-related Changes in MR Signal Intensity"—Radiology, vol. 177, 1990, pp. 385-388.
Pfirrmann, C. et al.—"Magnetic Resonance Classification of Lumbar Intervertebral Disc Degeneration"—Spine, vol. 26, No. 17, pp. 1873-1878.
Nieminen, M. et al.—"Spatial Assessment of Articular Cartilage Proteoglycans with Gd-DTPA-Enhanced TI Imaging"—Mag. Res. in Med., vol. 48, 2002, pp. 640-648.
Mosher, T. et al.—"Human Articular Cartilage: Influence of Aging and Early Symptomatic Degeneration on the Spatial Variation ofT2—Preliminary Findings at 3 TI"—Radiology, vol. 214, 2000, pp. 259-266.
Burstein, D. et al.—"Diffusion of Small Solutes in Cartilage as Measured by Nuclear Magnetic Resonance (NMR) Spectroscopy and Imaging"—Jour. of Ortho. Res., vol. 11, 1993, pp. 465-478.
Abdulkarim, J. et al.—"Magnetic Resonance Imaging of the Cervical Spine: Frequency of Degenerative Changes in the Intervertebral Disc With Relation to Age"—Clinical Radiology, vol. 58, 2003, pp. 980-984.
Swanson, M. et al.—"Proton HR-MAS Spectroscopy and Quantitative Pathologic Analysis of MRI/3D-MRSI-Targeted Postsurgical Prostate Tissues"—Mag. Resonance in Med., vol. 54, 2003, pp. 944-954.
Schiller, J., et al. "H and C-13 HR-MAS NMR Investigations on Native and Enzymatically Digested Bovine Nasal Certilage." Magnetic Resonance Materials in Physics 2001; 13:19-27.
Carr, H. et al.—"Effects of Diffusion on Free Precession in Nuclear Magnetic Resonance Experiments"—Phys. Review, vol. 94, No. 3, May 1, 1954, pp. 630-638.
Kupce, E.—"Applications of Adiabatic Pulses in Biomolecular Nuclear Magnetic Resonance"—Methods in Enzymology, vol. 338, 2001, pp. 82-111.
Mucci, A. et al.—"1 Hand 13C nuclear magnetic resonance identification and characterization of components of chondroitin sulfates of various origin"—Carbohydrate Polymers, vol. 41, 2003, pp. 37-45.
Groupille, P. et al.—"Matrix Metalloproteinases: The Clue to Intervertebral Disc Degeneration?"—Spine, vol. 23, No. 14, Jul. 1998, pp. 1612-1626.
Kang, J. et al.—"Towards a Biochemical Understanding of Human Intervertebral Disc Degeneration and Herniation: Contributions of Nitric Oxide, Interleukins, Prostaglandin E2, and Matrix Metalloproteinases"—spine, vol. 22, No. 10, May 15, 1997, pp. 1065-1073.
Weiler, C. et al.—"2002 SSE Award Competition in Basic Science: Expression of major matrix metalloproteinases is associated with intervertebral disc degradation and resorption"—Eur. Spine Jour., vol. 11, 2002, pp. 308-320.
Urban, J. et al.—"The Nucleus of the Intervertebral Disc from Development to Degeneration"—American Zoologist, vol. 40, No. 1, Feb. 2000, pp. 53-61.
Weidenbaum, M. et al.—"Correlating Magnetic Resonance Imaging with the Biochemical Content of the Normal Human Intervertebral Disc"—Jour. of Ortho. Research, vol. 10, 1992, pp. 552-561.

(56) References Cited

OTHER PUBLICATIONS

Boos, N. et al.—"Quantitative MR Imaging of Lumbar Intervertebral Disks and Vertebral Bodies: Influence of Diurnal Water Content Variations"—Radiology, vol. 188, 1993, pp. 351-354.
Boos, N. et al.—"Quantitative MR Imaging of Lumbar Intervertebral Discs and Vertebral Bodies: Methodology, Reproducibility, and Preliminary Results"—Mag. Res. Imaging, vol. 12, No. 4, 1994, pp. 577-587.
Keshari, K et al.—Poster and Abstract—"Identification of Chondroitin Sulfate as a Marker for Human Intervertebral disc Degeneration Using Proton High Resolution Magic Angle Spinning *HR-MAS) Spectroscopy"—The 44th ENC, Mar. 30-Apr. 4, 2003, 22 pages.
Majumdar, S.—Abstract—"Spectroscopic Markers of Disc Degeneration."—downloaded from CRISP website Nov. 23, 2004, 2 pages.
Petrantonaki, M., et al. "MRI Techniques for the Examination of Trabecular Bone Structure." Current Medical Imaging Reviews 2005, 1:35-41.
Ford, J. C., et al. "In Vivo Quantitative Characterization of Trabecular Bone by NMR Interferometry and Localized Proton Spectroscopy." Magnetic Resonance in Medicine 1991; 17: 543-551.
Schiller, J., et al. "Evaluation of Cartilage Composition and Degradation by High-Resolution Magic-Angle Spinning Nuclear Magnetic Resonance." Methods in Molecular Medicine 2004; 101:267-285.
Chung, C. T., et al. "Single photon emission computed tomography (SPECT) for low back pain induced by extension with no root sign." J. Chin. Med. Assoc. vol. 67, pp. 349-354 (2004).
Lusins, J. O., et al. "SPECT and lumbar MRI in back pain with emphasis on changes in end plates in association with disc degeneration (abstract)." J. Neuroimaging, vol. 8, No. 2, pp. 78-82 (1998).
McDonald, M., et al. "Use of computer tomography—single-photon emission computed tomography fusion for diagnosing painful facet arthropathy." Neurosurg. Focus, vol. 22, No. 1, E2 (2007).
Mulconrey, D. S., et al. "Interobserver reliability in the interpretation of diagnostic lumbar MRI and Nuclear imaging." The Spine Journal, vol. 6, pp. 177-184 (2006).
Keshari, K., et al. "Potential metabolic markers for intervertebral disc pain." Proc. Intl. Soc. Mag. Reson. Med. 14, p. 1710. May 9, 2006.
Savvopoulou, V., et al. "Degenerative Endplate Changes of the Lumbosacral Spine: Dynamic Contrast-Enhanced MRI Profiles Related to Age, Sex, and Spinal Level." Journal of Magnetic Resonance Imaging 33:382-389 (2011).
Hassler, O. "The Human Intervertebral Disc: A Micro-Angiographical Study on Its Vascular Supply at Various Ages." Acta Orthop. Scandinav. 40, 765-772, 1970.
Niinimaki, J., et al. "Association of lumbar artery narrowing, degenerative changes in disc and endplate and apparent diffusion in disc on postcontrast enhancement of lumbar intervertebral disc." Magn. Reson. Mater Phy. 22:101-109 (2009).
Rajasekaran, S., et al. "ISSLS Prize Winner: A Study of Diffusion in Human Lumbar Discs: A Serial Magnetic Resonance Imaging Study Documenting the Influence of the Endplate on Diffusion in Normal and Degenerate Discs." SPINE vol. 29, No. 23, pp. 2654-2667 (2004).
Liu, Y., et al. "Intervertebral Disk Degeneration Related to Reduced Vertebral Marrow Perfusion at Dynamic Contrast-Enhanced MRI." AJR:192: 974-979, Apr. 2009.
Bolan, Patrick J., et al., "Measurement and Correction of Repiration-Induced Bo Variations in Breast 1H MRS at 4 Tesla," Magnetic Resonance in Medicine 52:000-000 (2004).
Lorenz, C., et al. "3D Statistical Shape Models for Medical Image Segmentation," pp. 414-423, Second International Conference on 3-D Imaging and Modeling (3DIM '99), 1999.
Lin C S et al: "2D CSI proton MR spectroscopy of human spinal vertebra: feasibility studies.", Journal of Magnetic Resonance Imaging : JM RI Mar. 2000, vol. II, No. 3, Mar. 2000, pp. 287-293.

"Spectroscopy reconstruction" and "Spectroscopy processing" In: "Intera Spectroscopy—Instructions for Use", Jul. 2002 (Jul. 2002), Philips Medical Systems, Netherlands, pp. 6-1 to 7-6.
Dubey P. et al.: "Proton MR Spectroscopic Imaging of the Human Cervical Spine at 3 Tesla", Proceedings of the International Society for Magnetic Resonance in Medicine, $13^{th}$ Meeting Proceedings, May 7, 2005 (May 7, 2005), p. 812.
Majumdar, "Review Article Magnetic resonance imaging and spectroscopy of the intervertebral disc," NMR in Biomed (2006) 19: 894-903.
Carragee et al., "Prospective Controlled Study of the Development of Lower Back Pain in Previously Asymptomatic Subjects Undergoing Experimental Discography." SPINE vol. 29, No. 10, pp. 1112-1117 (2004).
Carrino et al., "Prospective evaluation of contrast-enhanced MR imaging after uncomplicated lumbar discography." Skeletal Radiol (2007) 36:293-299.
Derincek et al., "Discography: can pain in a morphologically normal disc be due to an adjacent abnormal disc?" Arch Orthop Trauma Surg (2007) 127:699-703.
Boden et al., "Abnormal magnetic-resonance scans of the lumbar spine in asymptomatic subjects. A prospective investigation." The Journal of Bone & Joint Surgery (1990) 72:403-408.
Boos et al., "Natural History of Individuals With Asymptomatic Disc Abnormalities in Magnetic Resonance Imaging; Predictors of Low Back Pain-Related Medical Consultation and Work Incapacity." SPINE vol. 25, No. 12, pp. 1484-1492 (2000).
Borenstein et al., "The Value of Magnetic Resonance Imaging of the Lumbar Spine to Predict Low-Back Pain in Asymptomatic Subjects: A Seven-Year Follow-up Study." The Journal of Bone & Joint Surgery (2001) 83:1306-1311.
Carragee et al., "2004 Outstanding Paper Award: Nonoperative Science; Discographic, MRI and psychosocial determinants of low back pain disability and remission: a prospective study in subjects with benign persistent back pain." The Spine Journal 5 (2005) 24-35.
Cherkin et al., "Physician Variation in Diagnostic Testing for Low Back Pain." Arthritis & Rheumatism, vol. 37, No. 1, Jan. 1994, pp. 15-22.
Freeborn et al., Primary Care Physicians' Use of Lumbar Spine Imaging Tests: Effects of Guidelines and Practice Pattern Feedback. JGIM, vol. 12, Oct. 1997, pp. 619-625.
Peng Z, "Automated Vertebra Detection and Segmentation from the Whole Spine MR Images," Proceedings of the 2005 IEEE Engineering in Medicine and Biology $27^{th}$ Annual Conference, Shanghai, China, Sep. 1-4, 2005.
Wu M et al., "Quantitative comparison of AIR, SPM, and the fully deformable model for atlas-based segmentation of functional and structural MR images." Hum Brain Mapp. Sep. 2006; 27(9):747-54.
Liu J et al., "Rigid model-based 3D segmentation of the bones of joints in MR and CT images for motion analysis." Med Phys. Aug. 2008;35(8):3637-49.
Liu J et al., "Oriented active shape models." IEEE Trans Med Imaging. Apr. 2009; 28(4):571-84.
Chevrefils C et al., "Texture analysis for automatic segmentation of intervertebral disks of scoliotic spines from MR images." IEEE Trans Inf Technol Biomed. Jul. 2009; 13(4):608-20.
Huang SH et al., "Learning-based vertebra detection and iterative normalized-cut segmentation for spinal MRI." IEEE Trans Med Imaging. Oct. 2009; 28(10):1595-605.
Michopoulou SK et al., "Atlas-based segmentation of degenerated lumbar intervertebral discs from MR images of the spine." IEEE Trans Biomed Eng. Sep. 2009; 56(9):2225-31.
Kadoury S et al., "Personalized X-ray 3-D reconstruction of the scoliotic spine from hybrid statistical and image-based models." IEEE Trans Med Imaging. Sep. 2009; 28(9):1422-35.
Koh J et al., "Automatic segmentation of the spinal cord and the dural sac in lumbar MR images using gradient vector flow field." Conf Proc IEEE Eng Med Biol Soc. 2010; 2010:3117-20.
Hao S et al., "[Spine disc MR image analysis using improved independent component analysis based active appearance model and Markov random field]." Sheng Wu Yi Xue Gong Cheng Xue Za Zhi. Feb. 2010;27(1):6-9, 15.

(56) References Cited

OTHER PUBLICATIONS

Horsfield MA et al., "Rapid semi-automatic segmentation of the spinal cord from magnetic resonance images: application in multiple sclerosis." Neuroimage. Apr. 1, 2010; 50(2):446-55.
Bechara BP et al., "Application of a semiautomated contour segmentation tool to identify the intervertebral nucleus pulposus in MR images." AJNR Am J Neuroradiol. Oct. 2010; 31(9):1640-4.
Ben Ayed I et al., "Graph cuts with invariant object-interaction priors: application to intervertebral disc segmentation." Inf Process Med Imaging. 2011;22:221-32.
Dalca A et al., "Segmentation of nerve bundles and ganglia in spine MRI using particle filters." Med Image Comput Comput Assist Interv. 2011; 14(Pt 3):537-45.
Michopoulou S et. al., "Texture-based quantification of lumbar intervertebral disc degeneration from conventional T2-weighted MRI," Acta Radiologica 2011; 52: 91-98.
Neubert A, "Automated 3D Segmentation of Vertebral Bodies and Intervertebral Discs from MRI," 2011 International Conference on Digital Image Computing: Techniques and Applications.
Strickland CG et al., "Development of subject-specific geometric spine model through use of automated active contour segmentation and kinematic constraint-limited registration." J Digit Imaging. Oct. 2011; 24(5):926-42.
Giulietti G et al., "Semiautomated segmentation of the human spine based on echoplanar images," Magn Reson Imaging. Dec. 2011; 29(10):1429-36.
Stern D et al., "Parametric modelling and segmentation of vertebral bodies in 3D CT and MR spine images." Phys Med Biol. Dec. 7, 2011; 56(23):7505-22.
Neubert A et. al., "Automated detection, 3D segmentation and analysis of high resolution spine MR images using statistical shape models." Phys Med Biol. Dec. 21, 2012; 57(24):8357-76.
Egger J et al., "Square-cut: a segmentation algorithm on the basis of a rectangle shape." PLoS One. Dated Feb. 2012. 7(2).
Vrtovec T et al., "Automated curved planar reformation of 3D spine images." Phys Med Biol. Oct. 7, 2005; 50(19):4527-40.
Bandettini, Patricia et al., "MultiContrast Delayed Enhancement (MCODE) improves detection of subendocardial myocardial infarction by late gadolinium enhancement cardiovascular magnetic resonance: a clinical validation study", Journal of Cardiovascular Magnetic Resonance, vol. 14, No. I, Nov. 30, 2012 (Nov. 30, 2012).
Comments Regarding U.S. Appl. No. 12/579,371 (filed Oct. 14, 2009) and PCT Patent Application No. PCT/US2010/052737 (Filed Oct. 14, 2010).
Vos T, Flaxman AD, Naghavi M, et al. Dec. 2012. Years lived with disability (YLDs) for 1160 sequelae of 289 diseases and injuries 1990-2010: a systematic analysis for the Global Burden of Disease Study 2010. Lancet 380(9859):2163-96.
Thompson KJ, Dagher AP, Eckel TS, et al. Mar. 2009. Modic changes on MR images as studied with provocative diskography: clinical relevance—a retrospective study of 2457 disks. Radiology 250(3):849-55.
Modic MT, Steinberg PM, Ross JS, et al. Jan. 1988. Degenerative disk disease assessment of changes in vertebral body marrow with MR imaging. Radiology 166(1 Pt 1): 193-9.
Jensen TS, Karppinen J, Sorensen JS, et al. Sep. 12, 2008. Vertebral endplate signal changes (Modic change): a systematic literature review of prevalence and association with non-specific low back pain. Eur. Spine J. 17(11): 1407-22.
Jensen OK, Nielsen CV, Sorensen JS, Stengaard-Pedersen K. Nov. 1, 2014. Type 1 Modic changes was a significant risk factor for 1-year outcome in sick-listed low back pain patients: a nested cohort study using magnetic resonance imaging of the lumbar spine. Spine J. 14(11):2568-81.
Schistad EI, Espeland A, Rygh LJ, et al. Jun. 26, 2014. The association between Modic changes and pain during 1-year follow-up in patients with lumbar radicular pain. Skeletal Radiol. 43(9):1271-9.
Järvinen J, Karppinen J, Niinimäki J, et al. Apr. 22, 2015. Association between changes in lumbar Modic changes and low back symptoms over a two-year period. BMC Musculoskelet. Disord. 16(1):98.
Albert HB, Lambert P, Rollason J, et al. Feb. 10, 2013. Does nuclear tissue infected with bacteria following disc herniations lead to Modic changes in the adjacent vertebrae? Eur. Spine J. 22(4):690-6.
Vowels BR, Yang S, Leyden JJ. Aug. 1995. Induction of proinflammatory.cytokines by a soluble factor of Propionibacterium acnes: implications for chronic inflammatory acne. Infect. Immun. 63(8):3158-65.
McDowell A, Barnard E, Nagy I, et al. Jul. 2012. An expanded multilocus sequence typing scheme for propionibacterium acnes: investigation of "pathogenic", "commensal" and antibiotic resistant strains. PLoS One 7(7):e41480.
Valanne S, McDowell A, Ramage G, et al. May 2005. CAMP factor homologues in Propionibacterium acnes: A new protein family differentially expressed by types I and II. Microbiology 151(5):1369-1379.
Stirling A, Worthington T, Rafiq M, et al. Jun. 23, 2001. Association between sciatica and Propionibacterium acnes. Lancet 357(9273):2024-5.
Rollason J, McDowell A, Albert HB, et al. Aug. 2013. Genotypic and antimicrobial characterisation of Propionibacterium acnes isolates from surgically excised lumbar disc herniations. Biomed Res. Int. 2013:530382.
Albert HB, Sorensen JS, Christensen BS, Manniche C. Feb. 13, 2013. Antibiotic treatment in patients with chronic low back pain and vertebral bone edema (Modic type 1 changes): a double-blind randomized clinical controlled trial of efficacy. Eur. Spine J. 22(4):697-707.
Fritzell P, Bergstrom T, Welinder-Olsson C. May 8, 2004. Detection of bacterial DNA in painful degenerated spinal discs in patients without signs of clinical infection. Eur. Spine J. 13(8):702-6.
Wedderkopp N, Thomsen K, Manniche C, et al. Jul. 9, 2009. No evidence for presence of bacteria in modic type I changes. Acta Radiol. 50(1):65-70.
Arndt J, Charles YP, Koebel C, et al. Oct. 2012. Bacteriology of degenerated lumbar intervertebral disks. J. Spinal Disord. Tech. 25(7):E211-6.
Bhanji S, Williams B, Sheller B, et al. Jul.-Aug. 2002. Transient bacteremia induced by toothbrushing a companson of the Sonicare toothbrush with a conventional toothbrush. Pediatr. Dent. 24(4):295-9.
Urquhart DM, Zheng Y, Cheng AC, et al. Jan. 22, 2015. Could low grade bacterial infection contribute to low back pain? A systematic review. BMC Med. 13(1):13.
Weiner BK, Vilendecic M, Ledic D, et al. 2015. Published online Dec. 28, 2014. Endplate changes following discectomy: natural history and associations between imaging and clinical data. Eur. Spine J. 24(11):2449-57.
Kerttula L, Luoma K, Vehmas T, et al. Jan. 17, 2012. Modic type I change may predict rapid progressive, deforming disc degeneration: a prospective 1-year follow-up study. Eur. Spine J. 21(6):1135-42.
Holm S, Baranto A, Kaigle Holm A, et al. 2007. Reactive changes in the adolescent porcine spine with disc degeneration due to endplate injury. Vet. Comp. Orthop. Traumatol. 20(1):12-7.
McDowell A, Valanne S, Ramage G, et al. Jan. 2005. Propionibacterium acnes types I and II represent phylogenetically distinct groups. J. Clin. Microbial. 43(1):326-34.
Nadkarni MA, Martin FE, Jacques NA, Hunter N. Jan. 2002. Determination of bacterial load by real-time PCR using a broad-range (universal) probe and primers set. Microbiology 148(1):257-266.
Mühl H, Kochem A-J, Disqué C, Sakka SG. Jan. 2010. Activity and DNA contamination of commercial polymerase chain reaction reagents for the universal 16S rDNA real-time polymerase chain reaction detection of bacterial pathogens in blood. Diagn. Microbial. Infect. Dis. 66(1):41-9.
Burke J, Watson R, McCormack D, et al. Feb. 21, 2003. Endplate changes are associated with increased disc inflammatory mediator production. J Bone Jt. Surg Br 85-B(Supp II): 164.

(56) References Cited

OTHER PUBLICATIONS

Klawitter M, Hakozaki M, Kobayashi H, et al. Jul. 5, 2014. Expression and regulation of toll-like receptors (TLRs) in human intervertebral disc cells. Eur. Spine J. 23(9):1878-91.

Quero L, Klawitter M, Schmaus A, et al. Aug. 22, 2013. Hyaluronic acid fragments enhance the inflammatory and catabolic response in human intervertebral disc cells through modulation of toll-like receptor 2 signaling pathways. Arthritis Res. Ther. 15(4):R94.

Ellman MB, Kim J-S, An HS, et al. Jun. 10, 2012. Toll-like receptor adaptor signaling molecule MyD88 on intervertebral disk homeostasis: In vitro, ex vivo studies. Gene 505(2):283-90.

Wang J, Tian Y, Phillips KLE, et al. Mar. 2013. Tumor necrosis factor α- and interleukin-1β-dependent induction of CCL3 expression by nucleus pulposus cells promotes macrophage migration through CCR1. Arthritis Rheum. 65(3):832-42.

Le Maitre CL, Hoyland JA, Freemont AJ. Aug. 9, 2007. Catabolic cytokine expression in degenerate and herniated human intervertebral discs: IL-1β and TNFα expression profile. Arthritis Res. Ther. 9(4):R77.

Burke JG, G Watson RW, Conhyea D, et al. Dec. 2003. Human nucleus pulposis can respond to a pro-inflammatory stimulus. Spine (Phila. Pa. 1976). 28(24):2685-93.

Li B, Dong Z, Wu Y, et al. Jul. 2016. Association between Lumbar Disc degeneration and Propionibacterium Acnes Infection: Clinical Research and Preliminary Exploration of Animal Experiment. Spine (Phila. Pa. 1976). [Epub ahead of print].

Ferguson SJ, Ito K, Nolte LP. Feb. 2004. Fluid flow and convective transport of solutes within the intervertebral disc. J. Biomech. 37(2):213-21.

Mirantes C, Passegué E, Pietras EM. Aug. 19, 2014. Pro-inflammatory cytokines: Emerging players regulating HSC function in normal and diseased hematopoiesis. Exp. Cell Res. :1-7.

Dudli S, Sing D, Burch S, et al. Mar. 2, 2016. Molecular and Cellular Changes in Vertebral Bone Marrow Lesions. In: Annual Meeting American Academy of Orthopaedic Surgeons. Orlando; Paper 454.

Dudli S, Haschtmann D, Ferguson SJ. 2012. Published online Oct. 24, 2011. Fracture of the vertebral endplates, but not equienergetic impact load, promotes disc degeneration in vitro. J. Orthop. Res. 30(5):809-16.

Torkki M, Majuri M-L, Wolff H, et al. Mar. 27, 2015. Osteoclast activators are elevated in intervertebral disks with Modic changes among patients operated for herniated nucleus pulposus. Eur. Spine J. [Epub ahead of print].

Perilli E, Parkinson IH, Truong L-H, et al. Jul. 26, 2014. Modic (endplate) changes in the lumbar spine: bone micro-architecture and remodelling. Eur. Spine J. 24(9):1926-34.

Mackiewicz Z, Salo J, Konttinen YT, et al. Mar.-Apr. 2009. Receptor activator of nuclear factor kappa B ligand in an experimental intervertebral disc degeneration. Clin. Exp. Rheumatol. 27(2):299-306.

Laasonen LS, Karvonen SL, Reunala TL. May 1994. Bone disease in adolescents with acne fulminans and severe cystic acne: radiologic and scintigraphic findings. AJR. Am. J. Roentgenol. 162(5):1161-1165.

Ziegler P, Boettcher S, Takizawa H, et al. 2016. Published online Nov. 11, 2015. LPS-stimulated human bone marrow stroma cells support myeloid cell development and progenitor cell maintenance. Ann. Hematol. 95(2): 173-8.

Wan Y, Chong L-W, Evans RM. Dec. 2007. PPAR-gamma regulates osteoclastogenesis in mice. Nat. Med. 13(12):1496-503.

Piccinini AM, Midwood KS. Jul. 2010. DAMPening inflammation by modulating TLR signalling. Mediators Inflamm. 2010.

Oegema TR, Johnson SL, Aguiar DJ, Ogilvie JW. Nov. 2000. Fibronectin and its fragments increase with degeneration in the human intervertebral disc. Spine (Phila. Pa. 1976). 25(21):2742-7.

Patel KB, Poplawski MM, Pawha PS, et al. Aug. 2014. Diffusion-weighted MRI "claw sign" improves differentiation of infectious from degenerative modic type 1 signal changes of the spine. AJNR. Am. J. Neuroradiol. 35(8):1647-52.

Di Martino A, Merlini L, Faldini C. Aug. 30, 2013. Autoimmunity in intervertebral disc herniation: from bench to bedside. Expert Opin. Ther. Targets 17(12):1461-70.

Ulrich JA, Liebenberg EC, Thuillier DU, et al. Dec. 2007. ISSLS prize winner: repeated disc injury causes persistent inflammation. Spine (Phila. Pa. 1976). 32, 2812-9.

Bendix T, Sorensen JS, Henriksson GAC, et al. Sep. 15, 2012. Lumbar modic changes—a comparison between findings at low- and high-field magnetic resonance imaging. Spine (Phila. Pa. 1976). 37, 1756-62.

McDowell A, Perry AL, Lambert PA, er al. Feb. 2008. A new phylogenetic group of Propionibacterium acnes. J. Med. Microbial. 57, 218-24.

Sharif, H. S. Role of MR imaging in the management of spinal infections. Jun. 1992. AJR Am J Roentgenol 158, 1333-1345.

Bertok L. Apr. 2005. Natural immunity, First Edit. Elsevier Science; 291 p.

Inagawa H, Kohchi C, Soma G-1. Jul. 2011. Oral administration of lipopolysaccharides for the prevention of various diseases: benefit and usefulness. Anticancer Res. 31(7):2431-6.

Chen Z, Zheng Y, Yuan Y, et al. (Jan. 26, 2016) Modic Changes and Disc Degeneration Caused by Inoculation of Propionibacterium acnes inside Intervertebral Discs of Rabbits: A Pilot Study. Biomed Res Int 2016:9612437.

Zuo, Assessment of Intervertebral Disc Degeneration With Magnetic Resonance Single-Voxel Spectroscopy, Magnetic Resonance in Medicine, 62: 1140-1146 (Sep. 24, 2009).

Freemont, AJ., The cellular pathobiology of the degenerate intervertebral disc and discogenic back pain, (2009) Rheumatology; 48:5-10. (Advanced access publication Oct. 14, 2008).

Dudli, S. et al. "Propionibacterium acnes infected intervertebral discs cause vertebral bone marrow lesions consistent with Modic changes." J. Orthop. Res. Aug. 2016 34(8):1447-55.

Urban, Winlove, "Pathophysiology of the Intervertebral Disc and the Challenges for MRI." J. Magnetic Resonance Imaging. 25(2):419-32. Feb. 2007.

Gornet, Matthew et al., "Magentic Resonance Spectroscopy (MRS) can identify painful lumbar dics and may facilitate improved clinical outcomes of lumbar surgeries for discogenic pain", European Spine Journal, Jan. 4, 2019.

Magnitsky, Sergey et al., "Quantification of Propionic Acid in the Bovine Spinal Disk After Infection of the Tissue With Propionibacteria acnes Bacteria", Spine Journal, vol. 43, No. 11, pp. E634-E638, Jun. 2018.

"Solving Low Back Pain: If We Can't Measure It, We Can't Improve It," Jeffrey C. Lotz, PhD, presented on Nov. 10, 2015 at the International Philadelphia Spine Research Symposium.

International Search Report and Written Opinion dated Jul. 27, 2011 issued to international application No. PCT/US2010/052737.

International Search Report and Written Opinion dated Jul. 26, 2013 for international application No. PCT/US2013/036014.

International Search Report and Written Opinion dated Aug. 1, 2012 for PCT Application No. PCT/US2011/062137.

International Search Report and Written Opinion dated Sep. 25, 2014 for PCT Application No. PCT/US2014/022845.

International Search Report and Written Opinion dated Aug. 18, 2017 for PCT Application No. PCT/US2017/038034.

\* cited by examiner

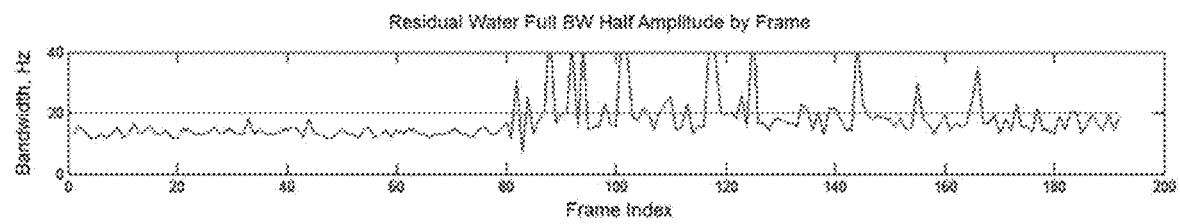
FIG. 7A
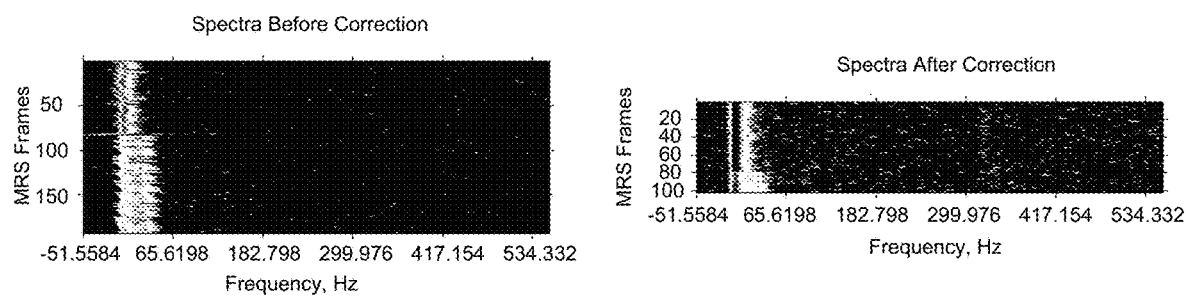
FIG. 7B
FIG. 7C
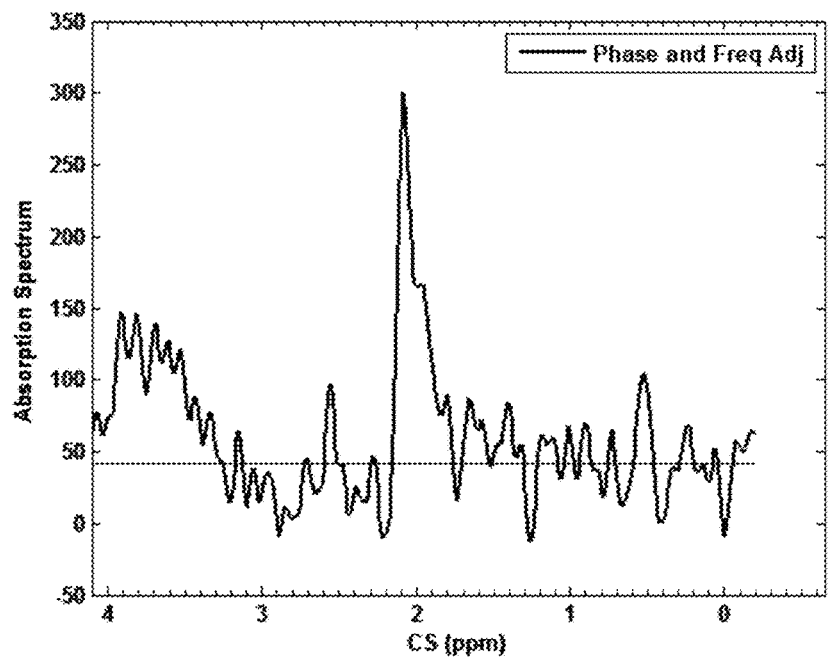
FIG. 7D

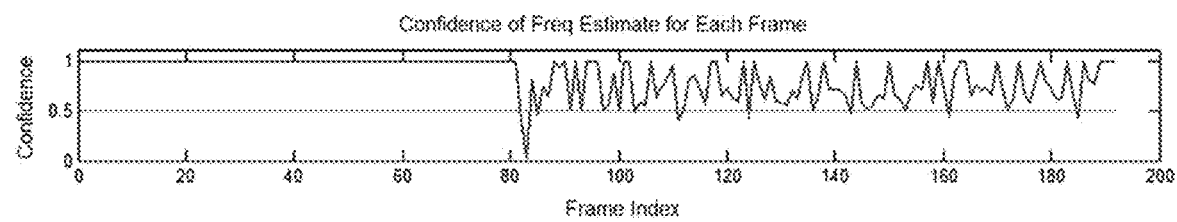
FIG. 8A
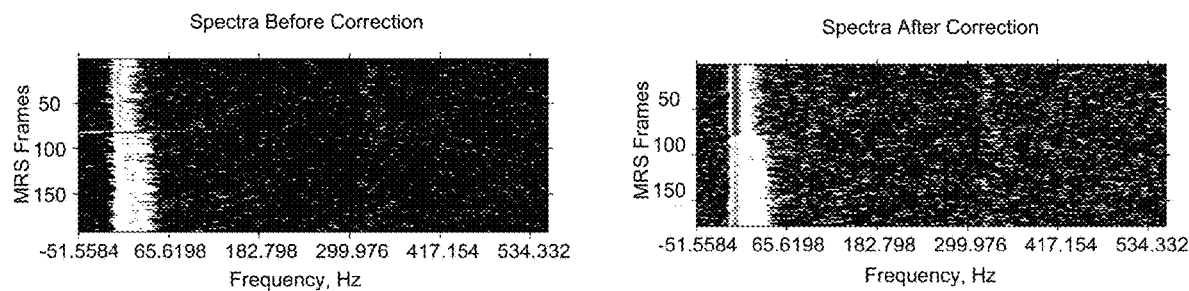
FIG. 8B
FIG. 8C
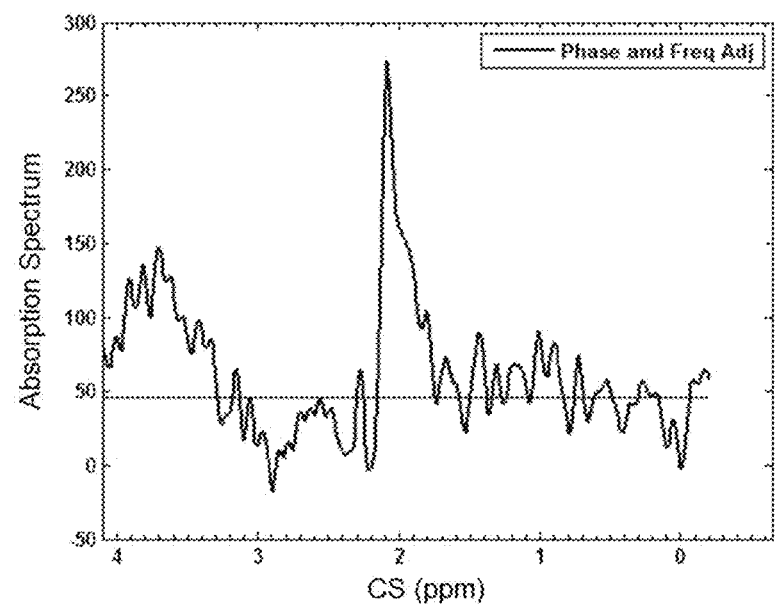
FIG. 8D

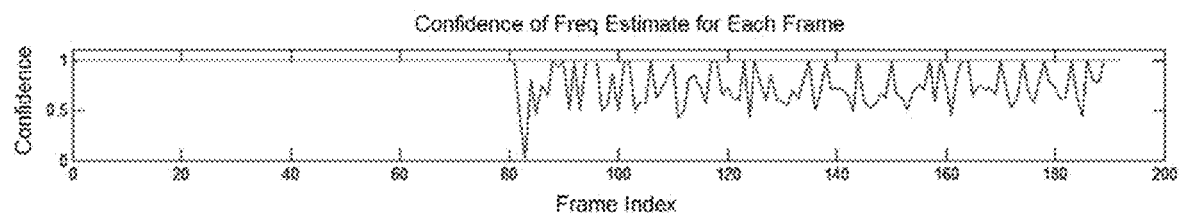
FIG. 9A
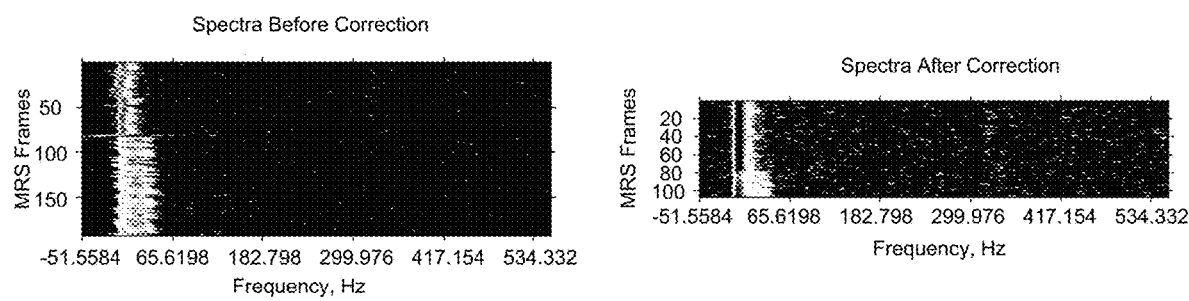
FIG. 9B
FIG. 9C
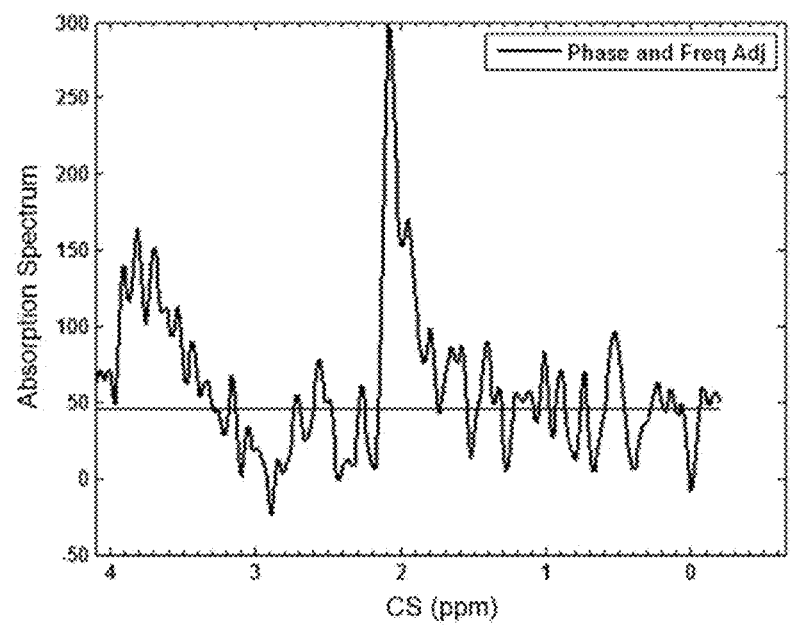
FIG. 9D

MAGNETIC RESONANCE SPECTROSCOPY PULSE SEQUENCE, ACQUISITION, AND PROCESSING SYSTEM AND METHOD

CROSS-REFERENCE TO RELATED APPLICATIONS

This application is a continuation of U.S. patent application Ser. No. 15/160,423, filed May 20, 2016, and titled MAGNETIC RESONANCE SPECTROSCOPY PULSE SEQUENCE, ACQUISITION, AND PROCESSING SYSTEM AND METHOD, which is a continuation of U.S. patent application Ser. No. 14/625,918, filed Feb. 19, 2015, and titled MAGNETIC RESONANCE SPECTROSCOPY PULSE SEQUENCE, ACQUISITION, AND PROCESSING SYSTEM AND METHOD, which is a continuation of U.S. patent application Ser. No. 13/843,117, filed Mar. 15, 2013, and titled MAGNETIC RESONANCE SPECTROSCOPY PULSE SEQUENCE, ACQUISITION, AND PROCESSING SYSTEM AND METHOD, which claims the benefit under 35 U.S.C. § 119(e) of U.S. Provisional Patent Application No. 61/624,284, filed Apr. 14, 2012, and titled MAGNETIC RESONANCE SPECTROSCOPY PULSE SEQUENCE, ACQUISITION, AND PROCESSING SYSTEM AND METHOD. The above-identified applications are hereby incorporated by reference in their entirety and made a part of this specification for all that they disclose.

INCORPORATION BY REFERENCE

The following disclosures are hereby incorporated by reference in their entirety and made a part of this specification for all that they disclose: U.S. Patent Publication No. 2008/0039710, filed Jul. 27, 2007, and titled "SYSTEM AND METHODS USING NUCLEAR MAGNETIC RESONANCE (NMR) SPECTROSCOPY TO EVALUATE PAIN AND DEGENERATIVE PROPERTIES OF TISSUE"; U.S. Patent Publication No. 2009/0030308, filed Mar. 21, 2008, and titled "SYSTEM, COMPOSITION, AND METHODS FOR LOCAL IMAGING AND TREATMENT OF PAIN"; International Patent Publication No. WO 2009/148550, filed May 29, 2009, and titled "BIOMARKERS FOR PAINFUL INTERVERTEBRAL DISCS AND METHODS OF USE THEREOF"; U.S. Patent Publication No. 2011/0087087, filed Oct. 14, 2009, and titled "MR SPECTROSCOPY SYSTEM AND METHOD FOR DIAGNOSING PAINFUL AND NON-PAINFUL INTERVERTEBRAL DISCS"; International Patent Publication No. WO 2011/047197, filed Oct. 14, 2010, and titled "MR SPECTROSCOPY SYSTEM AND METHOD FOR DIAGNOSING PAINFUL AND NON-PAINFUL INTERVERTEBRAL DISCS"; and U.S. patent application Ser. No. 13/830,632, filed Mar. 14, 2013, and titled SYSTEMS AND METHODS FOR AUTOMATED VOXELATION OF REGIONS OF INTEREST FOR MAGNETIC RESONANCE SPECTROSCOPY.

BACKGROUND OF THE INVENTION

Field of the Invention

This disclosure relates to systems, processors, devices, and methods for measuring chemical constituents in tissue for diagnosing medical conditions. More specifically, it relates to systems, pulse sequences, signal and diagnostic processors, diagnostic displays, and related methods using novel application of nuclear magnetic resonance, including magnetic resonance spectroscopy, for diagnosing pain such as low back pain associated with degenerative disc disease.

Description of the Related Art

While significant effort has been directed toward improving treatments for discogenic back pain, relatively little has been done to improve the diagnosis of painful discs—at least until quite recently.

Magnetic resonance imaging (MRI) is the primary standard of diagnostic care for back pain. An estimated ten million MRIs are done each year for spine, which is the single largest category of all MRIs at an estimated 26% of all MRIs performed. MM in the context of back pain is sensitive to changes in disc and endplate hydration and structural morphology, and often yields clinically relevant diagnoses such as in setting of spondylolysthesis and disc herniations with nerve root impingement (e.g. sciatica). In particular context of axial back pain, MRI is principally useful for indicating degree of disc degeneration. However, degree of disc degeneration has not been well correlated to pain. In one regard, people free of back pain often have disc degeneration profiles similar to those of people with chronic, severe axial back pain. In general, not all degenerative discs are painful, and not all painful discs are degenerative. Accordingly, the structural information provided by standard MRI exams of the lumbar spine is not generally useful for differentiating between painful and non-painful degenerative discs in the region as related to chronic, severe back pain.

Accordingly, a second line diagnostic exam called "provocative discography" (PD) is often performed after MRI exams in order to localize painful discs. This approach uses a needle injection of pressurized dye in awake patients in order to intentionally provoke pain. The patient's subjective reporting of pain level experienced during the injection, on increasing scale of 0-10, and concordancy to usual sensation of pain, is the primary diagnostic data used to determine diagnosis as a "positive discogram"—indicating painful disc—versus a "negative discogram" for a disc indicating it is not a source of the patient's chronic, severe back pain. This has significant limitations including invasiveness, pain, risks of disc damage, subjectivity, and lack of standardization of technique. PD has been particularly challenged for high "false+" rates alleged in various studies, although recent developments in the technique and studies related thereto have alleged improved specificity of above 90%. (Wolfer et al., Pain Physician 2008; 11:513-538, ISSN 1533-3159). However, the significant patient morbidity of the needle-based invasive procedure is non-trivial, as the procedure itself causes severe pain and further compromises time from work. Furthermore, in another recent study PD was shown to cause significant adverse effects to long term disc health, including significantly accelerating disc degeneration and herniation rates (on the lateral side of needle puncture). (Carragee et al., SPINE Volume 34, Number 21, pp. 2338-2345, 2009). Controversies around PD remain, and in many regards are only growing, despite the on-going prevalence of the invasive, painful, subjective, harmful approach as the secondary standard of care following MRI. PD is performed an estimated 400,000 times annually world-wide, at an estimated total economic cost that exceeds $750 Million annually. The need for a non-invasive, painless, objective, non-significant risk, more efficient and cost-effective test to locate painful intervertebral discs of chronic, severe low back pain patients is urgent and growing.

A non-invasive radiographic technique to accurately differentiate between discs that are painful and non-painful may offer significant guidance in directing treatments and developing an evidence-based approach to the care of patients with lumbar degenerative disc disease (DDD).

Magnetic resonance spectroscopy (MRS), and related applications and post-processing techniques, have been previously described. This includes more recently in relation to intervertebral discs and certain diagnostic applications related to medical conditions such as degenerative disc disease and discogenic low back pain. However, such prior efforts and disclosures, despite their alleged benefits, have nonetheless left open certain remaining needs and opportunities for valuable new improvements still yet to be provided.

A need and opportunity still remain for improved MRS acquisition and/or post-processing approaches for providing robust spectra representative of chemical environments of tissues being analyzed. In particular, such a need and opportunity exists to reduce risk of artifact contribution that might confound chemical analysis of the tissue based upon processed MRS spectral data.

A need and opportunity also still remain for improved MRS approaches for disc tissue analysis and diagnosis, such as for example for assisting in the diagnosis of degenerative disc disease and/or discogenic low back pain.

SUMMARY OF THE INVENTION

One aspect of the present disclosure is an MRS post-processor providing enhanced frequency shift artifact correction in signal post-processing of acquired MRS data from tissue.

One aspect of the present disclosure is a MRS pulse sequence configured to generate and acquire a diagnostically useful MRS spectrum from a voxel located principally within an intervertebral disc of a patient.

Another aspect of the present disclosure is an MRS signal processor that is configured to select a sub-set of multiple channel acquisitions received contemporaneously from multiple parallel acquisition channels, respectively, of a multi-channel detector assembly during a repetitive-frame MRS pulse sequence series conducted on a region of interest within a body of a subject.

Another aspect of the present disclosure is an MRS signal processor comprising a phase shift corrector configured to recognize and correct phase shifting within a repetitive multi-frame acquisition series acquired by a multi-channel detector assembly during an MRS pulse sequence series conducted on a region of interest within a body of a subject.

Another aspect of the present disclosure is a MRS signal processor comprising a frequency shift corrector configured to recognize and correct frequency shifting between multiple acquisition frames of a repetitive multi-frame acquisition series acquired within an acquisition detector channel of a multi-channel detector assembly during a MRS pulse sequence series conducted on a region of interest within a body of a subject.

According to one mode of this aspect, the frequency shift corrector comprises a frequency shift estimator configured to estimate a frequency shift error for the frames among the series, and a frequency shift corrector that corrects the frequency shift error based upon the frequency shift estimation for the frames.

According to one embodiment of this mode, the frequency shift estimator is configured to estimate the frequency shift error of the MRS data for the frames in the time domain. According to another embodiment, the frequency shift estimator is configured to estimate the frequency shift error of the MRS data for the frames in the frequency domain. According to another embodiment, the frequency shift corrector is configured to correct in the time domain the frequency shift error estimated by the frequency shift estimator. According to another embodiment, the frequency shift corrector is configured to correct in the frequency domain the frequency shift error estimated by the frequency shift estimator. According to another embodiment, both the frequency shift estimator is configured to estimate the frequency shift error and the frequency shift corrector is configured to correct the frequency shift error in the time domain. According to another embodiment, both the frequency shift estimator is configured to estimate the frequency shift error and the frequency shift corrector is configured to correct the frequency shift error in the frequency domain. According to another embodiment, the frequency shift estimator is configured to estimate the frequency shift error in the time domain, and the frequency shift corrector is configured to correct the frequency shift error in the frequency domain. According to another embodiment, the frequency shift estimator is configured to estimate the frequency shift error in the frequency domain, and the frequency shift corrector is configured to correct the frequency shift error in the time domain.

According to another embodiment, the frequency shift estimator is configured to estimate the frequency shift by comparing each frame with a reference by means of spectral cross-correlation. In one further embodiment, the reference is derived from multiple frames.

Another aspect of the present disclosure is a MRS signal processor comprising a frame editor configured to recognize at least one poor quality acquisition frame, as determined against at least one threshold criterion, within an acquisition channel of a repetitive multi-frame acquisition series received from a multi-channel detector assembly during a MRS pulse sequence series conducted on a region of interest within a body of a subject.

According to one mode of this aspect, the frame editor is further configured to exclude said frames so recognized as poor relative quality from the multi-frame acquisition series for further processing by one or more additional signal processors. According to one embodiment of this mode, the further processing comprises frequency shift correction by a frequency shift corrector.

According to another mode of this aspect, the frame editor comprises a water peak confidence estimator configured to estimate a level or degree of confidence in identifying a water peak signal in the spectral frame, and a water confidence threshold criterion. The frame editor is further configured to recognize and exclude frames from the series having an estimated degree of confidence for the water peak that do not meet the threshold criteria. According to one embodiment, the degree of confidence is estimated as a percent (%) confidence level, on a scale from 0 to 100. According to a further embodiment, the threshold criterion comprises at least about 70 percent confidence. According to another embodiment, the threshold criterion comprises at least about 90 percent confidence. According to another embodiment, the degree of confidence is based at least in part upon an amplitude of the water signal. According to another embodiment, the degree of confidence is based at least in part upon a full width half max amplitude (FWHM) measurement of the water signal.

According to another mode of this aspect, the frame editor comprises a full width half maximum (FWHM) test module, which comprises a FWHM measurement of the water peak and a FWHM measurement threshold criterion. The frame editor is further configured to recognize and exclude frames from the series having a computed FWHM of the water peak that exceeds the threshold criteria.

According to another mode of this aspect, the frame editor comprises a frequency error test module, comprising a frequency error measurement of the water peak and a frequency error threshold criterion. The frequency error is the difference between the computed location of the water peak (maximum peak of the spectrum) and the defined location of the water peak (DC). The editor is further configured to recognize and exclude frames from the series having a frequency error that exceeds the threshold criteria.

Another aspect of the present disclosure is an MRS signal processor that comprises an apodizer to reduce the truncation effect on the sample data. The apodizer can be configured to apodize an MRS acquisition frame in the time domain otherwise generated and acquired by via an MRS aspect otherwise herein disclosed, and/or signal processed by one or more of the various MRS signal processor aspects also otherwise herein disclosed.

Another aspect of the present disclosure is an MRS diagnostic processor configured to process information extracted from an MRS spectrum for a region of interest in a body of a subject, and to provide the processed information in a manner that is useful for diagnosing a medical condition or chemical environment associated with the region of interest.

Another aspect of the present disclosure is an MRS system comprising an MRS pulse sequence, MRS signal processor, and MRS diagnostic processor, and which is configured to generate, acquire, and process an MRS spectrum representative of a region of interest in a body of a patient for providing diagnostically useful information associated with the region of interest.

Another aspect of the present disclosure is an MRS system which adjusts a spectrum in an upfield range relative to water (e.g. <about 4.7 ppm) based upon a measured parameter in a downfield range relative to water (e.g. >about 4.7 ppm). According to one mode, at least one region of an upfield range of less than about 3.5 ppm is adjusted based upon at least one roughly mirrored opposite range of greater than about 5.9 or 6 ppm. These may be accomplished within about +/−0.5 ppm. According to one embodiment, the downfield range is reflected around a central line to mirror the upfield range, and is subtracted from the upfield range. According to one further embodiment, the central line is at about water (e.g. about 4.7 ppm). According to another embodiment, the downfield range is further aligned following reflection for enhanced correlation between the downfield range signals and the upfield range signals. According to another embodiment, the correlation between the aligned downfield and upfield regions is measured and used as a test to apply or bypass the adjustment. According to another embodiment, a signal:noise ratio (SNR) calculation of the adjusted upfield spectrum following subtraction is compared with an SNR calculation prior to the adjustment in order to determine whether to use the adjusted spectrum or discard it and retain the unadjusted spectrum According to another embodiment, the correlation between the reflected and aligned downfield spectrum and the upfield spectrum ranges is used to determine and identify a degree of potential artifact in the upfield spectrum signals.

Still further aspects of the present disclosure comprise various MRS system and method aspects associated with the other MRS system, sequence, and processor aspects described above.

For example, another such aspect comprises processing MRS data from an acquisition series conducted across first and second phase groups comprising first and second sets of acquisition frames acquired at first and second different respective phases along a phase cycle. Further to this aspect, the system and method processes at least in part the first and second phase cycle groups separately. According to one mode of this aspect, the separate phase group processing comprises at least one of the other processing aspects, modes, embodiments, variations, and features elsewhere herein described, such as for example one or more of frequency error estimation, frame editing, frequency correction, and phase correction. According to another mode, the first and second set of acquisition frames for each phase group are combined into one phase group combined result. According to another mode, the first and second phase groups are combined to provide an averaged spectral result following the separate processing. In another mode, the first and second sets of each phase group are combined, and then the combined phase groups are combined. Another mode comprises reducing or removing artifact separately between the phase groups. In another mode, the artifact is removed by combining the phase groups after separate processing and in-group frame combining. In another mode, frame editing is performed on each phase group, and a different number of frames are retained (or conversely filtered out) in each group prior to combining in-group frames and the groups together.

Another aspect of the present disclosure is a method for processing a set of multiple serially acquired magnetic resonance spectroscopy (MRS) free induction decay (FID) frames from a multi-frame MRS acquisition series from a region of interest (ROI) in a subject, and for providing a post-processed MRS spectrum. This method comprises:

dynamically varying a parameter of a processing step between multiple parameter values affecting a corresponding change between multiple feature values of a feature of a processed result of performing the step on the set;

performing the step on the set at each of the multiple parameter values and providing multiple processed results, respectively, comprising multiple respective feature values, respectively;

comparing the feature values of the processed results;

determining a chosen feature value among the multiple feature values based upon the comparison and corresponding to a chosen parameter value; and setting the parameter to the chosen parameter value for performing the processing step to provide the post-processed MRS spectrum.

According to one mode of this method, the chosen feature value comprises a best feature value relative to a quality criterion for the value.

According to another mode, the feature comprises signal: noise ratio (SNR) of a spectral peak region of the post-processed MRS spectrum.

According to another mode, the feature comprises a line width of a spectral peak region of the post-processed MRS spectrum.

According to one embodiment of this mode, the line width comprises a full width half max (FWHM) measurement of a spectral peak region of the post-processed MRS spectrum.

According to another mode, the feature comprises signal: noise ratio (SNR) or full width half max (FWHM) of a spectral peak region of the post-processed MRS spectrum;

and the spectral peak region comprises at least one of a water region and a second region that is different than the water region and corresponding with a chemical of interest for the MRS acquisition.

According to one embodiment of this mode, the second region corresponds with an n-acetyl acetate (NAA) chemical bond.

According to another mode, the processing step comprises: frame editing by comparing a quality value for a quality of each frame against a threshold value for the quality and determining if the frame is qualified and included, or unqualified and excluded, in the set for further processing; and the parameter comprises the threshold value, such the multiple parameter values comprise multiple threshold values, and such that varying the multiple threshold values corresponds with varying the frames which are qualified and included, or unqualified and excluded, from the set for further processing in providing the post-processed MRS spectrum.

According to one further embodiment, the quality comprises a confidence estimating a water peak location.

According to another further embodiment, the quality comprises a frequency error of a water peak location relative to a reference frequency.

According to another further embodiment, the quality comprises an amplitude of a water peak.

According to another further embodiment, the quality comprises a full width half max (FWHM) of a water peak.

According to another mode, the processing step comprises frame editing by comparing a quality value for a quality of each frame against a threshold value for the quality and determining if the frame is qualified and included, or unqualified and excluded, in the set for further processing, and also comprises bypassing frame editing if a number of qualified frames is below a threshold number; and the parameter comprises the threshold number.

Another mode comprises: dynamically varying multiple said parameters of the processing step between multiple said parameter values according to a multi-variate matrix comprising multiple combinations of the varied parameter values for each said parameter; performing the step on the set at each combination of parameter values and providing said multiple processed results, respectively, comprising said multiple respective feature values, respectively; determining the chosen feature value among the multiple feature values based upon the comparison and corresponding to a chosen combination; and providing the post-processed MRS spectrum by running the step on the set with the multiple parameters assigned to the chosen combination of respective parameter values.

According to one embodiment of this mode, the multiple parameters comprise multiple frame editing criteria for qualifying and including, or unqualifying and excluding, frames from the set for further processing steps to provide the post-processed MRS spectrum.

Another aspect of the present disclosure is also a method for processing a set of multiple serially acquired magnetic resonance spectroscopy (MRS) free induction decay (FID) frames from a multi-frame MRS acquisition series from a region of interest (ROI) in a subject, and for providing a post-processed MRS spectrum. The method according to this aspect comprises:

providing a first post-processed MRS spectrum;
identifying a feature of a downfield region of the spectrum that is located downfield along a larger part per million (ppm) range than a water peak location;
comparing the feature with a reference;
performing a processing operation based on the comparison and related to the post-processed MRS spectrum.

According to one mode of this aspect, the identified feature comprises a downfield peak region of the downfield region.

According to another mode, the comparison comprises comparing the downfield peak region against an upfield peak region of an upfield region of the spectrum located along a smaller ppm range than a water peak location.

According to another mode, the processing operation comprises adjusting the upfield region based on the comparison.

According to one embodiment of this mode, the adjusting comprises reducing at least a portion of the upfield region by a subtraction operation based upon the comparison.

According to another mode, the comparison comprises mapping a reflection of the downfield region around a center line against the upfield region.

According to one embodiment of this mode, the center line is located at about the water peak location.

According to another embodiment, the comparison further comprises adjusting the center line to an offset relative to the water peak location to correspond with an optimum correlation between at least a portion of the reflected downfield region and a corresponding portion of the upfield region:

According to a further embodiment, the center line adjustment is performed within a range of offset.

Another embodiment comprises baseline correcting the reflected downfield and upfield regions, respectively, and subtracting the baseline corrected reflected downfield region from the baseline corrected upfield region.

According to another mode of the present aspect, the processing operation comprises qualifying the post-processed MRS spectrum based upon the identified feature.

Another mode comprises adjusting a water suppression parameter of the MRS acquisition based upon the comparison.

Another aspect of the present disclosure is also a method for processing a set of multiple serially acquired magnetic resonance spectroscopy (MRS) free induction decay (FID) frames from a multi-frame MRS acquisition series from a region of interest (ROI) in a subject, and for providing a post-processed MRS spectrum. The method according to this aspect comprises:

determining a frequency shift error of an FID frame by performing spectral cross-correlation between the FID frame and a reference frame.

One mode of this aspect comprises shifting the FID frame by the frequency shift error so as to increase coherence of the FID frame with the reference spectrum.

Another mode comprises forming the reference spectrum by averaging multiple FID frames from the acquisition series.

Another mode comprises: performing an initial frequency shift error correction operation by estimating a frequency shift error for each FID frame of the series by determining a location of a water peak by locating maximum peak value in a range around an expected location for the water peak, calculating a difference between the determined location and the expected location, and adjusting the FID frame by the difference; and averaging the respectively shifted FID frames to form the reference spectrum.

According to another mode, the determining is performed on each FID frame of the series.

According to another mode, the series comprises first and second groups of FID frames, the FID frames of the first group comprise a first phase, and the FID frames of the second group comprises a second phase, and the determining is performed on each FID frame for each group separately from the other group.

According to another mode, the reference frame comprises another FID frame from the series.

Another mode comprises: comparing the frequency shift error against a threshold value; and qualifying and including, or disqualifying and excluding, the FID frame from the set for further processing to provide the post-processed MRS spectrum based upon the comparison.

Another aspect of the present disclosure is also a method for processing a set of multiple serially acquired magnetic resonance spectroscopy (MRS) free induction decay (FID) frames from a multi-frame MRS acquisition series from a region of interest (ROI) in a subject, and for providing a post-processed MRS spectrum. The method according to this aspect comprises adjusting a phase of an FID frame by a phase shift configured to reduce an extent of the absorption spectrum having a negative value.

One mode of this aspect further comprises performing at least one of a golden section search and a parabolic interpretation to compute a fast fourier transform (FFT) on the FID frame within an iteration loop.

Another aspect of the present disclosure is also a method for processing a set of multiple serially acquired magnetic resonance spectroscopy (MRS) free induction decay (FID) frames from a multi-frame MRS acquisition series from a region of interest (ROI) in a subject, and for providing a post-processed MRS spectrum. The method according to this aspect comprises: estimating a line width between two opposite walls of a water peak region of an FID frame of the series; comparing the estimated line width against a threshold value; and qualifying and including, or disqualifying and excluding, the FID frame from the set for further processing to provide the post-processed MRS spectrum based at least in part upon the comparison.

According to one mode of this aspect, the line width comprises a full width half max (FWHM) of the water peak region.

Another mode comprises: calculating an average FWHM for the included FID frames; comparing the average FWHM against an average threshold value; and assigning a quality indicator to the post-processed MRS spectrum based upon the comparison.

Another mode comprises adjusting a water suppression parameter based upon the comparison.

According to another mode, the water suppression parameter comprises water suppression bandwidth.

According to another mode, the water suppression parameter comprises a degree of water suppression.

Another mode further comprises determining the threshold value based upon a tesla strength of an MRS system from which the MRS acquisition series was acquired.

Another aspect of the current disclosure is also a method for processing a set of multiple serially acquired magnetic resonance spectroscopy (MRS) free induction decay (FID) frames from a multi-frame MRS acquisition series from a region of interest (ROI) in a subject, and for providing a post-processed MRS spectrum. The method according to this aspect comprises:

associating first and second groups of FID frames within the set with first and second different relative phases, respectively, of a phase step cycle along the MRS acquisition series;

processing the first and second groups separately;

averaging the first and second groups separately to form first and second average interim spectra; and averaging the first and second average interim spectra.

One mode of this aspect comprises performing at least one of phase shift correction, frame editing, and frequency shift correction separately for the first and second groups.

Another mode comprises performing the method on a number equal to N groups of FID frames, the FID frames comprising similar phasing within each group but different than in other groups, processing each of the N groups separately, averaging the FID frames separately within each group, averaging the group averages together, and wherein N equals an integer more than two.

According to one embodiment of this mode, the MRS acquisition series comprises a number F of FID frames, the different relative phases comprise a unique number S of phase steps, and F divided by S equals N, wherein N comprises a whole number.

Another aspect of the present disclosure is also a method for processing a set of multiple serially acquired magnetic resonance spectroscopy (MRS) free induction decay (FID) frames from a multi-frame MRS acquisition series from a region of interest (ROI) in a subject, and for providing a post-processed MRS spectrum. The method according to this aspect comprises:

generating a first baseline estimate using a rank order filter (ROF) on a range of interest of an interim MRS spectrum partially post-processed from the set;

fitting a polynomial to at least a portion of the first baseline estimate to generate a baseline curve; and subtracting the baseline curve from the interim MRS spectrum to provide the post-processed MRS spectrum.

One mode of this aspect also comprises determining first and second regions of the first baseline estimate to be included and excluded, respectively, for the polynomial fit; and fitting the polynomial to only the first regions of the baseline estimate.

Another aspect of the present disclosure is a method performed according to any one of claims 1 to 50 using a processor.

One mode of this aspect further comprises controlling the processor to perform said one or more of said methods using a computer program stored in a non-transitory computer readable medium.

Another aspect of the present disclosure comprises performing one or more of the methods elsewhere herein described, wherein: the ROI comprises a portion of a musculoskeletal joint.

According to one mode of this aspect, the joint comprises a skeletal joint.

According to one embodiment of this mode, the skeletal joint comprises a spinal joint.

According to another further embodiment, the ROI comprises at least a portion of an intervertebral disc.

Another aspect of this disclosure comprises performing any one or more of the methods elsewhere described herein, wherein said MRS acquisition series is acquired from a single voxel positioned within the ROI according to a single voxel spectroscopy pulse sequence Another aspect of this disclosure also comprises performing any one or more of the methods elsewhere described herein, wherein said MRS acquisition comprises a multi-voxel spectroscopy acquisition comprising multiple said MRS acquisition series corresponding to each said voxel, and performing the method on each said MRS acquisition series.

Another aspect of the present disclosure also comprises performing any one or more of the methods described elsewhere herein, and further comprising: providing an MRS scanner system; and acquiring the MRS acquisition series using the MRS scanner system on the subject.

Another aspect of the present disclosure comprises one or more non-transitory computer readable media comprising computer instructions configured to cause one or more computer processors to perform actions comprising one or more of the methods described elsewhere herein:

Another aspect of the present disclosure comprises one or more non-transitory computer readable media comprising computer instructions configured to cause one or more computer processors to perform actions comprising one or more of the methods described elsewhere herein.

Another aspect of the present disclosure is a method for processing a set of multiple serially acquired magnetic resonance spectroscopy (MRS) free induction decay (FID) frames from a multi-frame MRS acquisition series from a region of interest (ROI) in a subject, and for providing a post-processed MRS spectrum. The method according to this aspect comprises performing a combination of at least two of the following:

performing the step on the set at each of the multiple parameter values and providing multiple processed results, respectively, comprising multiple respective feature values, respectively, comparing the feature values of the processed results, determining a chosen feature value among the multiple feature values based upon the comparison and corresponding to a chosen parameter value, setting the parameter to the chosen parameter value for performing the processing step to provide the post-processed MRS spectrum;

providing a first post-processed MRS spectrum, identifying a feature of a downfield region of the spectrum that is located downfield along a larger part per million (ppm) range than a water peak location, comparing the feature with a reference, performing a processing operation based on the comparison and related to the post-processed MRS spectrum;

determining a frequency shift error of an FID frame by performing spectral cross-correlation between the FID frame and a reference frame;

adjusting a phase of an FID frame by a phase shift configured to reduce an extent of the absorption spectrum having a negative value.

estimating a line width between two opposite walls of a water peak region of an FID frame of the series, comparing the estimated line width against a threshold value, and qualifying and including, or disqualifying and excluding, the FID frame from the set for further processing to provide the post-processed MRS spectrum based at least in part upon the comparison;

associating first and second groups of FID frames within the set with first and second different relative phases, respectively, of a phase step cycle along the MRS acquisition series, processing the first and second groups separately, averaging the first and second groups separately to form first and second average interim spectra, and averaging the first and second average interim spectra; and generating a first baseline estimate using a rank order filter (ROF) on a range of interest of an interim MRS spectrum partially post-processed from the set, fitting a polynomial to at least a portion of the first baseline estimate to generate a baseline curve, and subtracting the baseline curve from the interim MRS spectrum to provide the post-processed MRS spectrum.

Another aspect of the present disclosure comprises one or more non-transitory computer readable media comprising computer instructions configured to cause one or more computer processors to perform actions comprising one or more of the methods described elsewhere herein:

One further mode of each of the various aspects noted above, and combinations therebetween, comprises a magnetic resonance (MR) system comprising a magnet. According to one embodiment, a controller is provided for controlling the magnet to conduct an MR exam of a patient. According to another further embodiment, the controller is configured to run a pulse sequence to actuate the magnetic to induce a pulsatile magnetic field in an area corresponding with a patient or tissue, such as according to certain pulse sequence aspects disclosed herein and/or other pulse sequence embodiments as may be contemplated by one of ordinary skill to the extent consistent with this disclosure. Further to this embodiment, the pulsatile magnetic field induced by the pulse sequence is configured to invoke a tissue response, unique to the induced pulsatile magnetic field, in a region of interest of the tissue designated for evaluation. The tissue response uniquely invoked by the induced pulsatile magnetic field generates signals along a frequency spectrum which emanate from the region of interest and are captured by an antenna receiver coil also provided in spatial relation to the region of interest. The signals of the invoked tissue response comprise unique frequency components corresponding with unique respective chemical constituents in the region of interest of the tissue. Accordingly, the spectrum of frequency response components invoked in the region of interest provides MRS information related to the tissue chemistry in that region. In a further embodiment, the region of interest comprises at least a portion of an intervertebral disc. In still a further embodiment, a voxel is prescribed to correspond with the region of interest and used to determine where spatially the induced and acquired MRS spectrum information is to correspond.

According to another further mode of each of the various aspects noted above, a non-transitory computer readable medium encoded with a computer program, and configured to be run by a processor, is provided. According to one embodiment of this mode, a processor configured to run the computer program is also provided. According to still a further embodiment, the program run by the processor comprises at least one of the MRS signal processing aspects herein disclosed, such as for example channel selection, phase correction, frame editing, frequency shift correction, apodization, baseline correction, downstream artifact correction, metabolite range measurement, and diagnostic interpretative processing.

Each of the foregoing aspects, modes, embodiments, variations, and features noted above, and those noted elsewhere herein, is considered to represent independent value for beneficial use, including even if only for the purpose of providing further combination with others, and whereas their various combinations and sub-combinations are further contemplated aspects also of independent value for beneficial use, as may be made by one of ordinary skill based upon a thorough review of this disclosure in its entirety.

Other aspects not specifically described above are also contemplated as made clear in the detailed description below. For example, additional aspects of the present disclosure comprises respective methods corresponding with manufacturing and using the systems and devices described in these aspects above, and in the description below—as would be apparent to one of ordinary skill. In addition, further more detailed modes, embodiments, features, and variations of such aspects described above and below are also herein contemplated.

BRIEF DESCRIPTION OF THE DRAWINGS

These and other features, aspects, and advantages of the present disclosure will now be described with reference to the drawings of embodiments, which embodiments are intended to illustrate and not to limit the disclosure.

FIGS. 1-43C are variously described in the detailed description provided below.

FIG. 1 shows a schematic flow chart for certain steps of a method aspect of the current disclosure.

FIG. 2 shows a schematic flow chart for certain steps of another method aspect of the disclosure.

FIG. 3 shows a schematic flow chart for certain steps of another method aspect of the disclosure.

FIG. 4 shows a diagrammatic illustration of a peak and with respect to certain features thereof, as reference to certain aspects of the present disclosure.

FIG. 5 shows a residual water full bandwidth (BW) half amplitude by frame, also referred to as full width half max (FWHM), for a 192 frame acquisition, and also shows a frame editing threshold such that frames with FWHM above the threshold are excluded.

FIG. 7A shows a residual water full BW half amplitude by frame plot for the same serial frame MRS acquisition in the lumbar disc of FIGS. 6A-D, similar to the plot shown in FIG. 6A, but in a process according to another embodiment applying a different lower threshold criteria to edit out more, and retain less qualified, frames.

FIG. 7B shows a similar time-intensity plot to that shown in FIG. 6B, but for the acquisition shown in FIG. 7A.

FIG. 7C shows a similar time-intensity plot to that shown in FIG. 6C, but for the acquisition shown in FIG. 7A and after frame editing and frequency correction.

FIG. 7D shows the spectrum for the same acquisition featured in FIGS. 7A-C, after frame editing and phase and frequency adjustment of retained qualified frames, according to another example embodiment.

FIG. 8A shows a plot for confidence of frequency estimate for each frame along the same 192 frame serial MRS acquisition featured in FIGS. 6A-7D, against which a threshold value of 0.5 (not shown) is applied such that frames must be below the threshold to be qualified and retained for further processing (unless editing is bypassed).

FIG. 8B shows a similar time-intensity plot to that shown in FIG. 7B, but for the acquisition shown in FIG. 8A.

FIG. 8C shows a similar time-intensity plot to that shown in FIG. 7C, but for the acquisition shown in FIG. 8A and after frame editing and frequency correction according to the thresholds and operating parameters of the example featured in this series of FIGS. 8A-D.

FIG. 8D shows the spectrum for the same acquisition featured in FIG. 8C, after frame editing and phase and frequency adjustment of retained qualified frames, according to another example embodiment.

FIG. 9A shows a plot for confidence of frequency estimate for each frame similar to that shown in FIG. 8A and for the same acquisition featured in FIGS. 6A-8D, but with a threshold criteria of 0.2 (not shown).

FIG. 9B shows a similar time-intensity plot to that shown in FIG. 8B.

FIG. 9C shows a similar time-intensity plot to that shown in FIG. 9C, and after frame editing and frequency correction according to the thresholds and operating parameters of the example featured in this series of FIGS. 9A-D.

FIG. 9D shows the spectrum similar to that shown in FIG. 8D, but reflecting the retained frames shown in FIG. 9C after frame editing and phase and frequency adjustment of retained qualified frames according to the different threshold criteria of this example.

FIG. 10 shows a post-processed spectrum from a lumbar disc spectroscopy exam, prior to baseline correction, in full spectrum range view.

FIG. 11 shows an input spectrum according to an illustrated downfield artifact correction embodiment of Example 1, and shows water peak and suppression side-lobe artifacts marked.

FIG. 15 shows a further progressed stage of Example 1, showing the spectrum and baseline corrected spectrum in overlay, full spectrum range.

FIG. 16 shows the mirrored spectrum in overlay with baseline corrected mirrored spectrum of Example 1, full spectrum range.

FIG. 17 shows aligned baseline corrected up-field and mirror down-field spectra, in zoomed metabolite range.

FIG. 18 shows adjusted up-field spectrum using baseline corrected spectrum, zoomed metabolite range.

FIG. 19 shows aligned up-field and mirror down-field spectra in overlay according to a further embodiment under Example 1, without baseline correction, in zoomed metabolite range.

FIG. 36 shows an x-y plot of input versus reflected input ("tupnI") data points from an acquisition to validate the mirroring function (as mirrored around point or "bin" 9).

FIG. 37 shows another x-y plot of input versus reflected input data points from an acquisition for similar validation as demonstrated in the FIG. 36 plot, although showing a calculated reflection center equal to about 12 in the particular example shown.

FIG. 38 shows a spectrum from a lumbar disc acquisition in overlay between two different aggregated phase groups from a 2-step phase cycled MRS acquisition series, and average between them.

FIG. 39 shows a flow diagram of an automated method to perform frequency shift estimation and correction, and frame selection in the context of phase group processing.

FIG. 43C shows a frame editing panel comprising the water signal analyses similar to that shown in FIG. 42C, and on the same acquisition featured in FIG. 42C, but related to the different frame editing and frequency correction thresholds and related processing featured in FIGS. 43A-B.

DETAILED DESCRIPTION OF THE PREFERRED EMBODIMENTS

This disclosure relates to the following co-pending US patent applications, which were previously filed and incorporated herein in their entirety by reference thereto: US 2008/0039710, US 2009/00300308, US 2011/0087087 (U.S. Ser. No. 12/579,371 to Peacock et al., filed Oct. 14, 2009).

This disclosure relates to the following co-pending Published PCT Patent Applications, which were previously filed and incorporated herein in their entirety by reference thereto: WO 2006/081471, WO 2007/035906, WO 2011/047197 (International Patent Application No. PCT/US2010/052737 to Peacock et al., filed 14 Oct. 2010).

Many alternative embodiments of the present aspects may be appropriate and are contemplated, including as described in these detailed embodiments, though also including alternatives that may not be expressly shown or described herein but as obvious variants or obviously contemplated according to one of ordinary skill based on reviewing the totality of this disclosure in combination with other available information. For example, it is contemplated that features shown and described with respect to one or more particular embodiments, may also be included in combination with another embodiment even though not expressly shown and described in that specific combination.

For purpose of efficiency, where reference numbers may be used in the Figures, they may be repeated between the Figures where they are intended to represent similar features between otherwise varied embodiments, though those features may also incorporate certain differences between embodiments if and to the extent specified as such or otherwise apparent to one of ordinary skill.

Figure 1:
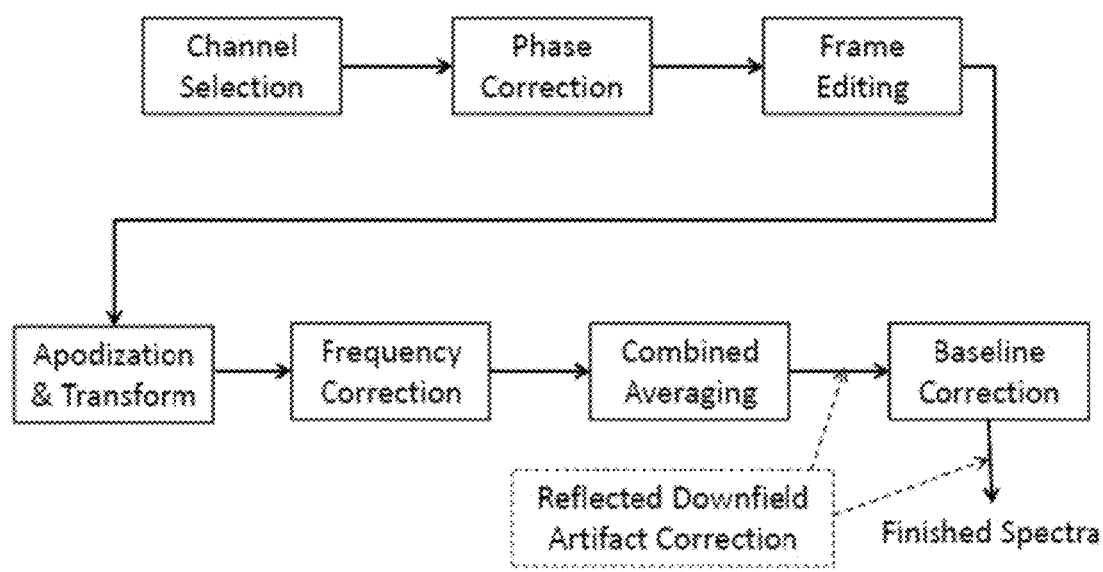
Figure 2:
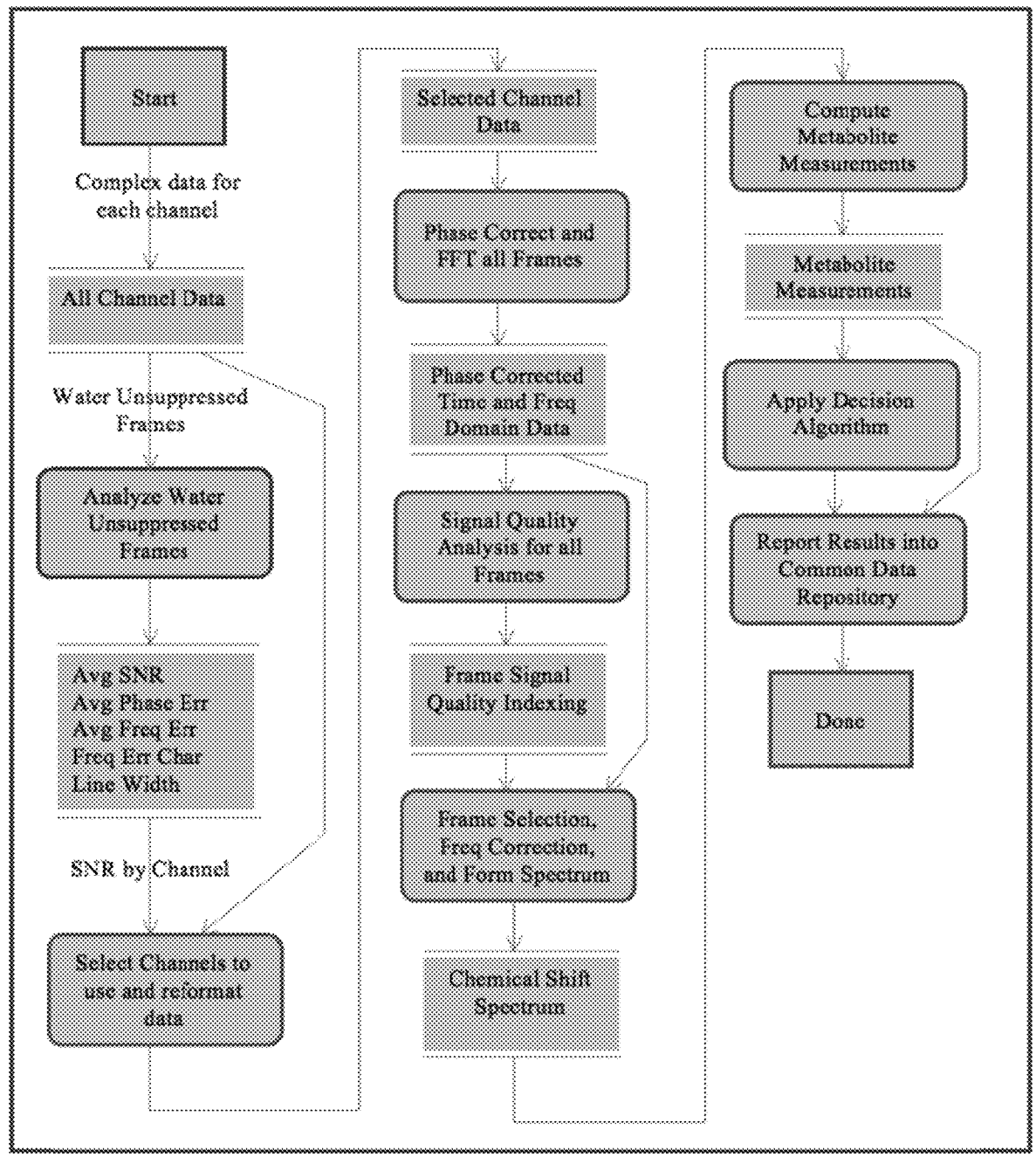

Various aspects of the present disclosure principally relates to a magnetic resonance spectroscopy (MRS) pulse sequence and/or related post-processing system and method. One aspect accordingly combines the detailed embodiments, either individually or in combination with one or more others, into an overall system. One such system and method contemplated according to one aspect of this disclosure is shown in FIG. 1. This approach is considered highly beneficial and includes channel selection via a channel selector, phase correction via a phase corrector, frame editing via a frame editor, apodization via an apodizer, transformation via a transformer, frequency correction via a frequency corrector, and combined averaging via a combiner. In addition, further embodiments also include in one regard a baseline correction via a baseline corrector, and in another regard reflected downfield artifact correction via another appropriately deployed corrector. An additional detailed embodiment is shown in FIG. 2, which further illustrates the flow of MRS signal processing according to these system components, and further downstream aspects applying post-processed spectral results to spectral measurement and diagnostic interpretive processing, as consistent with that particular embodiment. Additional particularly beneficial present embodiments of these various aspects of the present disclosure are further described in varying detail below as follows.

I. Phase Correction

One aspect of the present disclosure provides an improved automatic phase correction approach for MRS signal post-processing. This provides certain perceived benefits versus other approaches previously described and used, in particular at least one such prior disclosure based on fitting a polynomial, typically a first order or linear, to the phase sequence and then determine the time-zero intercept point which would be taken as the zero-order phase error. The phase correction approach, according to both prior disclosures and the present embodiment, are configured to generally operate on the unsuppressed water FID or on the averaged set of time domain complex free induction decay (FID) frames.

The present phase correction approach is configured to analyze the absorption spectrum and use an optimization approach to maximize or otherwise increase the real part of the absorption spectrum. Such optimization is satisfied by relative enhancements or increases, and does not require reaching a true optimum value. This automatically performs a similar function which is otherwise typically required to be done manually on MRI system consoles or other processors in post-processing MRS acquired data. The optimization approach according to the specific detailed embodiment presently described is based on using (a) a golden section search, generally described as a technique for finding the extremum (minimum or maximum) of a unimodal function by successively narrowing the range of values inside which the extremum is known to exist (see, e.g., Wikipedia description for some background), and (b) parabolic interpolation, such as available and may be used via the "MATLAB™" function called "fminbnd," as may be employed by one of ordinary skill according to the unique applications described contextually hereunder. This computes an FFT on the input data within its iteration loop, though it converges very rapidly. An objective function is to find the phase shift which reduces or minimizes the number of FFT bins in the absorption spectrum which have a negative value.

Other more complex objective functions may be employed, and have been evaluated, but generally this approach has been observed to be adequate despite its simplicity and is not significantly improved upon by more complex methods in test cases observed.

For the purpose of further illustration, the algorithm and implementation are described in the header of one exemplary source code embodiment provided below.

II. Frame Editing

Generally speaking, the frame editing process measures characteristics of each frame (a single time domain Free Induction Decay or "FID" signal). These characteristics are compared to thresholds. Frames that pass these tests are used to frequency correct previously phase corrected frames; frames that don't pass are discarded. If an insufficient number of frames pass the criteria, per an additional threshold value that may be chosen and defined, then frame editing on the whole may be discarded (as may be frequency correction also discarded, if the quality of the retained frames are not considered enabling for robust frequency correction). These frames are eventually used in aggregate resulting spectra to provide signals of sufficient signal:noise ratio (SNR) to enable quantification of the chemicals or metabolites represented in the signals. Frame editing removes "low quality" frames for the purpose of improving the SNR and, ultimately, improving the quantification of the metabolites. Frame editing is applied to all phase corrected frames prior to frequency correction as part of the "Signal Quality Analysis" block in FIG. 2. If there are sufficient frames left after editing, then frequency correction is performed.

```
function [phi, zphi, fftzph, fval, status] = optPhaseAdj(z,phiLo,PhiHi,maxIter )
% Determine the phase angle which maximizes the real part of Fourier transform
% of the complex vector, z. Search for this value between phiLo and phiHi. The
% result will be the phase error used to perform zero-order phase correction of
% an MRS FID, z.
% Algorithm: Use the MATLAB minimization function fminbnd to find the phase
% shift which minimizes the number of fft bins which have a negative value.
% The objective function simply phase shifts every sample of the input array by
% the trial value of phi, takes the FFT, and returns the count of bins below
% zero. Although simplistic, this is appears to provide an optimal (or at least improved) zero-order
% phase adjustment; this suggests that nothing would be gained by computing
% something more complex like the sum of in-phase power, though this may also be adequate
% Since the phase adjusted array and its FFT are computed and available at
% convergence, they are returned.
% Arguments:
% z    Complex vector to be phase adjusted in the MRS absorption spectrum sense
% phiLo, phiHi Search bounds, in radians for the optimum phase adjustment
% maxIter Maximum number of iterations to allow
% Returned:
% phi   Phase error, in radians, for optimal adjustment
% zphi  Phase adjusted complex vector: z with phase adjustment phi applied
% fftzph Complex spectrum of phase adjusted vector
% fval  Value of objective function
% status Convergence status
%       1 Converged to specified tolerance
%       0 Reached maximum iteration count
%       -1 Terminated by output function (see MATLAB help)
%       -2 Inconsistent bounds (phiLo > phiHi)
% 20111101 PK
% Notes:
% 1: Tolerance set to 0.01 - this was found to work well on poor SNR data,
%    converging in 10 to 15 iterations.
% 2: maxIter may vary, though start with 25.
% 3: MATLAB help warns that convergence may be slow if solution is close to
%    search boundary. In any case, if it can be given a narrower bound than -pi
%    to +pi, that will help.
status = 0;
[phi,fval,status] = ...
   fminbnd(@phaseAdjMin,-pi,pi,optimset('TolX',0.01,'MaxIter',maxIter));
   function fval = phaseAdjMin(ph )
      [Th,Rh] = cart2pol(real(z),imag(z));
      Th = Th - ph;
      [X,Y] = pol2cart(Th,Rh);
      zphi = complex(X,Y);
      fftzph = fft(zphi);
      fval = length(find(real(fftzph) < 0));
   end
fftzph = fftshift(fftzph);
end
```

Figure 3:
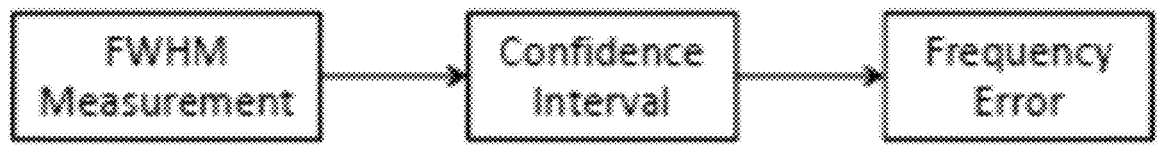

According to the present embodiment, and as shown in further flow diagram of FIG. 3, there are three frame editing modules or criteria: (1) Full Width Half Max (FWHM); (2) Confidence; (3) Frequency Error. Frames with FWHM values greater than a threshold value, confidence lower than a threshold value, or Frequency Errors greater than a threshold value, are flagged to be edited or removed from further analysis. In one further more detailed embodiment, these three thresholds values are set statically based upon empirical analysis of a test data set and as a result of non-real-time (e.g. non-dynamic relative to a given input signal) analysis of the dependency of these thresholds on the desired output; high SNR and accurate metabolite measurements. Additionally, a single set of thresholds is used for all MRS data, independent of system. The thresholds are generally set for intended optimization for the best expected performance over the expected range of MRS data, based upon historical data reviewed. However, as may also be elsewhere stated herein, descriptions related to intended optimizations, maximizations, or minimizations of certain parameters of metrics are not absolute and are not required to be fully optimum, maximum, or minimum within the intended scope of the respective disclosure where such language is used. It is contemplated that actual performance may be improved or enhanced, e.g. increased or decreased as a given desire may be, versus other options. Moreover, such performance measures even as to improvements or enhancements may not apply for every case in which the disclosed invention is put to use. The disclosed embodiments are intended to be applicable in wide use, and under variable conditions and unique considerations between cases. Accordingly, the various performance improvements or enhancements intended by various aspects of the presently disclosed embodiments may actually manifest as intended in some cases, but not others.

Full Width Half Max (FWHM) Frame Editing Criteria

Figure 4:
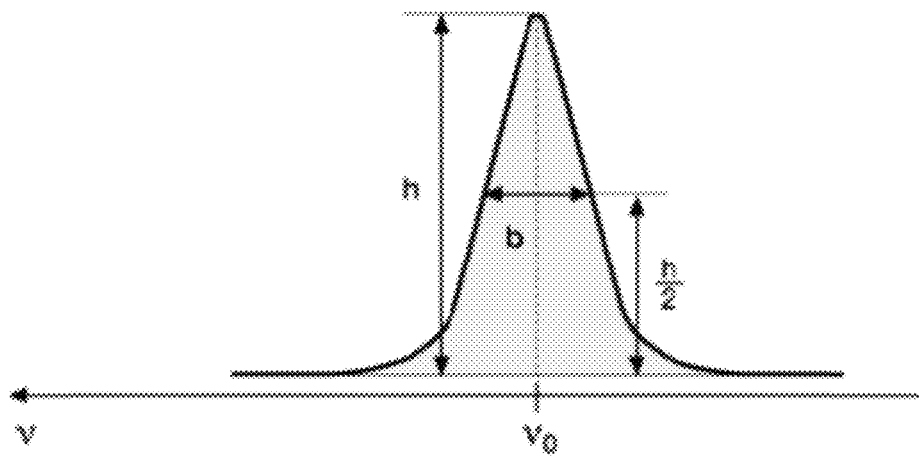

The FWHM frame editing embodiment and criteria measurement quantifies a spectral peak. More specifically, an example of FWHM is illustrated by reference to FIG. 4 (which is generally well understood in the art, though shown here as similarly illustrated in the commercial MR scanner manual available from Siemens Corporation, "SIEMENS MR Spectroscopy Operator Manual, Version syngo MR 2002B"). FIG. 4 shows spectral analysis measurements incorporated into this present embodiment, which measures the FWHM of the water signal, wherein by reference to the Figure:

v=frequency
$v_0$=frequency of interest
h=peak amplitude
b=FWHM; the peak width at half height According to one present embodiment, if the water FWHM is greater than a threshold value, then the frame is flagged to be removed (edited) from the channel. This editing step is designed to edit out relatively wide water signals, as such width has been observed to vary over the course of a multi-frame acquisition series. Such wider water signals may at certain times provide tails which can shroud adjacent chemical/metabolite peak regions of interest, and have been observed to respond unfavorably to water suppression techniques, in particular at certain times resulting in side lobe artifacts. This frame editing approach is thus configured in order to prevent such energy in the wide water signals from compromising other metabolite bands. The approach of this embodiment looks in a band around the water signal for the peak; finds the two half height points on either side of the peak, and computes the width at these points.

Figure 5:
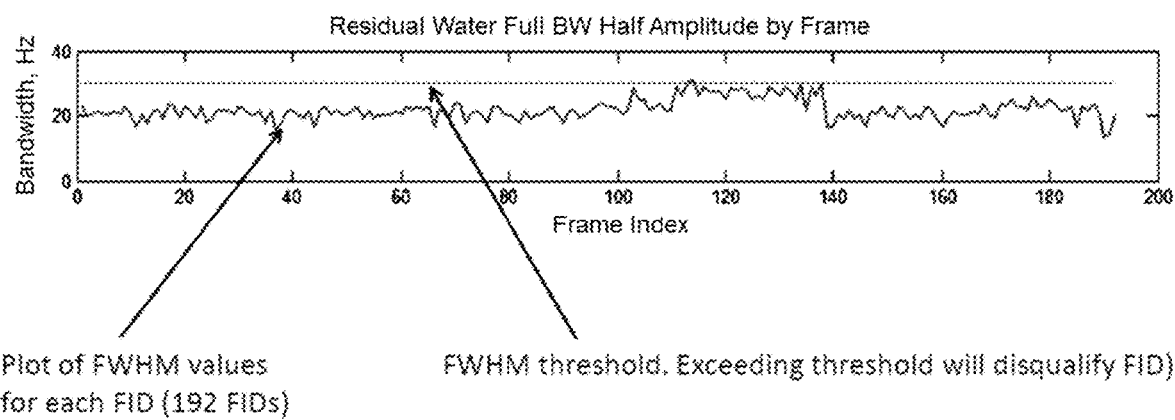

One example of this measurement taken across one illustrative multi-frame acquisition series is shown in FIG. 5. Here an editing criteria threshold value of about 30 is provided for illustration. This example (and others shown below in further illustration of the present frame editing embodiments), is illustrative of a single voxel spectroscopy (SVS) acquisition from an intervertebral disc in the lumbar spine of a human subject, acquired via a 3 T MR system and method. The exemplary threshold value of about 30 has been observed to appropriately represent a transition between generally acceptable and typically compromised spectra in a clinical test population evaluated via similar SVS acquisitions in discs.

Additional comparative examples are shown in FIGS. 6A-D and FIGS. 7A-D, respectively, for two alternative embodiments featured in relation to another additional test case, also for a 3 T SVS acquisition in a lumbar disc.

Figure 6A:
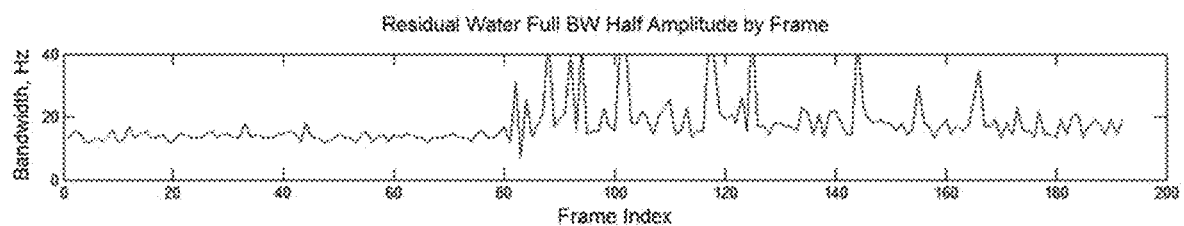
FIG. 6A shows another residual water full bandwidth half amplitude by frame plot over another 192 frame MRS acquisition from a lumbar disc, and shows a change around 80 frames into the acquisition where some frames begin demonstrating elevated FWHM bandwidth relative to a second higher threshold criteria versus that used reflected in the FIG. 5 example.
Figures 6B, 6C:
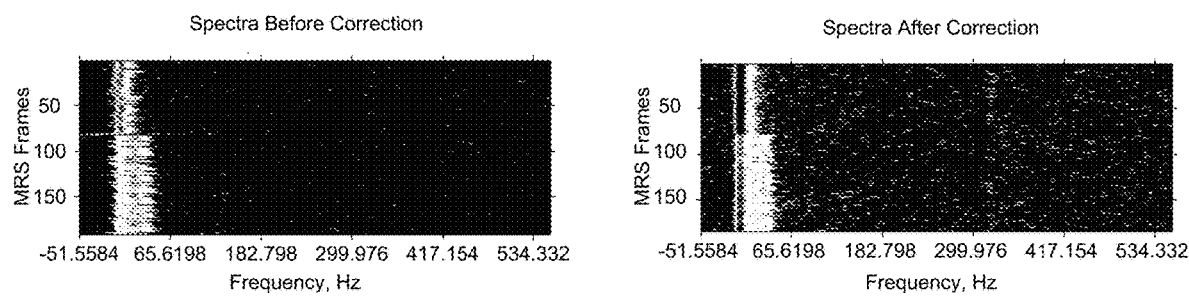
FIG. 6B shows a time-intensity plot vs. frequency for each frame in a 192 frame acquisition prior to frequency correction, where the y-axis is frames in acquisition ordered numbering (e.g. 1 to 192) moving downward vertically, and frequency range horizontally on y-axis, with each acquired spectral frame reflected as single horizontal line with spectral amplitudes reflected by contrast (brightness) value setting (higher amplitudes=lighter contrast).
FIG. 6C shows the same time-intensity plot for the same serial frame MRS acquisition shown in FIG. 6A, except after frequency shift correction on retained qualified frames performed according to one embodiment.
Figure 6D:
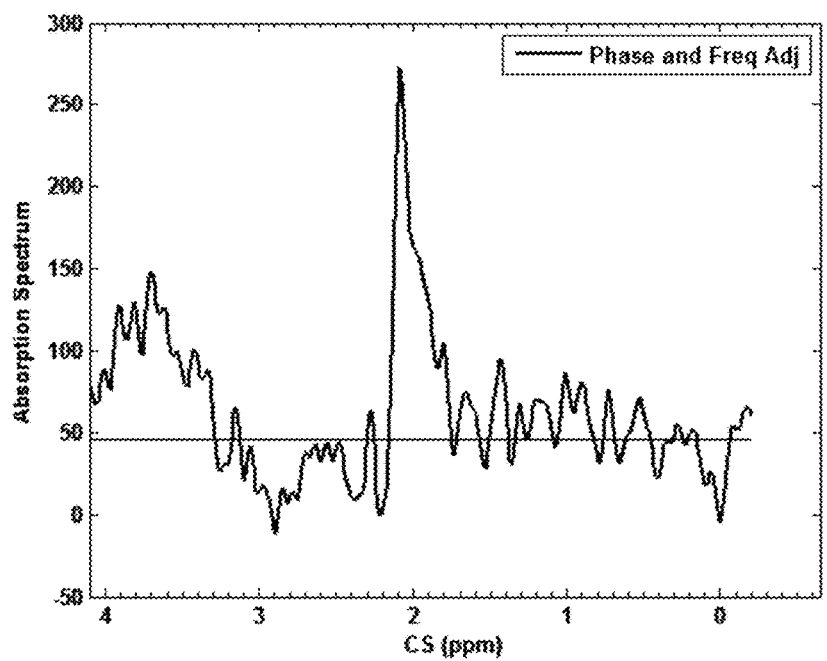
FIG. 6D shows the spectrum for the same acquisition featured in FIGS. 6A-C, after phase and frequency adjustment, according to one embodiment of the disclosure.

More specifically, FIGS. 6A-D show various aspects of one embodiment applying a FWHM threshold criterion of 50. As shown by the FWHM plot along the multi-frame SVS acquisition series in FIG. 6A, the FWHM measurement becomes regularly compromised after about 80 FID frames into the acquisition. However, due to the threshold criteria set to 50, most of these compromised frames are retained— as is shown in the time intensity plots for the acquisition pre- (FIG. 6B) and post- (FIG. 6C) frequency correction following frame editing according to this embodiment and FWHM threshold criteria. The resulting post-processed spectrum (including other post-processing modules applied consistent with other aspects of this disclosure) is shown in FIG. 6D.

For illustrative comparison, FIGS. 7A-D show similar views of the same aspects for the same SVS acquisition through the post-processing aspects revealed, but in this different embodiment a FWHM threshold criteria of 20 is applied. The result captures for selective editing/removal many more of the compromised frames with widened FWHM which exceed the threshold criteria of 20, as occur beyond the $80^{th}$ frame, than in the previous embodiment. This different result is further shown in comparing the time intensity plots of the frame data taken pre- (FIG. 7B) and post- (FIG. 7C) frame editing and frequency correction. The fully post-processed spectrum resulting according to this embodiment, and similar additional post-processing as according to the immediate preceding embodiment, is shown in FIG. 7D. This shows higher peak value, and narrower more coherent line width, for the n-acetyl (NAA) peak region around 2 ppm along the chemical shift (CS) spectrum, versus the prior embodiment applying the higher FWHM threshold criteria to the same input data and otherwise common post-processing approaches between embodiments.

Confidence Interval Frame Editing Criteria

The confidence interval is a tool used to signify the reliability of an estimate in a statistical analysis. The interval is the range in a sample distribution between which it is expected that the population value will lie, given the particular degree of confidence. The confidence interval value (CIV) for a frame reflects the confidence that the water spectral line for that frame can be identified from surrounding spectral lines. This is done by characterizing the energy (area under the curve) of the water line with respect to the region where the water line is expected.

The CIV measurement starts with determining the FWHM of the spectral peak (assumed to be water) in the center of a region. The bins (unit of integration) within the FWHM of the water spectral line define the water line energy. The number of bins in the region surrounding and including the water signal greater than bins within the FWHM is counted. The CIV is the number of bins within the water line divided by this difference, and ranges between 0 and 1. More specifically, the CIV is calculated according to the following formula:

CIV=Water line energy/Total energy in region−Water line energy

As applied according to the present embodiment, frames with relatively little energy outside the FWHM of the water line have a higher confidence than frames with relatively more energy outside this range.

A comparative example demonstrating the beneficial impact of applying such a CIV threshold criteria for frame editing is provided as follows.

FIGS. 8A-D illustrate yet another frame editing embodiment as applied to the same multi-frame SVS acquisition series from the same intervertebral disc featured in FIGS. 6A-7D. However, these current figures illustrating this present embodiment instead reveals that, during the multi-frame acquisition series, the confidence estimate for the water signal also became compromised. According to this specific embodiment, a CIV threshold of 0.5 was applied for confidence interval based frame editing. More specifically, FIG. 8A shows the confidence of the frames in the series, with significant reduction in the confidence revealed at about 80 frames into the acquisition (similarly where the FWHM measurements became compromised). However, as shown here with the CIV value threshold set to 0.5, only a few of these later compromised frames were also dropped below this threshold value and were edited for removal. Most of the compromised frames were retained. FIGS. 8B-C show time-intensity plots for the acquisition series prior to (FIG. 8B) and post (FIG. 8C) frequency correction following frame editing according to the confidence interval-based criteria at the 0.5 threshold value described. The final post-processed spectrum (also incorporating other post-processing approaches also herein described following frequency correction) is shown in FIG. 8D.

For comparison, the same acquisition series illustrated in FIGS. 8A-D is also illustrated in similar views in FIGS. 9A-D. However, these figures illustrate an alternative processing embodiment wherein the confidence interval (CIV) threshold is set to 1 (vs. 0.5 according to the immediately preceding embodiment). As shown in the confidence plot in FIG. 9A, the vast majority of the later frames with compromised confidence drop below the 1 CIV threshold after the $80^{th}$ frame. These are thus flagged and edited, with far fewer frames retained, as revealed in the time intensity plot post-frame editing shown in FIG. 9C (vs. prior to frame editing, as shown again in FIG. 9B). The final post-processed spectrum according to this embodiment is shown in FIG. 9D, and reveals are more coherent NAA peak with narrowed line width in the CS region of 2, versus the spectrum shown in FIG. 8D for the same acquisition but processed according to that preceding embodiment with the different and more forgiving CIV threshold criteria.

Frequency Error Frame Editing Criteria

The frequency error is the absolute value of the difference between where the water signal peak is located along the chemical shift spectrum and where it should be. If this difference is large then energy from the water signal can leak into and distort the metabolite peak regions of interest, and ultimately compromise robustness of the metabolic spectral range and corresponding diagnostic interpretation. Leakage is due to the finite water suppression bandwidth. Frames that exceed +/−maximum frequency error threshold criteria are flagged for removal from the series for further processing. Frames that do not exceed the +/−maximum frequency error threshold are retained and subsequently frequency corrected to improve coherence (Frequency Correction). As with other criteria, however, if insufficient frames are retained via this criteria, then according to one embodiment all frames may instead be retained and frequency correction is aborted in the overall processing regimen. However, due to the poor signal quality according to this applied criterion, the result may be flagged as potentially compromised.

Real-Time Frame Editing Optimization

Another aspect of the present disclosure provides a novel approach for optimizing frame editing criteria. This embodiment proposes enhancement to the otherwise "static" empirically derived approach described above, by providing an approach that sets the frame editing thresholds described "dynamically" in real-time based upon optimizing results for a given input signal. This provides the ability to optimize the frame editing to achieve the highest SNR and best quantification of the metabolites for each input series. Moreover, the optimization criteria may be, but do not have to be, limited to SNR.

The table below lists the range of thresholds used for optimization. The notation that defines the values is of the format; Start:Increment:Stop. The Confidence Threshold, for example takes on 3 values: 0.5, 0.6, and 0.7.

The result of these tests would be a 3×5×4×7 matrix space. The optimization search would then be to find the set of thresholds that maximized the desired metric, SNR for example.

III. Frequency Correction

Another aspect of the present disclosure is an improved approach for frequency error correction in MRS spectral signal post-processing. The following describes the processing flow and functions performed by the MRS post-processor to effect robust frequency error correction according to this present embodiment.

A primary purpose of frequency error correction is to reverse frequency shifts which occur on a frame-to-frame basis, such as for example as may occur due to subject movement or to $B_0$ variations resulting from subject respiration. Static frequency errors also occur if the MRI system was not set to correctly center the water signal to zero at the start of the series acquisition. A primary objective of post-processing frequency correction is that the residual water signal be positioned at "d.c." (or 0 Hz) in the spectrum for each frame. When the appropriately centered frames are combined by averaging, the metabolite signal components will be aligned in frequency and phase and will therefore sum coherently—or "coherent averaging." This coherent summation, post frequency correction, will often result in increased metabolite peak height and narrower linewidths. This approach minimizes signal loss due to non-coherent averaging and linewidth spread due to frequency error artifact. As the noise component is more random (relative to the signal component in the frame spectra), the frequency alignment increases the signal without similar increase in noise, thus also having the result of increased signal:noise ratio (SNR).

The approach of the present embodiment is described in further detail as follows. First, the MRS multi-frame acquisition series is prepared for frequency correction, such as for example employing one or more (or all) of the following: phase correction, channel selection, frame selection, zeropadding, and apodization. Frequency error is then estimated, to determine the frequency error for each frame. Frequency correction is then conducted to apply a correction to negate the frequency error. Coherent averaging is then conducted of the complex frequency-corrected frames, thus computing the final composite spectrum as coherently adjusted according to this novel method.

Frequency Shift Estimation

More detailed frequency estimation embodiments are described as follows. One embodiment for estimating the frequency error operates on the discrete Fourier transform absorption spectrum of each frame to determine the frequency bin representing the peak of the residual water signal. The analysis is limited to a parameter-specified range around the zero frequency point or "center bin." For one exemplary embodiment configured to work with MRS data acquired via a 3 T MR system, this range corresponds to plus and minus about 50 Hz.

In addition to determining the peak frequency of the residual water signal, several signal quality and reliability estimations are made which are used in the frame selection process to determine if the frequency error estimate is of sufficient reliability to be applied. These measures include a numerical confidence and an estimate of the linewidth defined as the full width at half amplitude, in Hz—both of the water signal observed. The result of the frequency error estimation process is a vector of error estimates, in Hz, corresponding to each FID or MRS frame.

The confidence measure according to the foregoing is computed according to another more detailed illustrative embodiment as follows. The discrete amplitude spectrum is analyzed in the range of the center-tuned frequency plus and minus a threshold value, such as for example about 40 Hz (which may be appropriate in the case of data acquired via a 3 T system, and about half that for example with respect to data acquired via a 1.5 T system). The highest peak is located within the range, and its width at the half-amplitude point is determined. Next, the total spectral width of all parts of the spectrum which exceed the half-amplitude point of the highest peak is determined. The confidence estimate is made by taking the ratio of the spectral width of the greatest peak divided by the total spectral width which exceeds the threshold. If there is only a single peak above the threshold, the confidence estimate will be 1.0. As a number of peaks or spectral components which could be confused with the greatest one increases, then the estimate will be reduced accordingly toward approaching 0.0. This provides a simple and robust estimate of the randomness or dispersal of energy in the vicinity of the water peak. Like an entropy measure, it has the desirable characteristic that its performance is generally invariant with amplitude.

An alternative approach believed to offer potentially improved performance, in particular in cases of relatively lower water signals in spectra, is based on spectral correlation. According to this approach, a complex cross-correlation sequence is computed of the complex apodized discrete fourier transform (DFT) of each FID and a reference spectrum. The reference spectrum can be that of one of the individual FIDs, or the averaged spectrum of multiple FIDs. The process uses the information inherent in all the spectral components which are common and coherent between the test spectrum and the reference to determine the spectral alignment of the two spectra. This is indicated by the location of the peak of a cross-correlation coefficient. One advantage contemplated for this embodiment, such as in some cases versus the spectral analysis approach described above, is that in the case of closely located coherent spectral artifact signals, which has been observed in some acquired spectral examples, this approach uses this artifact signal to advantage rather than it being disruptive as with spectral analysis. More specifically, the spectral analysis approach above may confuse the artifact with the water signal, decreasing confidence level. This alternative approach benefits from all correlating signals. The correlation method may also offer greater sensitivity than the spectral analysis method in certain cases, as the preceding approach exploits only the residual water signal. For example, given sufficiently strong metabolite signals, the current embodiment of spectral correlation could be used with complete water suppression. It is to be appreciated, however, that in relatively low metabolite SNR examples (such as small voxels), such metabolite signals may not be sufficient to provide this advantage in some circumstances—such that the water-based spectral analysis approach may be equivalent (or even improved in some cases). An additional advantage of the present embodiment, however, is that the correlation peaks are better behaved than spectral peaks of residual water in the presence of artifact, making peak analysis more precise. The result of this process is provided in the same format as for the spectral estimate approach.

Frequency Shift Correction

Given the frequency error estimates for each frame, such as determined by the frequency error estimate approaches described above, the correction is then applied to the data. This is done according to one present embodiment in the time domain.

According to another more detailed embodiment, this is done by multiplying complex FID data by a linear complex phase function, of unity amplitude, representing the negative of the frequency error. This is a function for which the phase increments by $(2 \cdot \pi \cdot \text{ferrHz}/\text{Fs})$ for each sample, where ferrHz is the frequency error in Hz, and Fs is the sample rate in samples per second. This has the effect of rotating the spectrum such that the measured water peak will be shifted to the zero or d.c. location. This linear function also has effect of performing a first-order phase correction across the spectrum. This frequency correction operation is applied to the frames of each acquisition (coil) channel which are to be combined.

As previously described, it is further contemplated that frequency error correction can also be conducted in the frequency domain—simply by shifting the spectra by the appropriate bins to coherently align them (e.g. via the water peak, per estimate of the bins represented by the shift error from the center point for each FID).

IV. Frame Averaging

Frame averaging is performed on coherently aligned FID frames, per the foregoing approaches. This is done according to another present embodiment in the time domain, and may be accomplished by simply averaging the selected complex frame data for each FID. This is performed for the FIDs collected from each of the channels which are to be combined. It is further contemplated according to still further embodiments that this could also be well performed in the frequency domain, though the time domain approach has been observed to be more efficient in many cases.

V. Phase Grouping

For example, another such aspect comprises processing MRS data from an acquisition series conducted across first and second phase groups comprising first and second sets of acquisition frames acquired at first and second different respective phases along a phase cycle. Further to this aspect, the system and method processes at least in part the first and second phase cycle groups separately. According to one mode of this aspect, the separate phase group processing comprises at least one of the other processing aspects, modes, embodiments, variations, and features elsewhere herein described, such as for example one or more of frequency error estimation, frame editing, frequency correction, and phase correction. According to another mode, the first and second set of acquisition frames for each phase group are combined into one phase group combined result. According to another mode, the first and second phase groups are combined to provide an averaged spectral result following the separate processing. In another mode, the first and second sets of each phase group are combined (e.g. averaged), and then the combined phase groups are combined (e.g. averaged). Another mode comprises reducing or removing artifact separately between the phase groups. In another mode, the artifact is removed by combining the phase groups after separate processing and in-group frame combining. In another mode, frame editing is performed on each phase group, and a different number of frames are retained (or conversely filtered out) in each group prior to combining in-group frames and the groups together.

Another aspect provides an MRS acquisition data set in separate phase cycle groups, and a process which is performed on each phase cycle group independently of the other. According to one mode of this aspect, the phase of certain excitation pulses in the pulse sequence are changed such that unwanted coherences will have different phases when the signal is acquired and while desired coherences will have the same phase, This is so that when the frames are combined, the artifact signals cancel and intended signals combine constructively. It is to be appreciated that such phase step cycling could be transparent to post-processors and still achieve sufficiently adequate results in many circumstances. It is also appreciated, however, that certain benefits may also be provided by integrating phase cycle grouping into post processing, such as for example to mitigate degradation of results due to artifact. According to one example embodiment for illustration, a processing approach using frame editing may result in fewer frames in one phase cycle group than in the other, versus matching them as typically intended for equally weighted averaging. By processing the frames as one overall group without regard to phase cycle grouping, the group with more frames would have a higher weighted contribution to the averaged result. This may result in a phase bias in the result with regards to unwanted signal qualities (e.g. artifact) intended to be removed by the very purpose of the phase cycling. By treating the phase cycle groups separately, and averaging them separately, their respectively averaged results contribute equal weighting to then thereafter averaging those interim results together. In addition, other processing operations such as spectral correlation may not perform as well when attempting to cross-correlate FID frames of separate phase cycle groups (due to their respective phase differences), vs. within the same phase cycle groups first.

VI. Channel Combining

The MRS acquisitions are typically collected on multiple channels representing the signals acquired from a multi-coil antenna detector array. Zero-order phase alignment and frequency correction (with or without frame editing) will have been performed for each channel, though channel selection may have been employed to reduce the channels from all which acquired signals to only those determined to be the strongest (per other embodiments contemplated). The remaining step is to combine the composite FIDs from each channel retained. This may be performed according to one approach by merely combining them into one composite average. This may suitably approach optimal results when combining channels of similar SNR. Alternatively, this may be done using a maximal-ratio combining approach, such as often employed for multi-channel radio frequency signals in communications technology. According to one illustrative detailed embodiment, considered particularly beneficial, the channel weighting factors used are based on the total power in each retained channel after apodization.

VII. Mirrored Downfield Artifact Correction in Upfield Metabolite Range

Another aspect of the present disclosure relates to signal components induced MRS spectra downfield of the water signal in the spectra. This is described by way of various particular embodiments below, including by reference to certain Examples 1-4, and corresponding Figures by reference thereto. Such induced downfield signals, when present, have been observed to co-exist with similarly located signals mirrored in the upfield side of the water signal. When present, the locations of certain of these downfield signals have been observed with appreciable regularity to roughly mirror the locations of metabolite ranges of interest upfield of water. This is particularly observed at downfield regions roughly mirroring peak locations opposite the water reference or center line corresponding with at least one of n-acetyl (NAA)(e.g. 1.9-2.3 mirrored location), lactic acid/alanine (LAAL)(e.g. 1-1.5), and lipid (e.g. 0.5-1.5) chemical regions along the spectrum. When these downfield signals are generated, they also correspond quite regularly with similarly shaped peaks generated at these respectively mirrored locations.

An exception is found in relatively discrete down field peaks that are often generated more closely downfield of water, e.g. 4.7-6.1 ppm in the CS spectrum. These induced peaks closely downfield of water have not been observed to correspond with mirrored peak signals on the corresponding closely upfield side of water (e.g. 3.3-4.7 ppm). It is believed that this closely downfield peak, when present, may correspond with one or more MRS chemical signatures unique to that location (e.g. uptake of certain pain medications may manifest in such peaks).

It is believed, based on scientific theory and also certain supporting observations (including via observations in clinical test data), that these downfield signals and corresponding mirrored upfield signals around water (e.g. beyond about 6 or 6.1 ppm, and below about 3.3 ppm, respectively, in CS spectrum) may comprise side lobes induced by applying water suppression during an applied MRS pulse sequence to, and related MRS signal acquisition from, a prescribed tissue region of interest in a patient. This would support the roughly symmetrically mirrored and similarly shaped signals on each side of water/center line. Because no appreciable chemical or metabolite signals are expected to be generated in this downfield range, the signals observed there are considered to be the downfield components of such artifact. Often the corresponding upfield peaks generated in the metabolite regions of interest have more power than these mirrored downfield peaks. However, these upfield regions are expected to comprise real, discrete chemical peaks known to correspond with the chemical constituents noted (when in tissue)—and so are expected to be additive between real signal (when present) and the reflected artifact noted.

According to the foregoing, this present aspect of the disclosure uses spectral peak artifacts induced in the downfield CS spectrum as a basis by which to adjust the upfield spectrum in a corresponding range roughly mirrored around the water peak location (about 4.7). This is done to remove suspected contributions of similarly mirrored artifact components from real induced chemical signal peak components that may be collocated in this upfield range. This is generally done by subtracting the power along the downfield range from the corresponding mirrored upfield range, as further described below. According to one mode, the downfield range contemplated is from about 6 or 6.1 ppm and beyond, and the upfield range is from about 3.3 ppm and below, for this adjustment.

Accordingly, one current embodiment captures the downfield signal, inverts it around an axis (e.g. water) to align it against the upfield spectrum, and subtracts the inverted downfield spectrum from the upfield spectrum to provide a resulting "downfield adjusted" spectrum in the upfield range. It is further recognized that the "mirroring" effect of the downfield artifact signals may not be exactly perfectly symmetrical in all cases, and so simple inversion around the water axis may not result in exact corresponding alignment between the inverted downfield artifact peaks and the upfield peaks. Among other reasons, side lobes arising from water suppression anomalies would not necessarily be perfectly symmetrical, especially via water suppression conducted via a fixed range around 4.7 ppm in the setting of an actual water signal that may not exist exactly at 4.7 (or vary about it between frames due to frequency shift and/or other anomalous influences). Accordingly, the alignment of the reflected downfield spectrum with the upfield spectrum may be further adjusted to better align the peaks—to the extent resulting in enhanced correlation, and more robust expected spectral results arising from the artificial subtraction step imparted on the originally induced spectrum.

The foregoing general description is further developed in finer detail according to the additional exemplary embodiments as follows:

More specifically, downfield (generally referring to chemical shift values greater than water; nominally 4.7 PPM) artifact spectral peak signals believed to be related to water suppression has been observed in some of the clinically acquired MRS data and observed to also correlate to similar artifact signals quasi-symmetrically located on opposite "up field" side of water in range of interest for metabolite signal regions. In particular, downfield peaks have been observed quasi-symmetrically around water to correspond with proteoglycan (PG) and lactic acid/alanine (LAAL) related regions of diagnostic interest (among other regions, as elsewhere noted herein). The purpose of the following examples is to uniquely reflect observed downfield artifact into up-field metabolite regions, and artificially apply innovative solutions to reverse and correct for this in spectral presentation and/or analysis for diagnostic purposes.

Adjustment of the up-field artifacts by the down-field spectral components, believed to be symmetrically reflected as embedded in the upfield spectral range, is conducted according to the following steps, with the adjustment process illustrated using plots for four exemplary disc studies further described below:

1. Coarse Alignment of the spectrum to DC
2. Fine Alignment of the up and down field spectral components in a specific chemical shift range
3. Baseline Correction (an optional step, and may be done prior to or after adjustment).
4. Adjustment: subtraction of the aligned down field components from the up field components in a specific chemical shift range of interest.

i. Coarse Alignment

Figure 10:
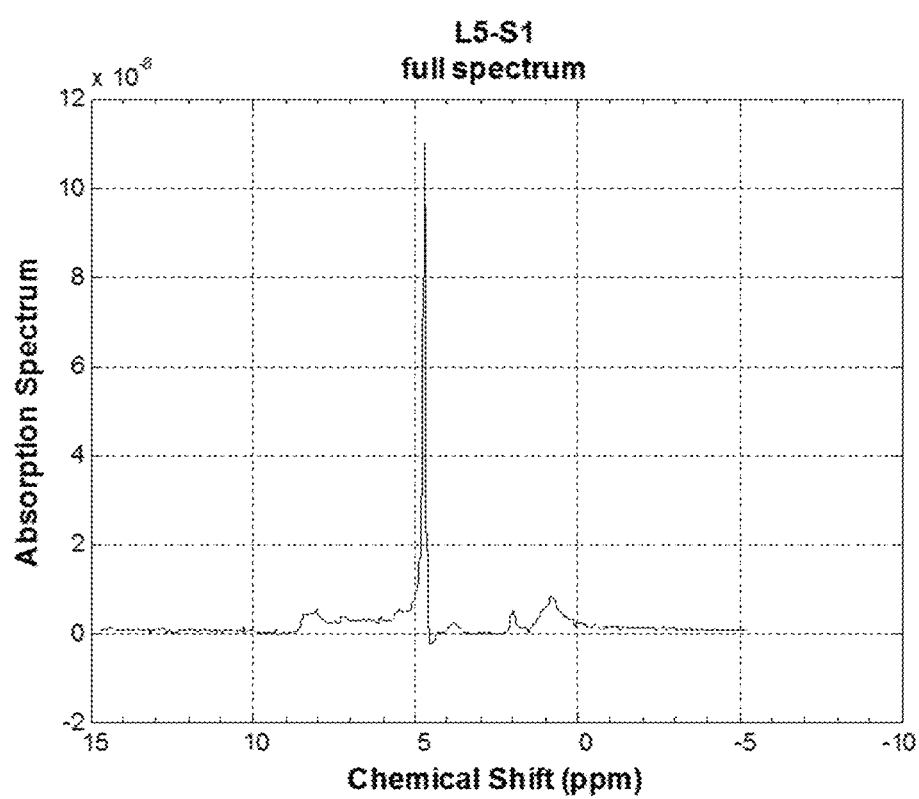

Coarse alignment of upfield and downfield spectra is performed according to one embodiment as follows. The location of the water peak is determined. This is typically the maximum peak value in the spectrum and should be located in a DC-centered spectrum at or at least very near bin 1025 (e.g. when using 2048 point FFTs). All plots shown are in terms of Chemical Shift in PPM. Water corresponds, roughly, to a chemical shift of 4.707. If the peak is not at DC then the entire spectrum is circularly rotated so that the peak is located at DC. FIG. 10 shows a chemical shift spectrum and its mirror, using water as the line of symmetry. This example shows that the computed water peak is one bin to the left of water. The mirror is then one bin to the right of water. FIG. 10 shows the input spectrum representing an initial stage of processing a first Example 1 spectrum. The input spectrum shown is post-processed according to various embodiments herein shown and described, but without baseline correction and pre-downfield artifact correction according to the current embodiments.

Figure 11:
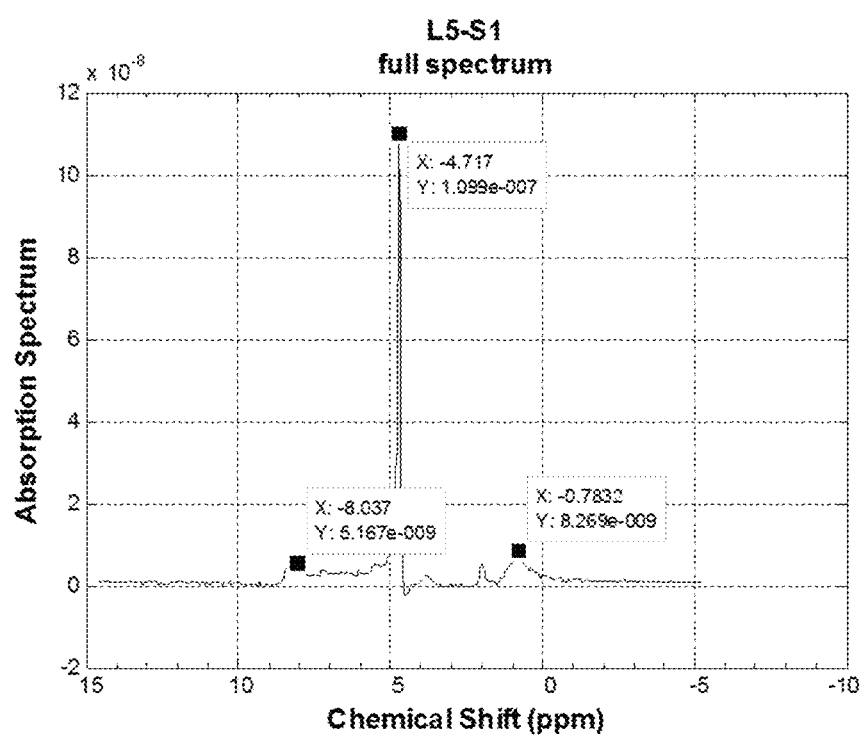

FIG. 11 is the same spectrum at same stage of processing shown in FIG. 10, but showing a broader scale of the spectrum with the water peak and downfield spectrum to its left in the graph, and with salient side lobes (which may be for example representative of water suppression artifacts) marked to illustrate that the water peak is not always at DC, and also that the water suppression artifacts are not always exactly symmetric about water. It is noted referring to FIGS. 10 and 11 that the signs of the values are negative due to the way data is plotted and the left-to-right decrease of the Chemical Shift axis. Nonetheless, spectral range to left of water is considered "downfield" whereas spectral range to right of water peak is considered "upfield" for purpose of describing these current embodiments of this disclosure.

Figure 12A:
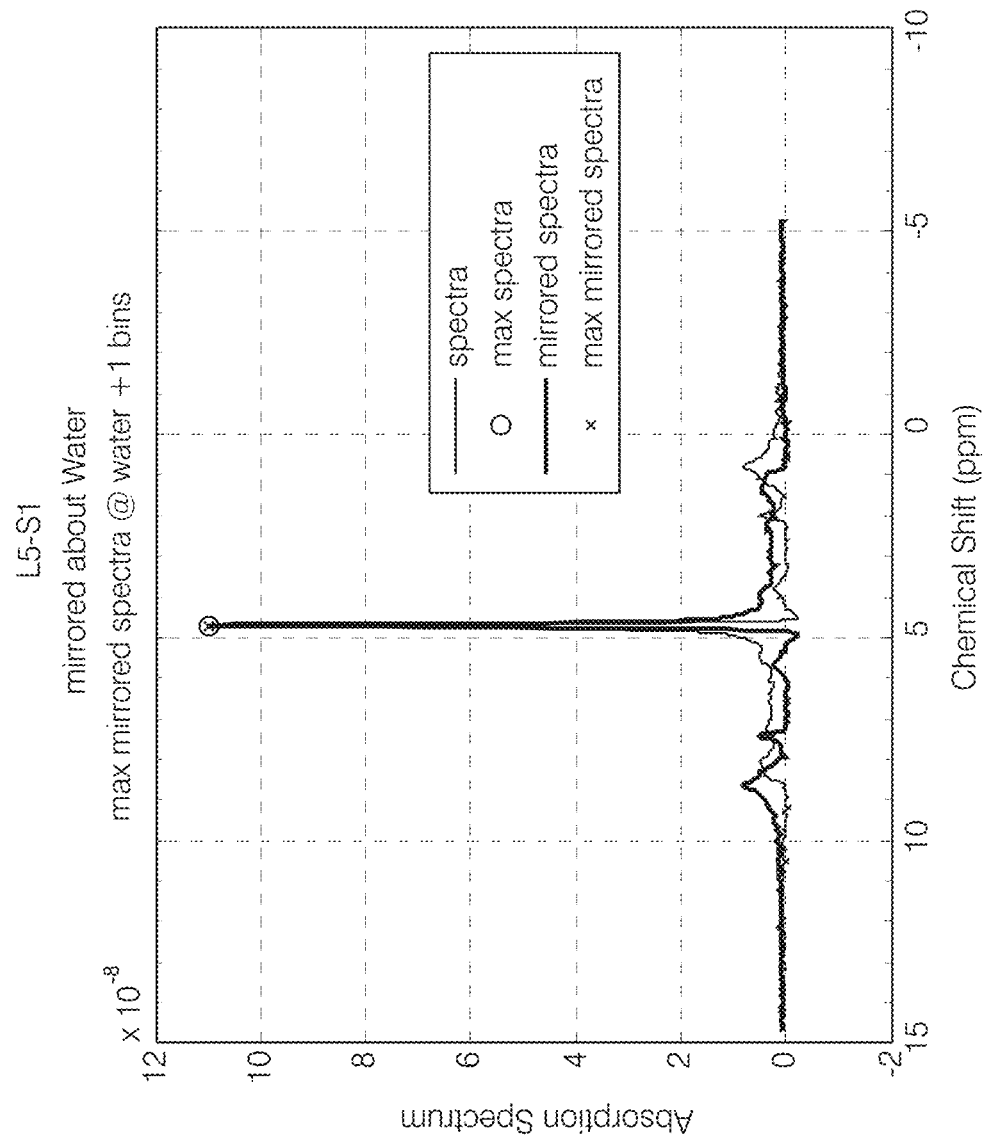
FIG. 12A shows the same input spectrum as FIG. 11, but with addition of a mirrored spectrum in overlay, full range including up and downfield spectral regions.
Figure 12B:
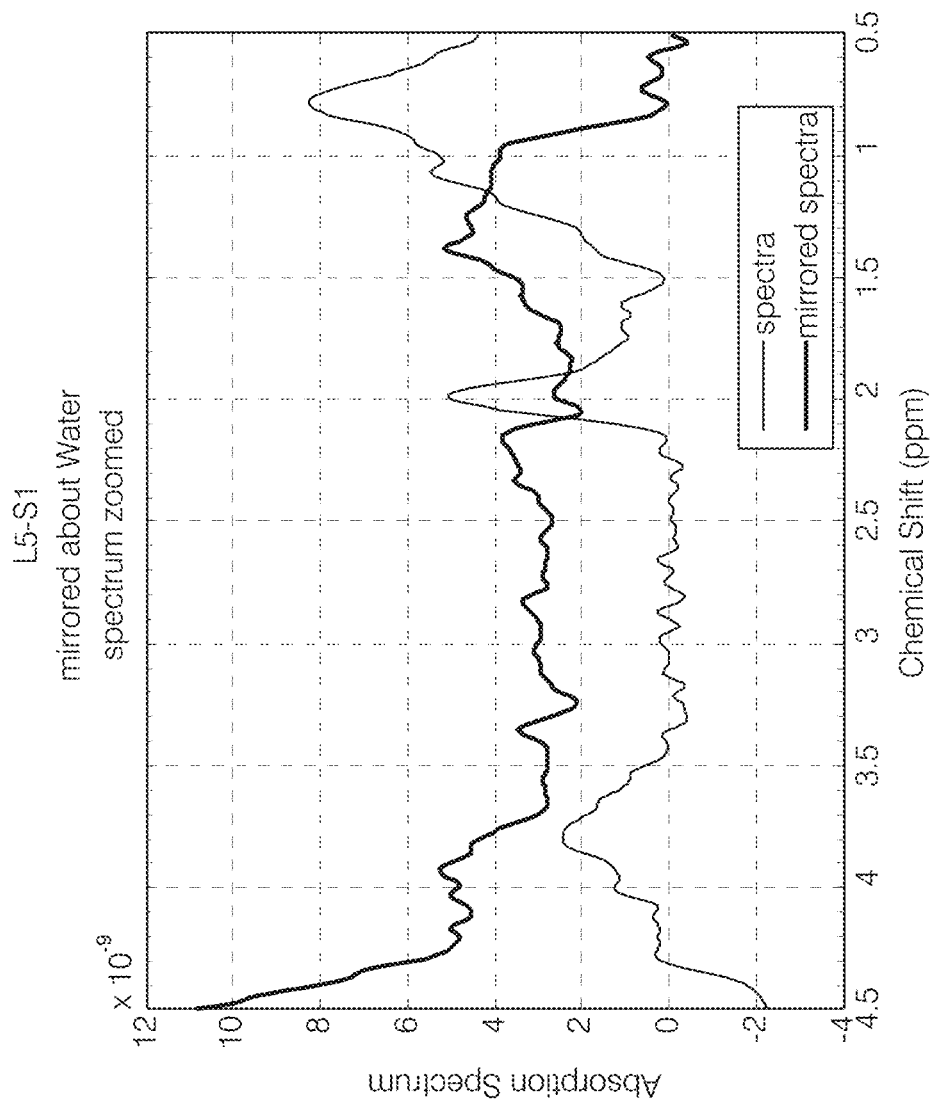
FIG. 12B shows the same input spectrum and mirrored spectrum of FIG. 12A, with offset downfield correction by 1 bin, in zoomed metabolite range.

FIGS. 12A-B show further progression of Example 1, in sequentially increasing resolution (FIG. 12B showing mainly the metabolite range of interest). This illustrates the same input spectrum and its mirror, and illustrates the 1 bin of absolute error of both signals relative to DC.

Figure 13A:
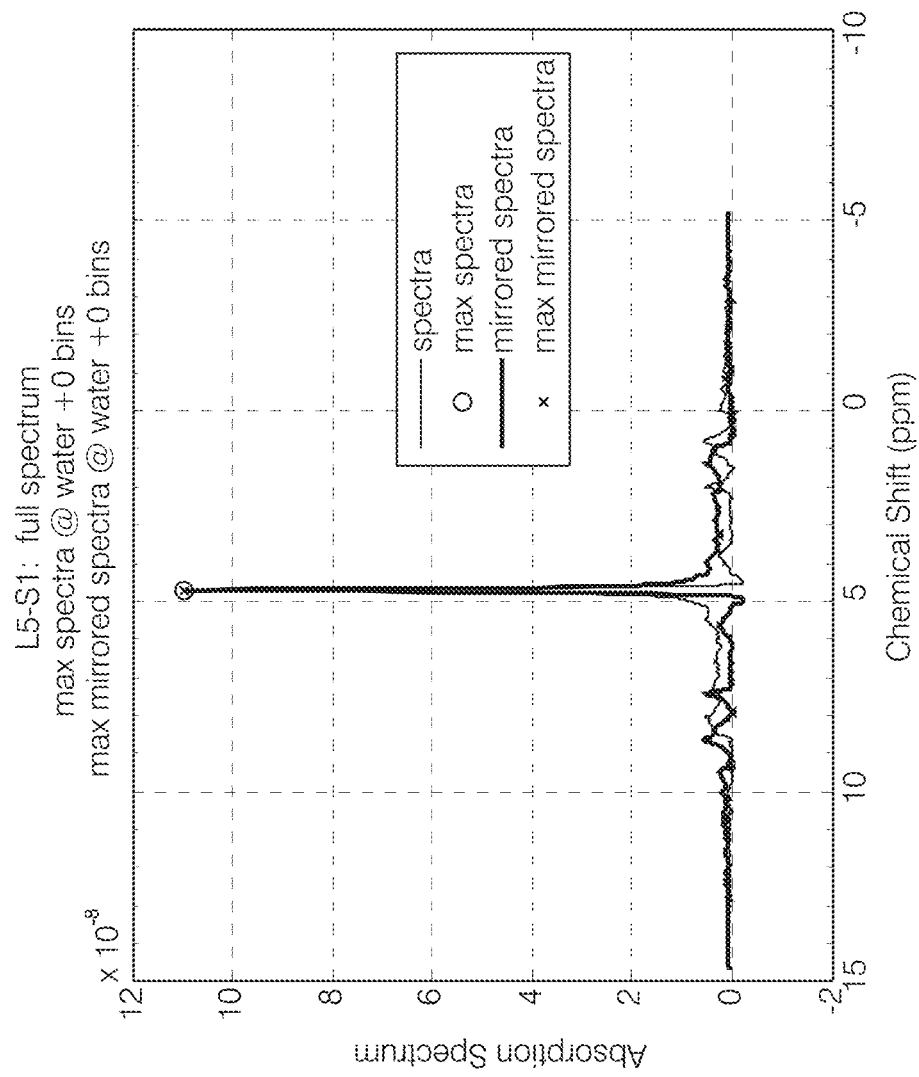
FIG. 13A shows the same spectrum of Example 1 shown in FIGS. 10-12B, but with the spectrum shifted to water and mirrored spectrum, full range.
Figure 13B:
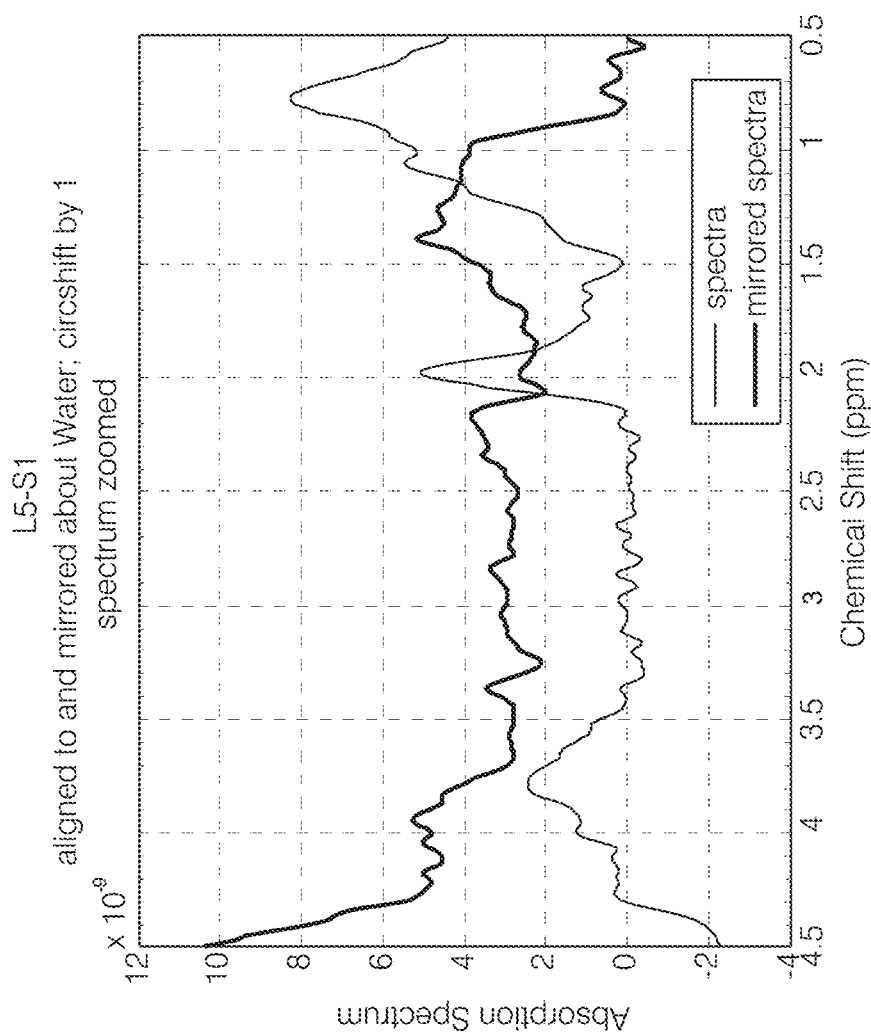
FIG. 13B shows again the same spectrum of Example 1 shown in FIG. 13A, zoomed to metabolite range of interest below 4.5 ppm on chemical shift spectrum.

FIGS. 13A-B show the spectrum circularly rotated one bin so that the computed water bin (bin with the maximum value) aligns with DC (Chemical Shift of 4.707 Ppm).

ii. Fine Alignment

Figure 14A:
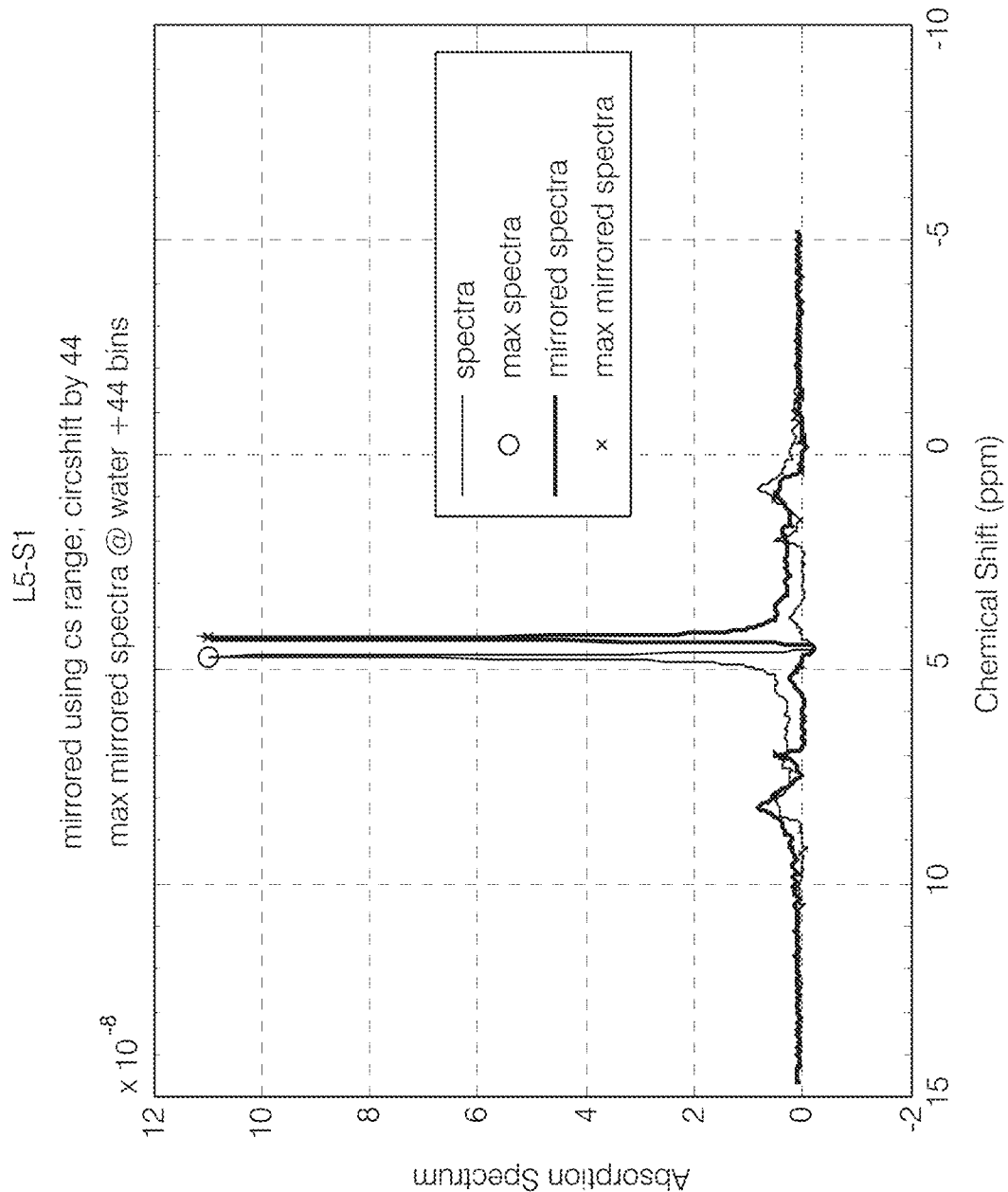
FIG. 14A shows the spectral processing in further steps under Example 1, but with fine alignment having been performed between the spectrum and mirrored spectrum, shown in full range.
Figure 14B:
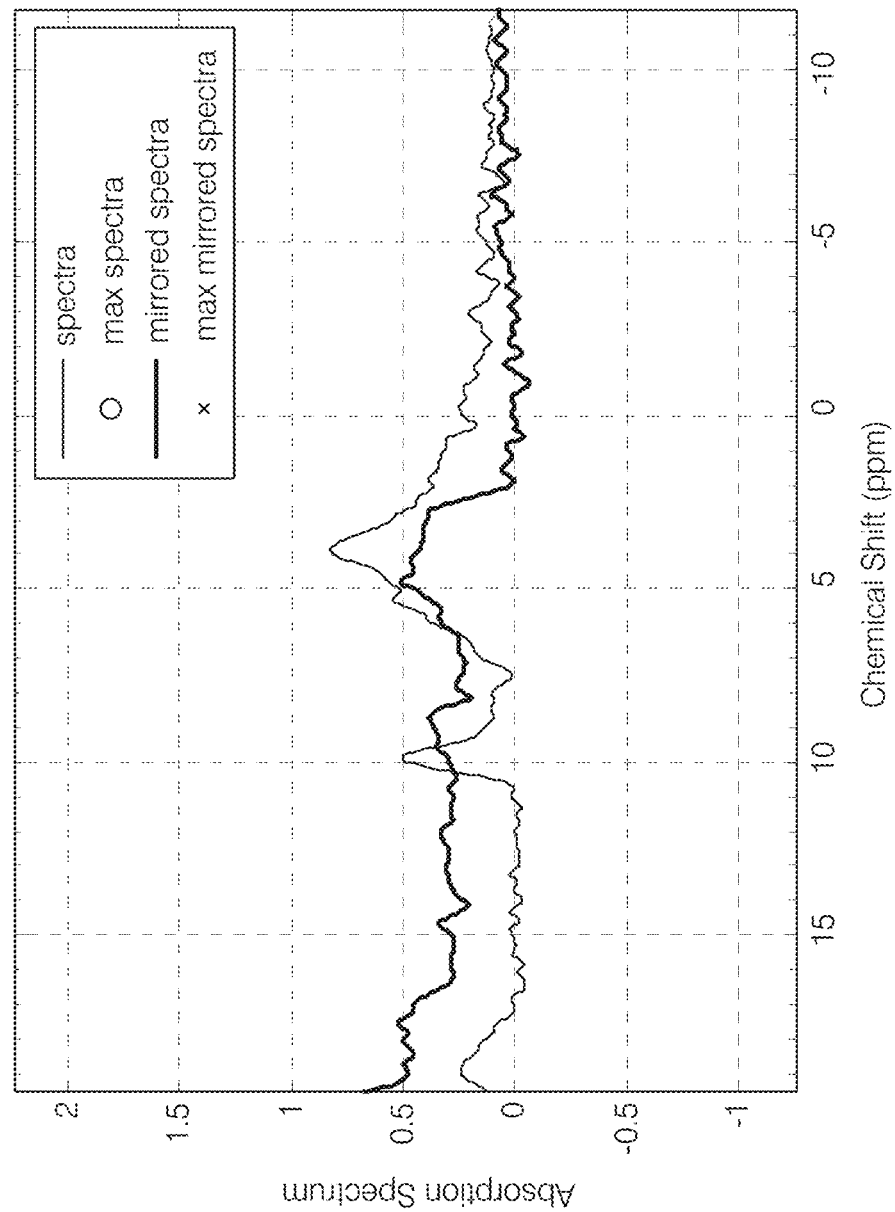
FIG. 14B shows same interim result of FIG. 14A, but in zoomed view along the metabolite range of interest.

Next the original and mirrored spectra are more finely aligned. This is because the location of down-field and up-field spectral components are not always exactly symmetric about water, though it is believed that where significant peak correlation results from fine tuning of the alignment, such step is supported as reasonable. Such fine alignment is done according to the particular present embodiment by correlating the spectral components in the chemical shift range [3.2-0.5]. FIGS. 14A-B show the fine aligned, full and zoomed spectra, respectively. Specifically noted by reference to that figure, the edges of the water suppression artifacts are in alignment. In this illustrative example of FIGS. 14A-B, the spectral components are aligned when the mirrored spectra is shifted 44 bins to the right. Only the mirrored spectrum is shifted so that we do not change the location of the up-field components as they are correctly located and aligned to water.

iii. Baseline Correction

Figure 15:
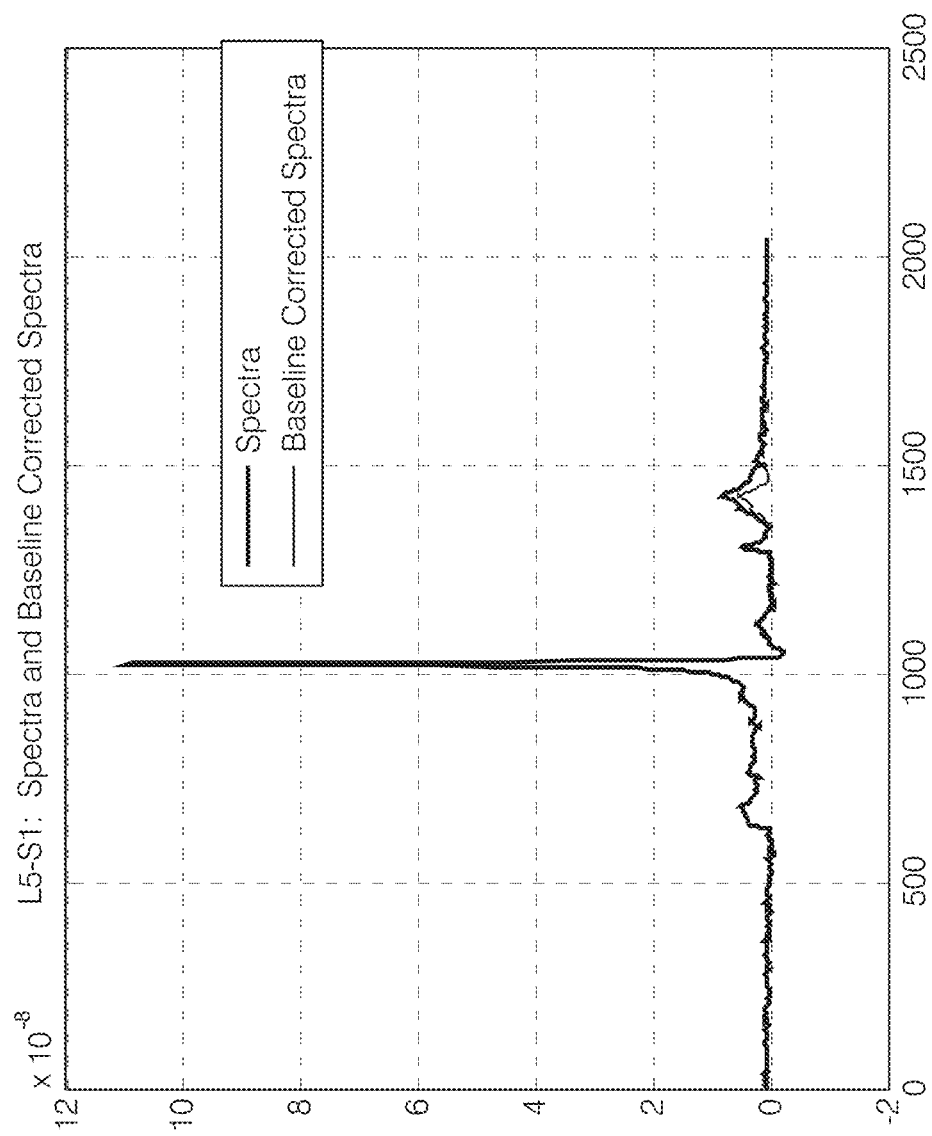
Figure 16:
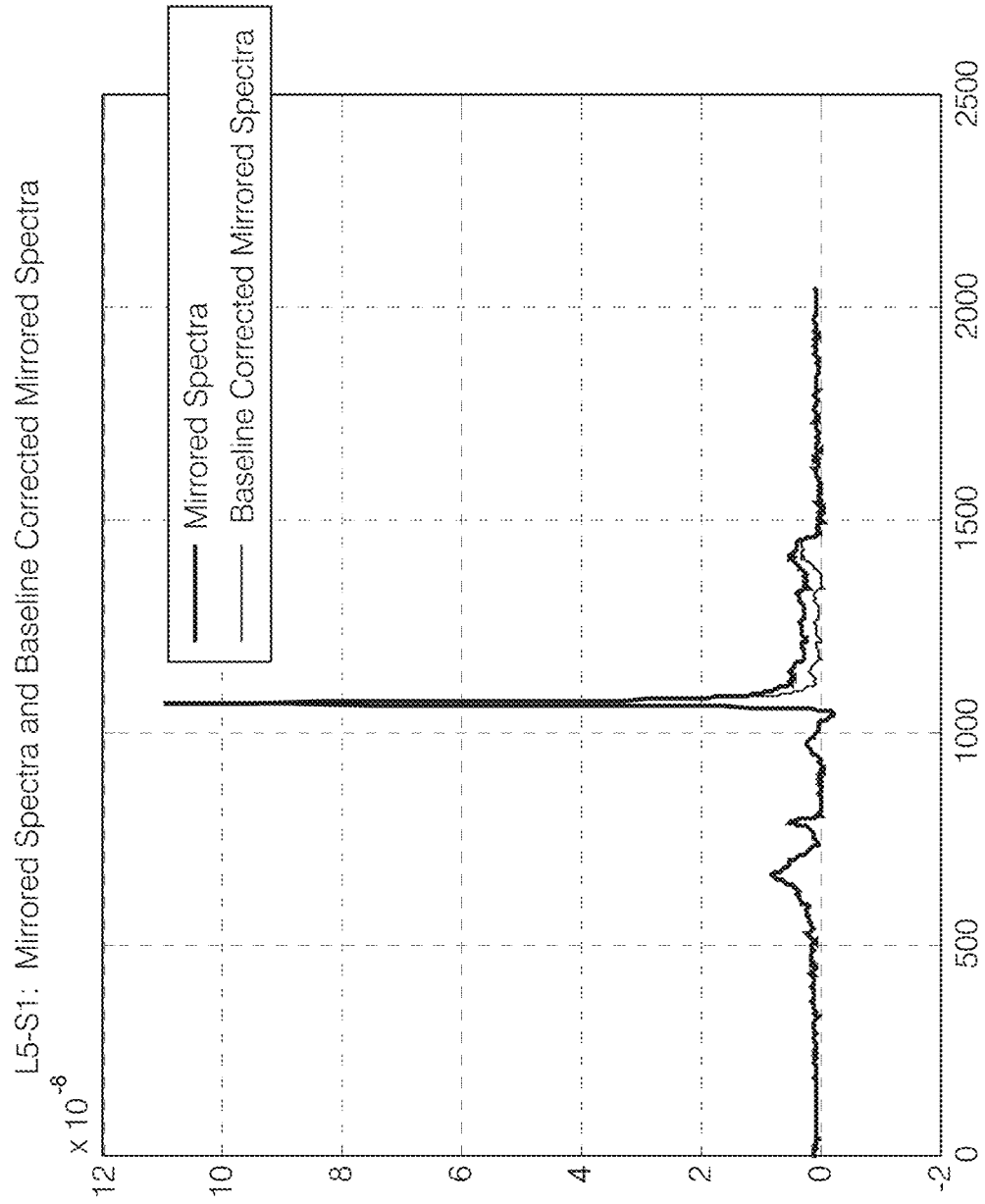

Baseline correction is an optional step, taken in the present embodiment prior to adjustment of the up-field spectral components via reflected downfield signal subtraction. The baseline correction algorithm operates only on the metabolite range of interest up field of water. A polynomial is used to fit data in the metabolite range. This method will not generally work on the entire spectra, though only ranges of interest need be worked upon in any event. Baseline correction is done separately on the up-field and mirrored down-field spectra (mirrored to the same metabolic range). FIG. 15 shows the baseline corrected spectra (only done on up-field spectral components) and FIG. 16 shows the baseline correction of the mirrored down-field spectra.

iv. Subtract Downfield from Up-Field Spectral Components

At this point the down-field spectral components are aligned with the up-field components and we have baseline corrected versions of both the up and down field spectra. Adjustment is accomplished by subtracting mirrored downfield spectra from the up field except in the up-field range corresponding to the down-field component in the Chemical Shift range [from about 4.7 to about 6 or 6.1] PPM. What follow are plots of the spectral components and correction using the baseline and non-baseline corrected spectra.

a. With Baseline Correction

Figure 17:
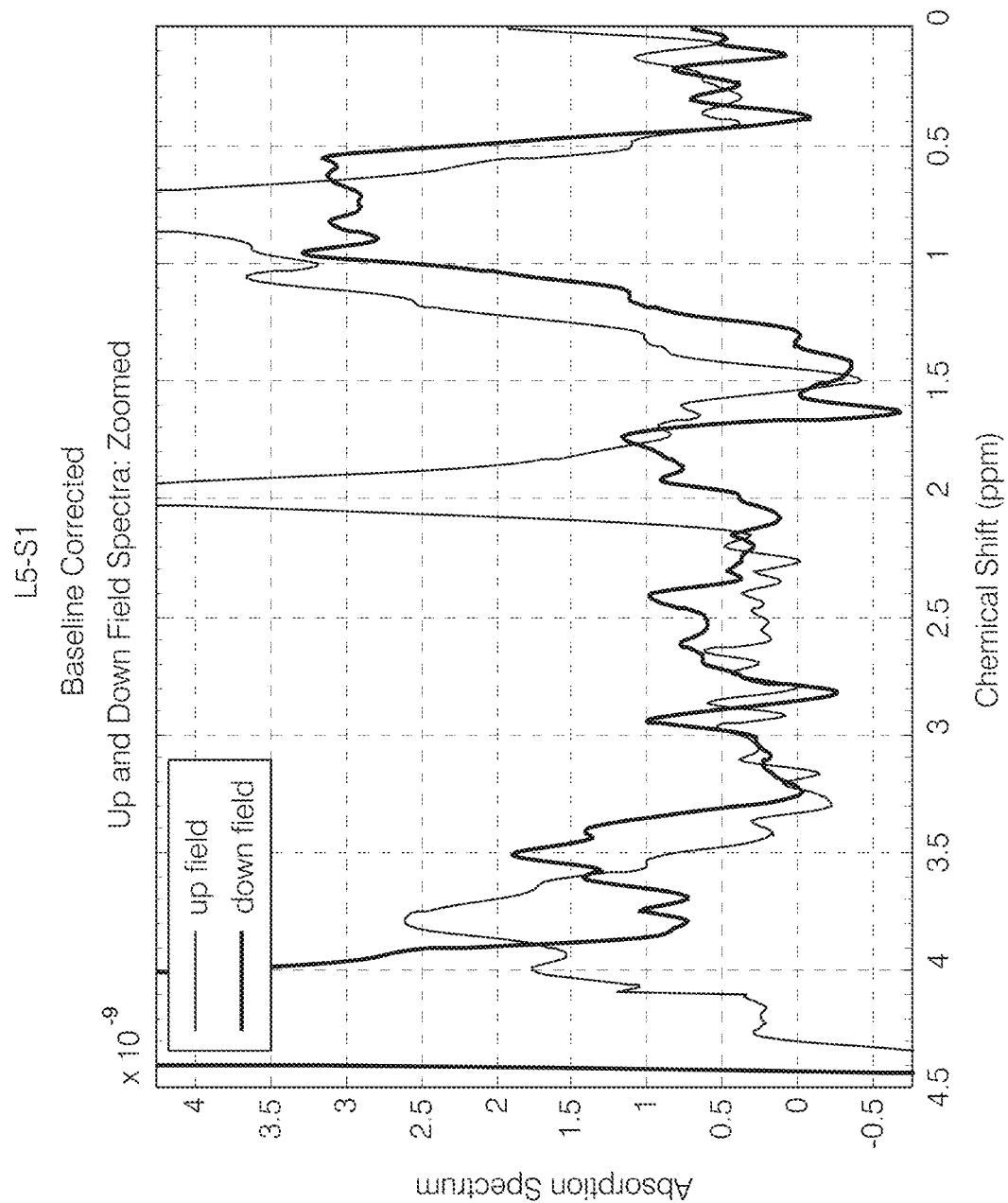
Figure 18:
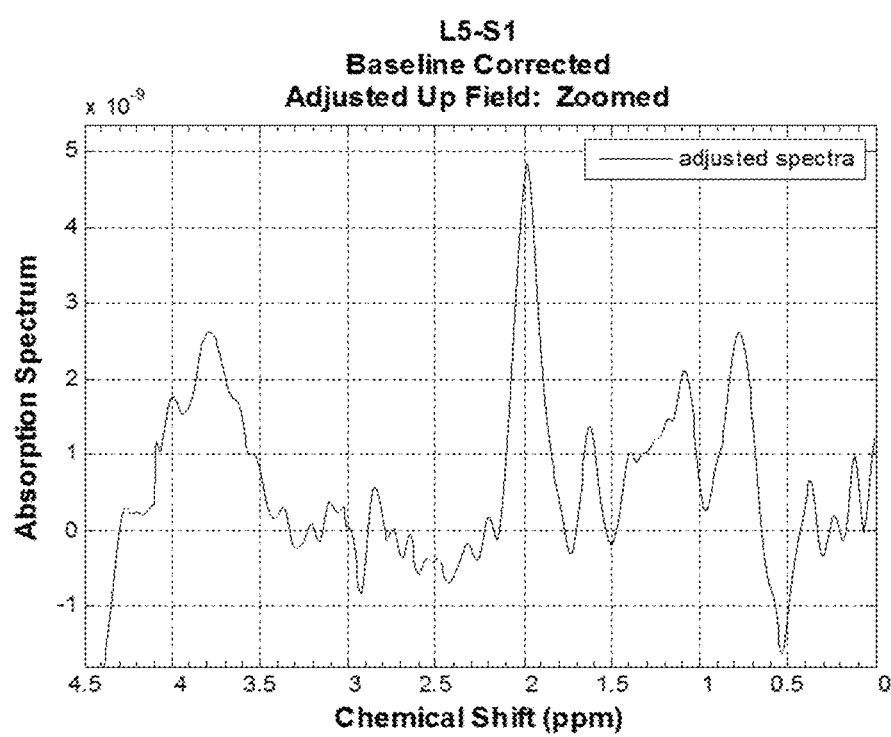

FIG. 17 shows the baseline corrected up-field spectra and the baseline corrected mirrored down-field spectra after coarse and fine alignment. FIG. 18 shows the adjusted up-field spectra.

b. Without Baseline Correction

Figure 19:
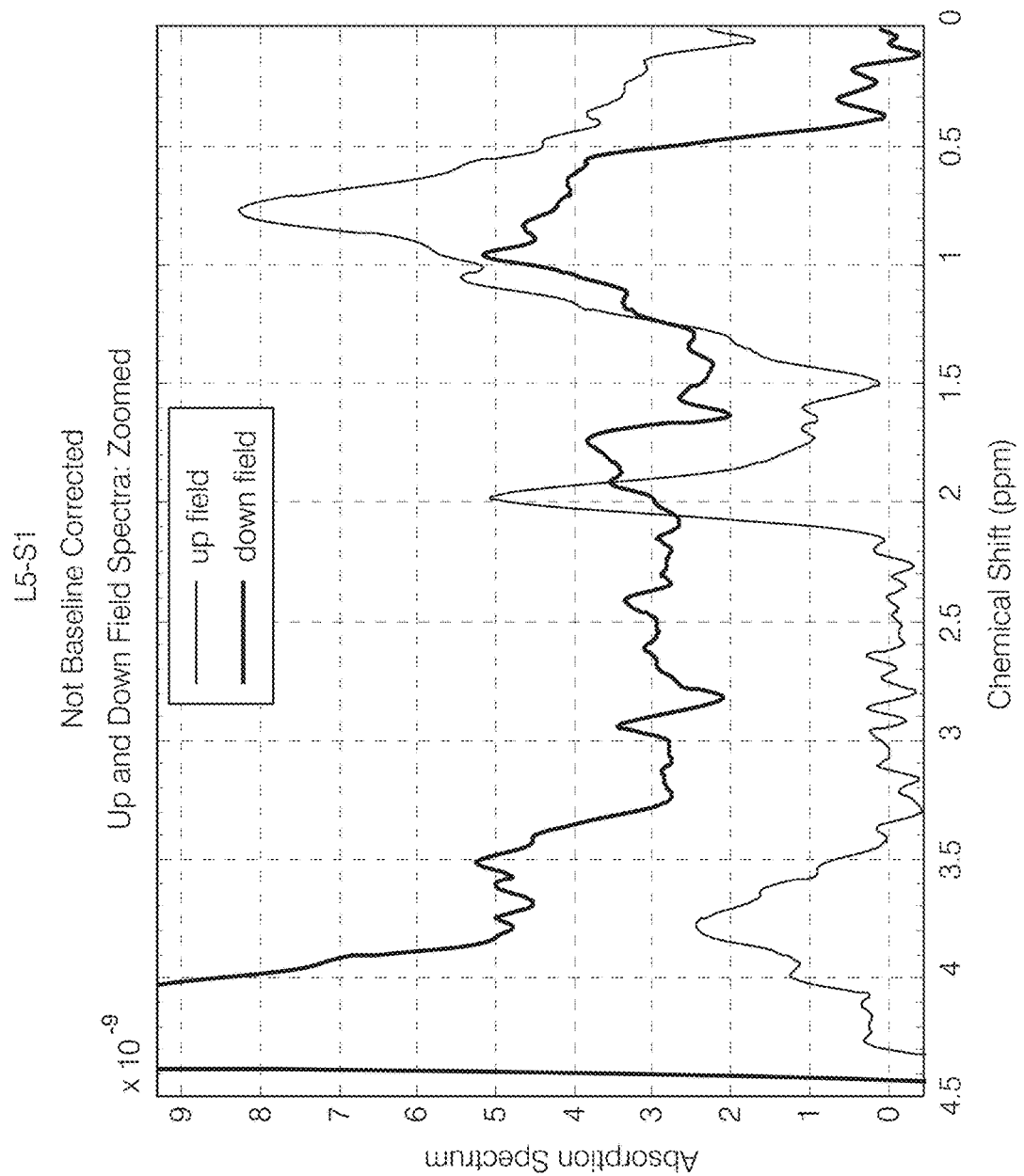
Figure 20A:
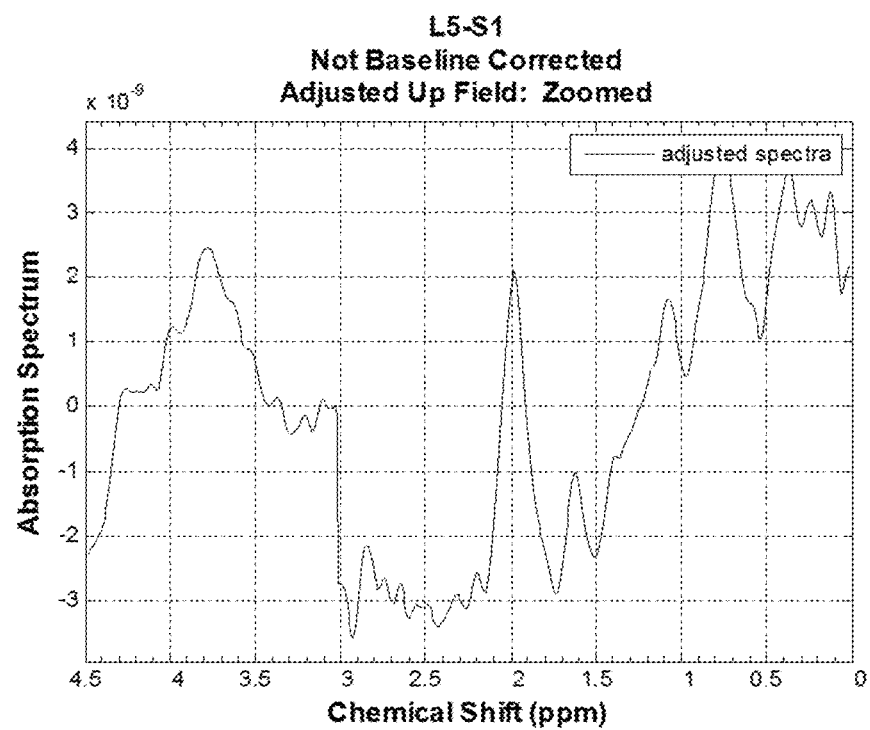
FIG. 20A shows an adjusted up-field spectrum using non-baseline corrected spectra of FIG. 19A, zoomed metabolite range.
Figure 20B:
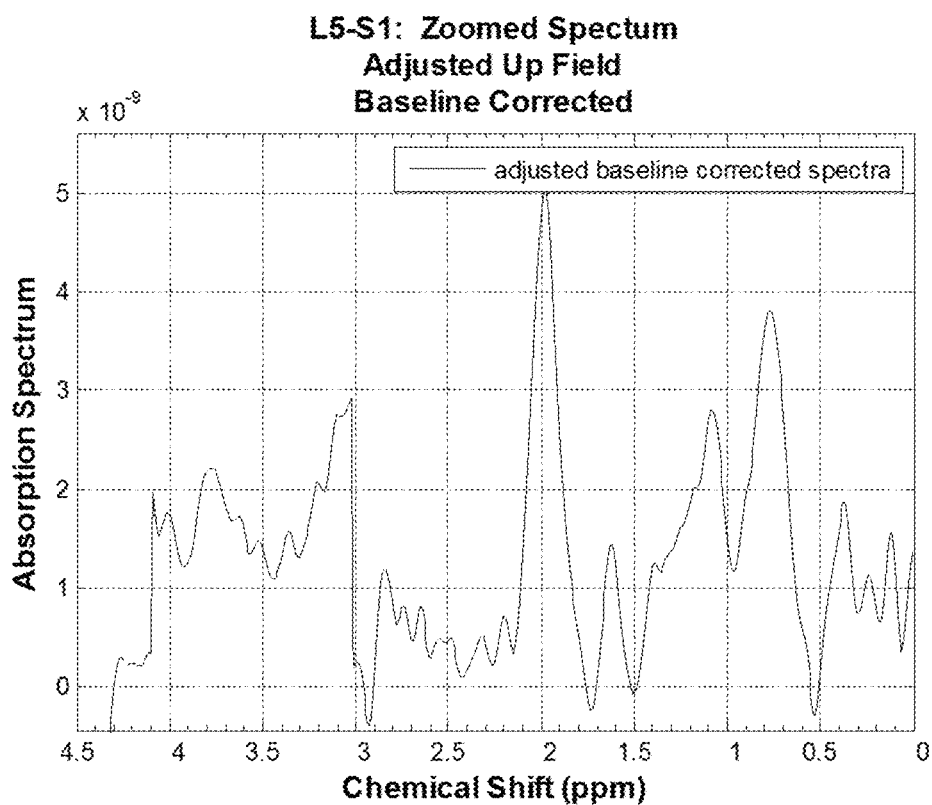
FIG. 20B shows an adjusted spectrum post-fine alignment and subtraction, baseline corrected, per a further embodiment under Example 1, zoomed metabolite range.
Figure 21A:
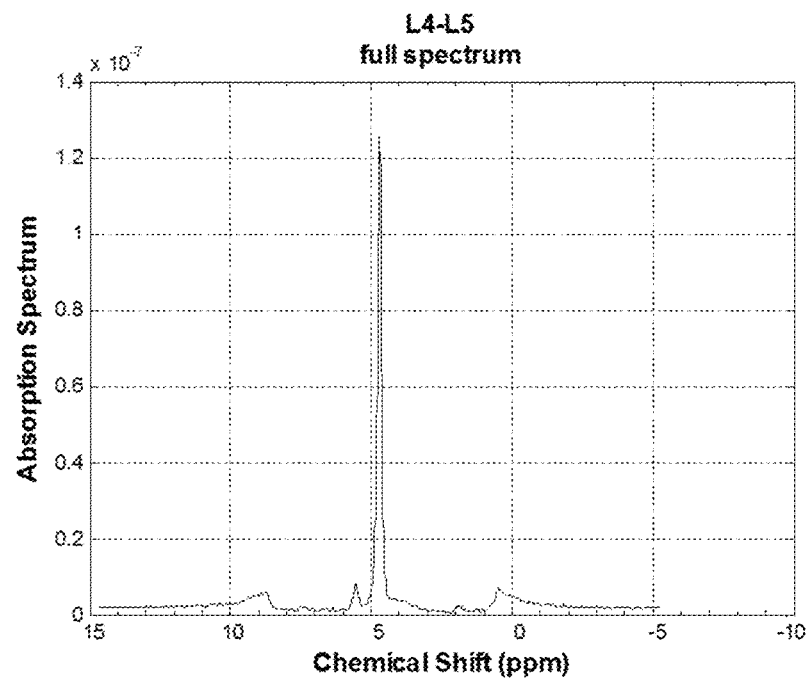
FIG. 21A shows an input spectrum according to another downfield correction embodiment of Example 2, post-processed (but without baseline correction or downfield adjustment), in full spectrum range.
Figure 21B:
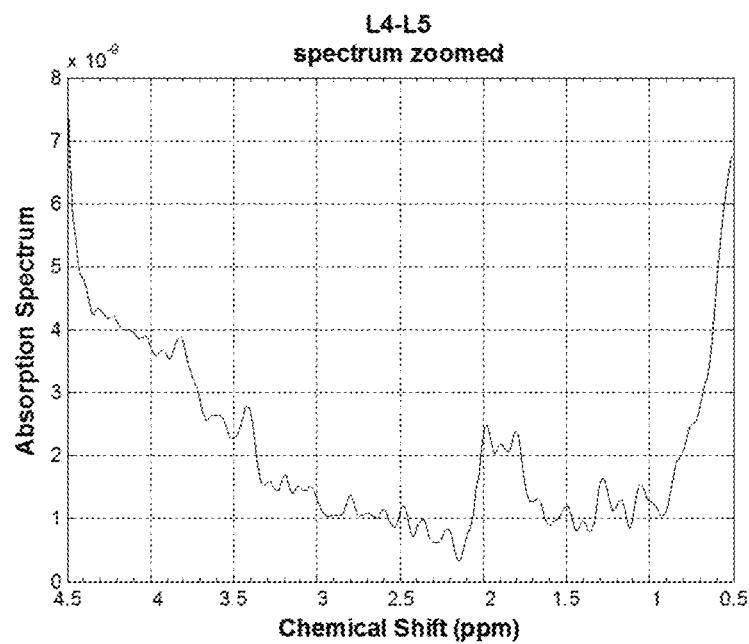
FIG. 21B shows the input spectrum of FIG. 21A further to the Example 2 embodiment, in zoomed metabolite spectrum range.
Figure 22A:
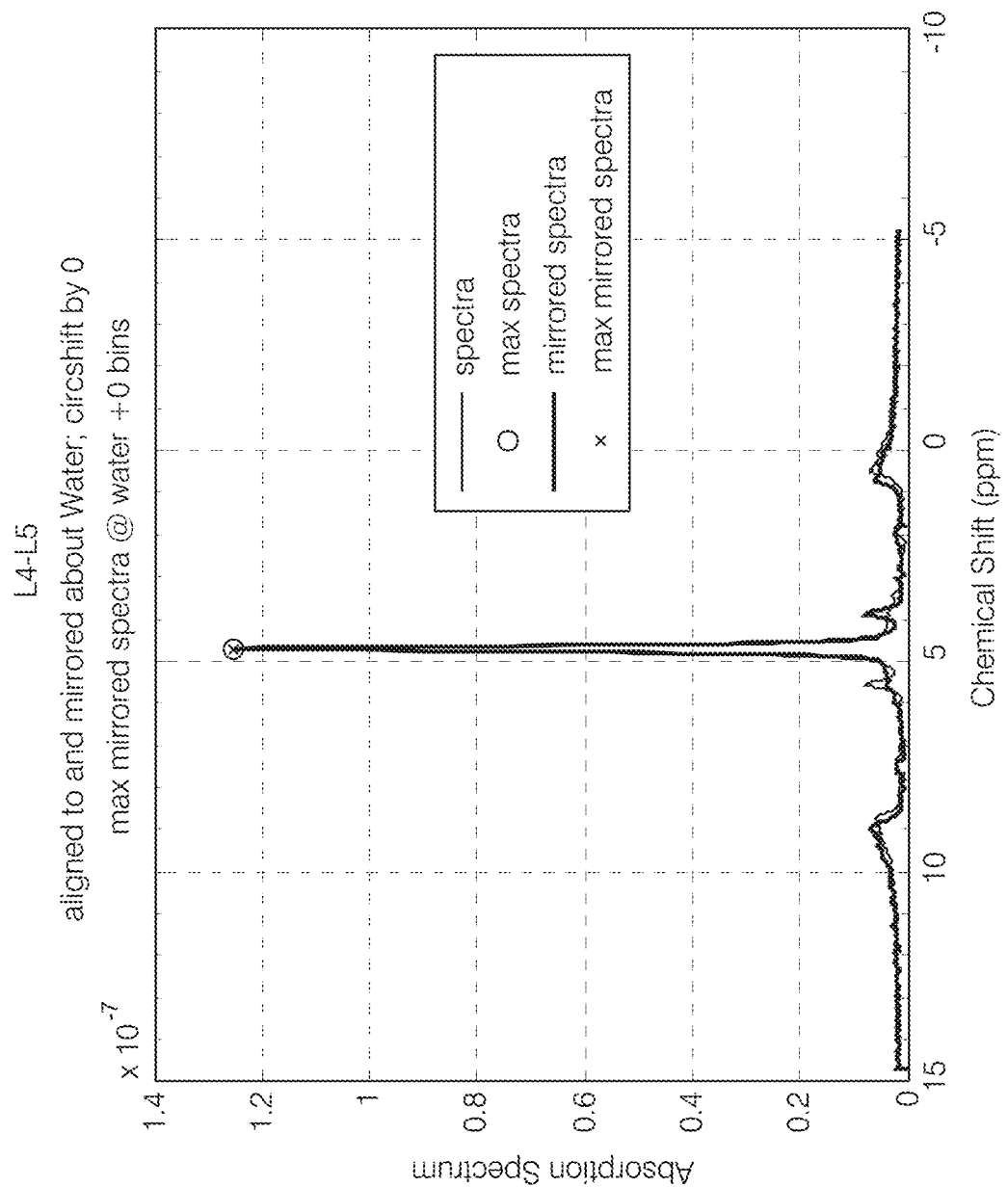
FIG. 22A shows another graph illustrating the Example 2 embodiment shown in FIGS. 21A-B, but shows a reflected or mirrored representation of the downfield spectrum (mirrored around water) in overlay over the corresponding opposite upfield range of the same spectrum, following course alignment, in full spectrum range.
Figure 22B:
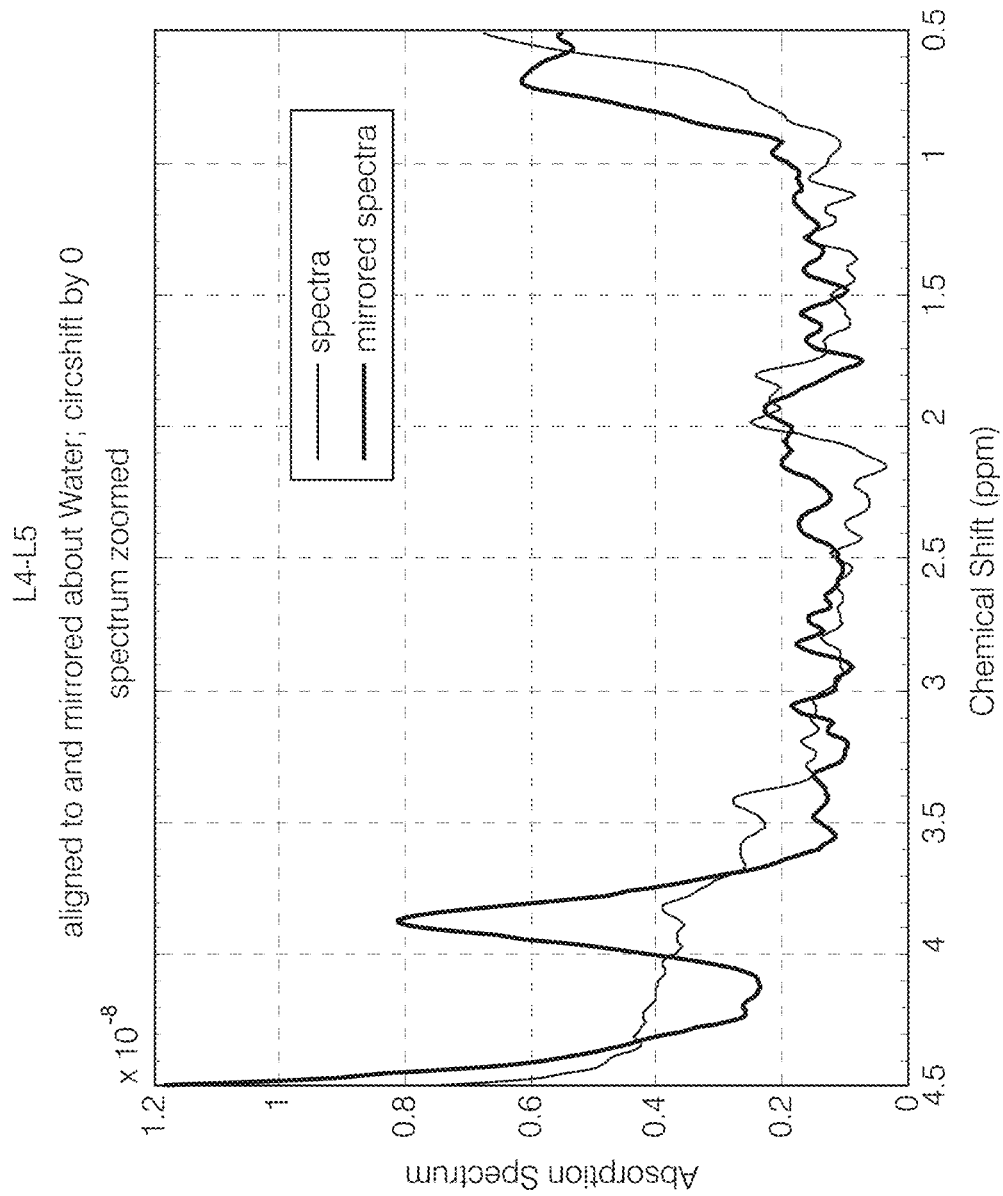
FIG. 22B shows the same spectrum and reflected overlay downfield spectrum shown in FIG. 22A further to Example 2, in zoomed metabolite range.
Figure 23A:
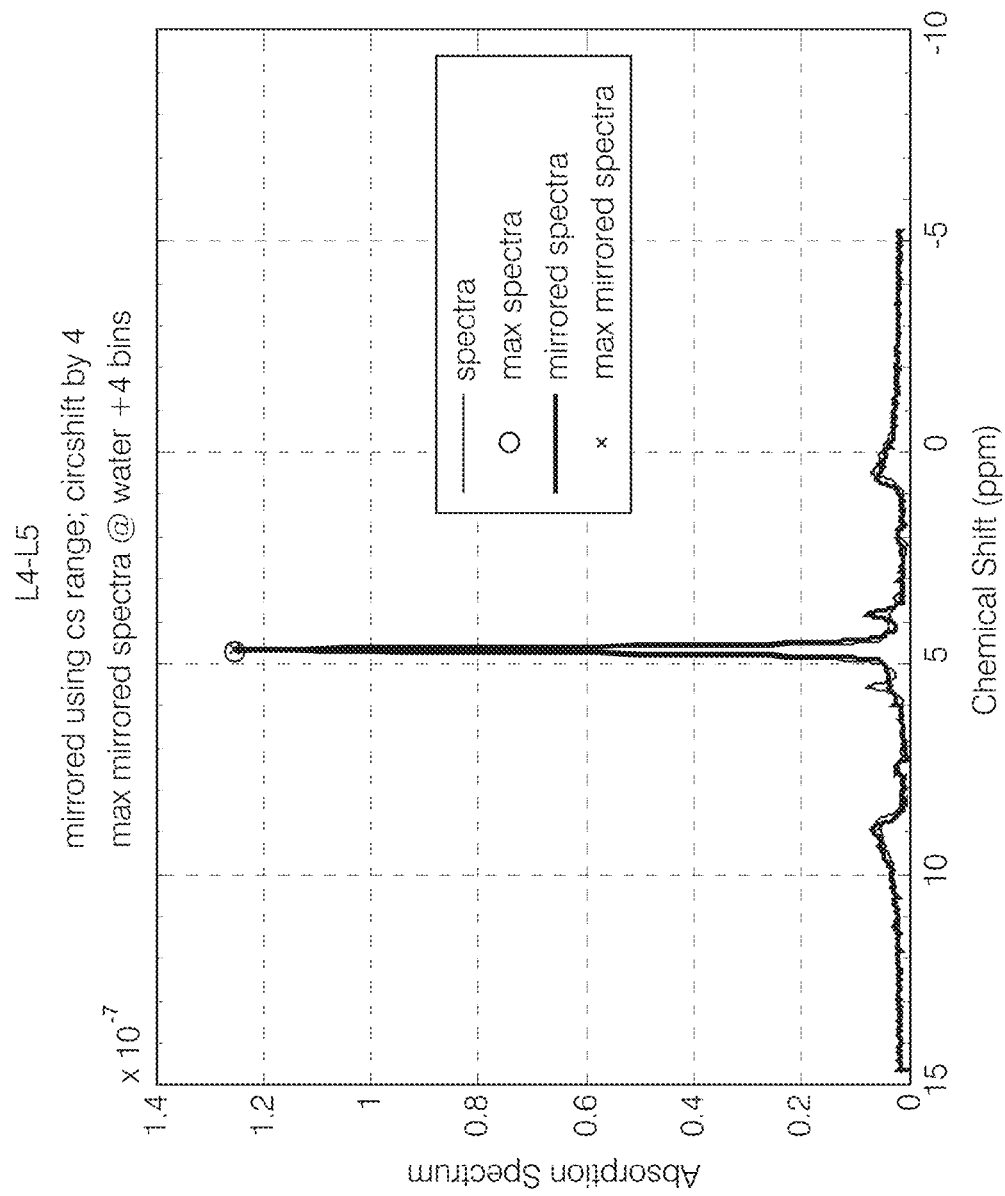
FIG. 23A shows the same overlay view of upfield spectrum with reflected downfield spectrum of Example 2, but post fine alignment, in full spectrum range.
Figure 23B:
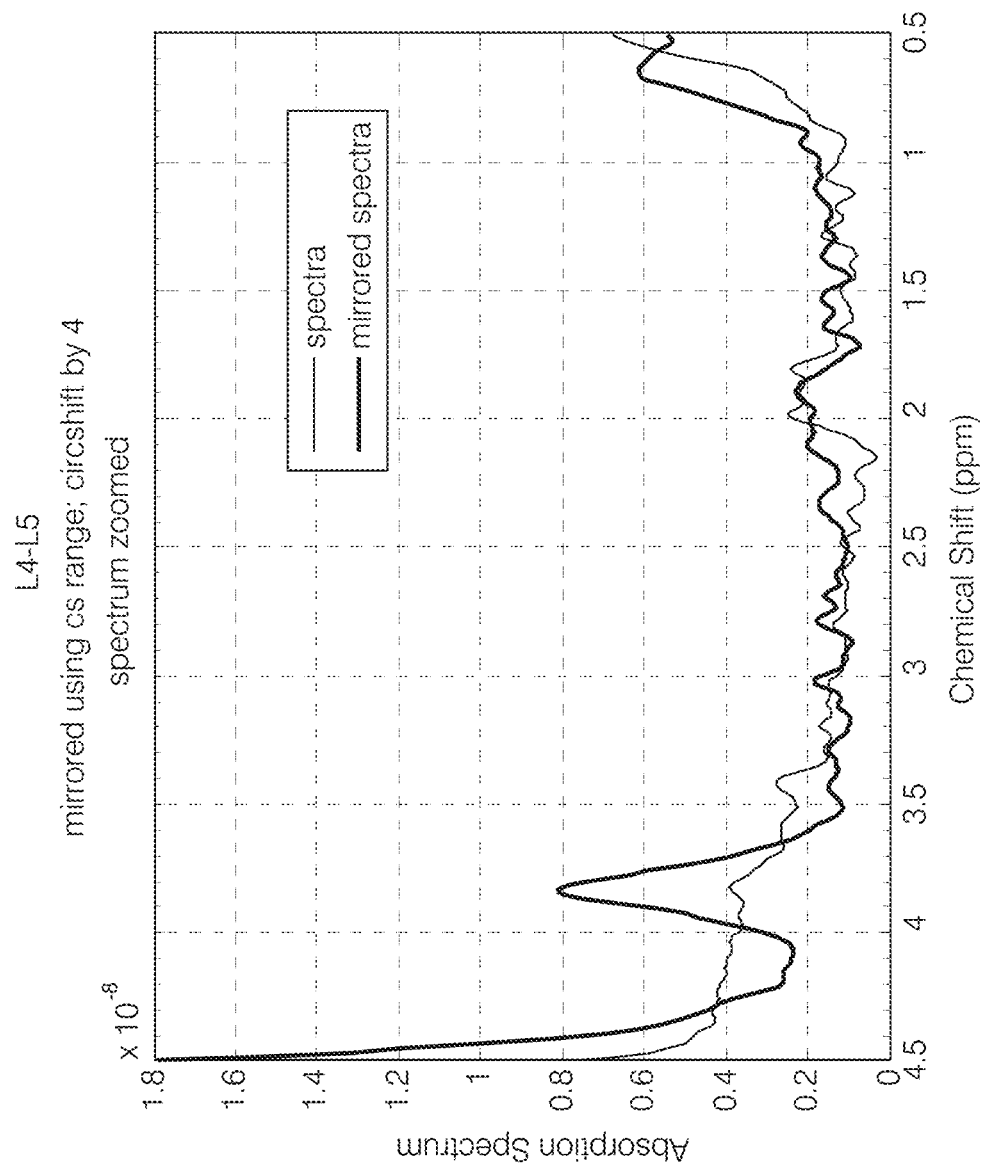
FIG. 23B shows the same spectral overlay of Example 2 shown in FIG. 23A, but in zoomed metabolite spectrum.
Figure 24A:
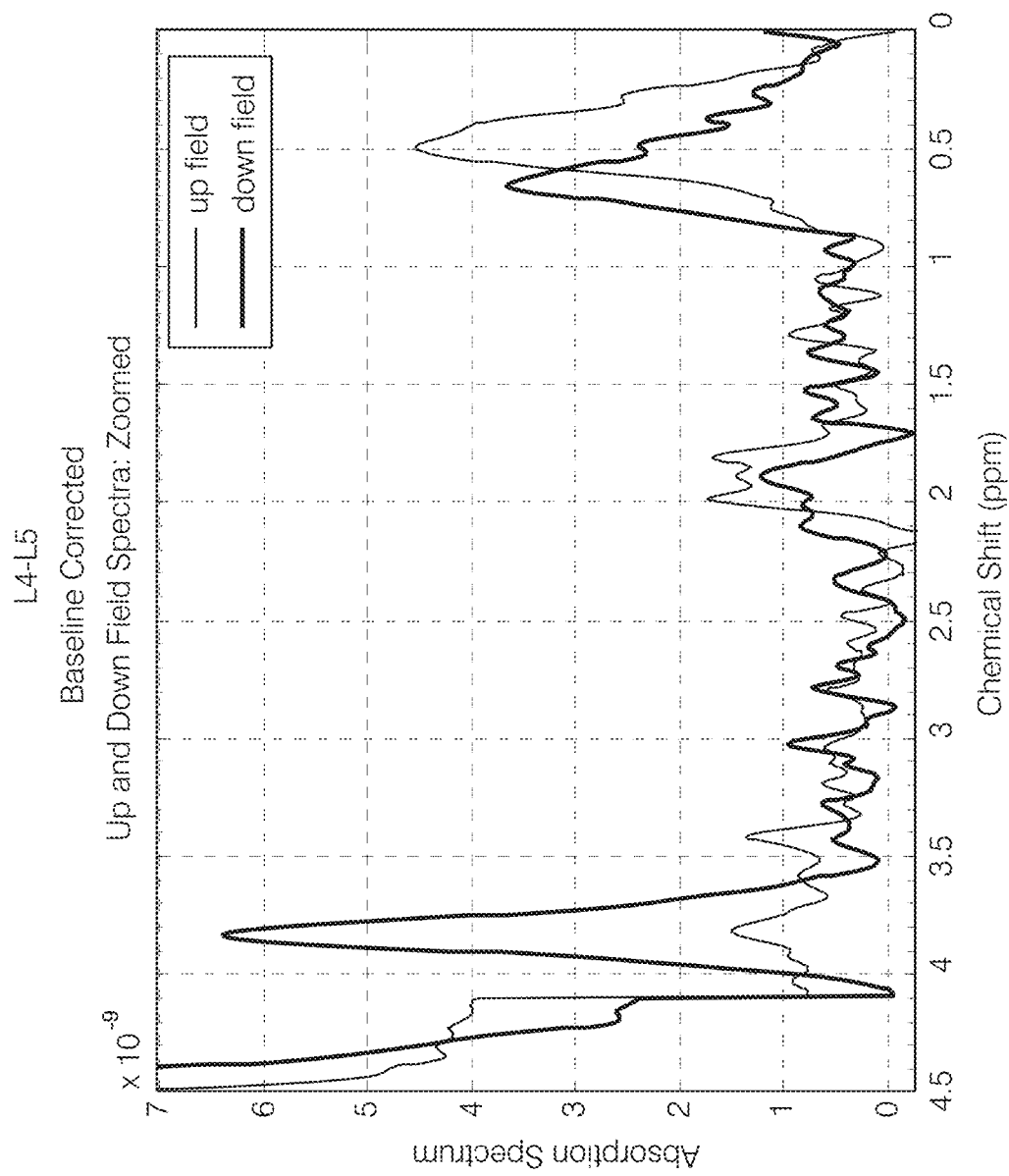
FIG. 24A shows the same overlay view of spectra under Example 2 shown in FIG. 23B, but after baseline correction, in zoomed spectrum range.
Figure 24B:
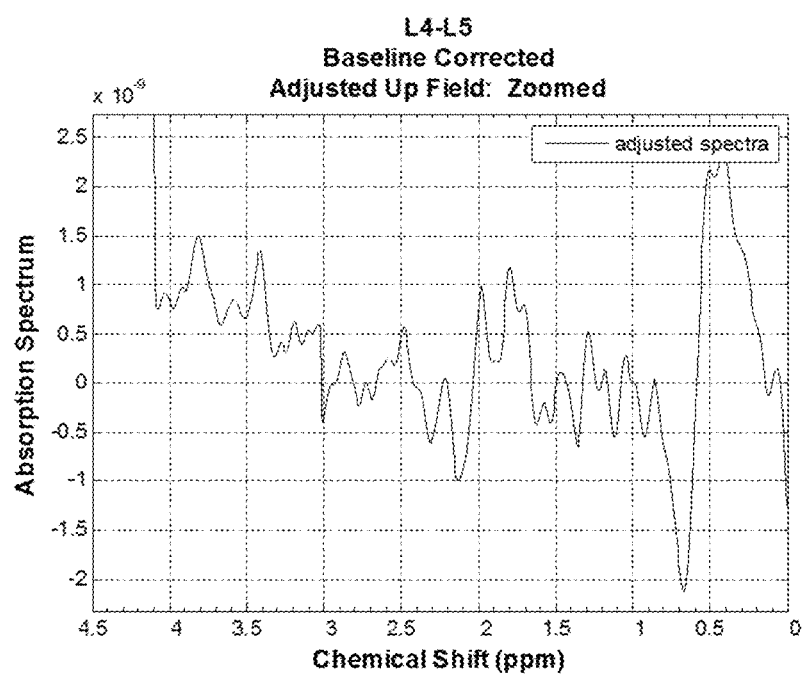
FIG. 24B shows the result under Example 2 of subtracting and correcting the spectrum of FIG. 24A by subtraction with the reflected downfield spectrum also shown in FIG. 24A, baseline corrected, in zoomed metabolite range.
Figure 25A:
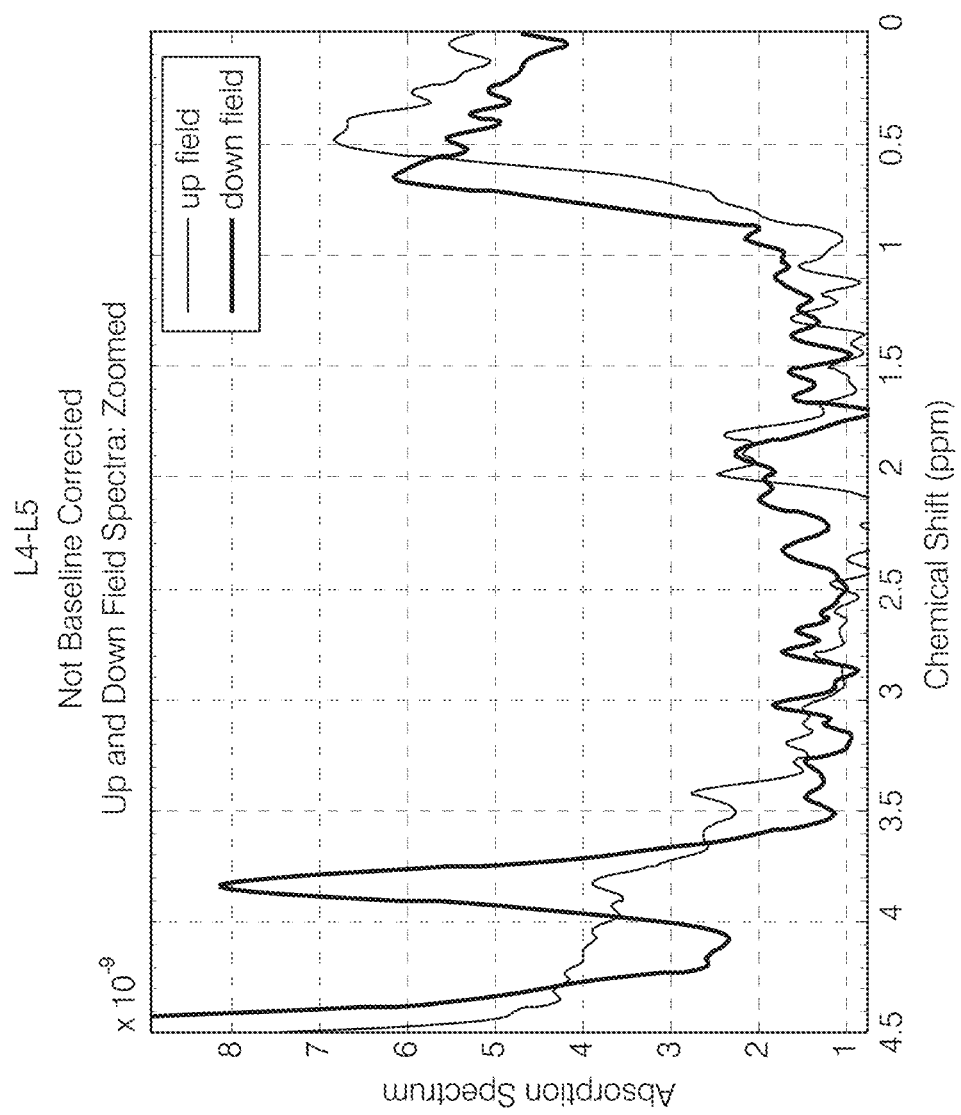
FIG. 25A shows another graph under Example 2 showing overlay between reflected downfield spectrum onto upfield spectrum, post-fine alignment and without baseline correction, in zoomed spectrum range.
Figure 25B:
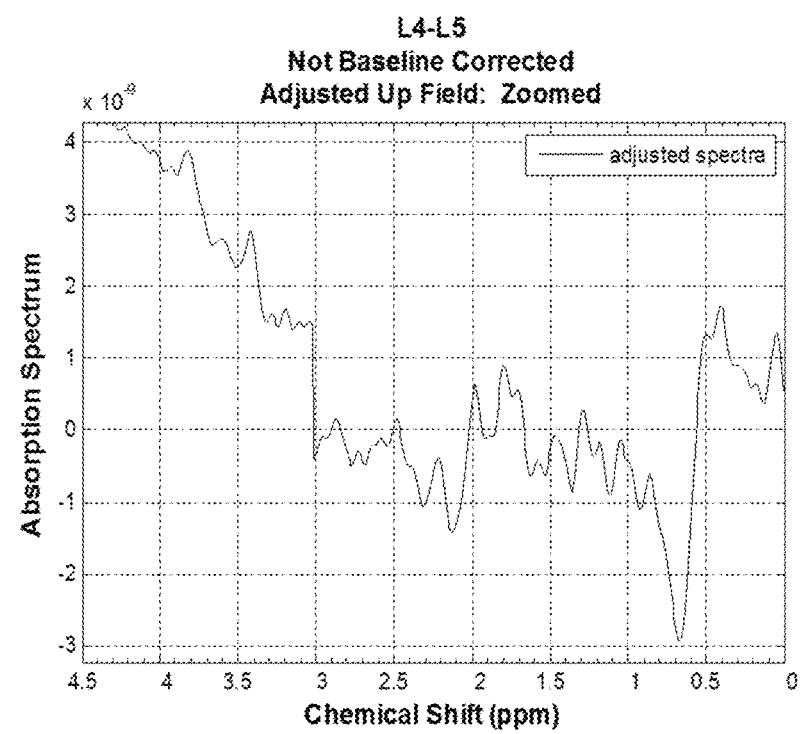
FIG. 25B shows adjusted spectrum after subtracting reflected baseline from upfield spectra shown in FIG. 25A, without baseline correction, in zoomed metabolite spectrum range.
Figure 25C:
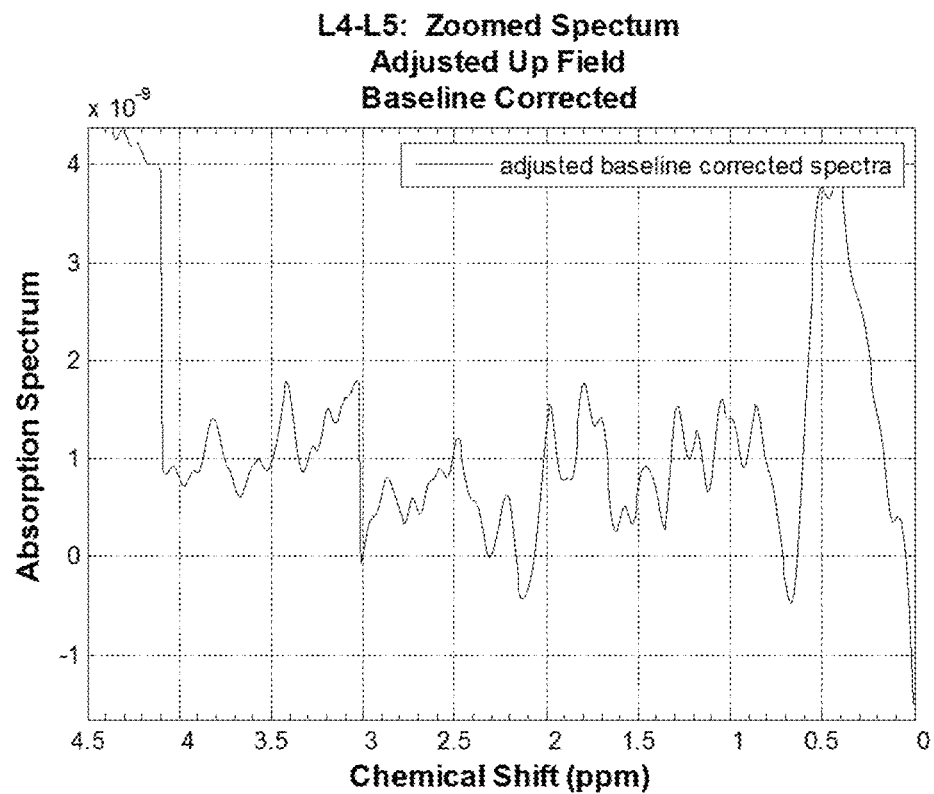
FIG. 25C shows the adjusted spectrum of FIG. 25B, post-baseline correction, in zoomed metabolite spectrum range.
Figure 26A:
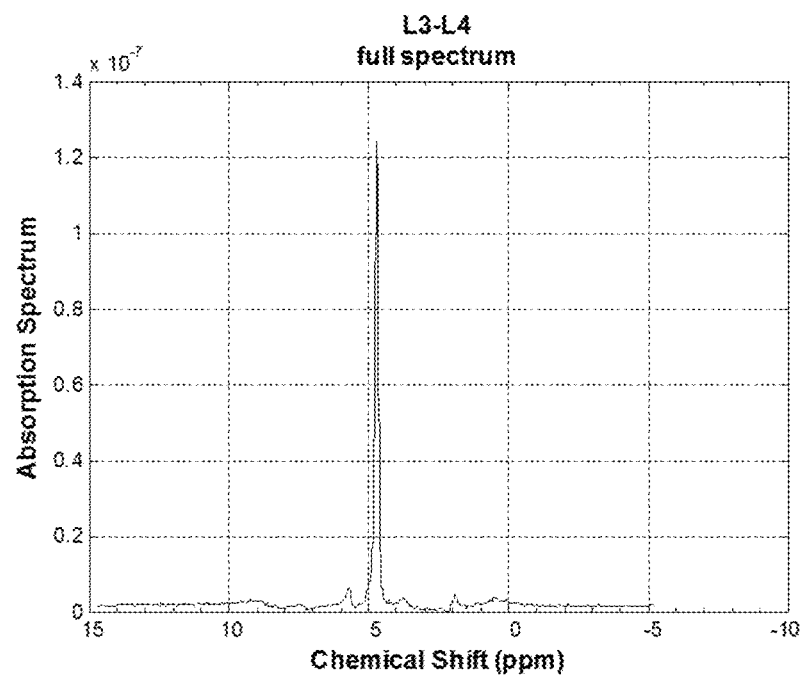
FIG. 26A shows an input spectrum according to another embodiment of Example 3, and which is post-processed (but without baseline correction or downfield adjustment), in full spectrum range.
Figure 26B:
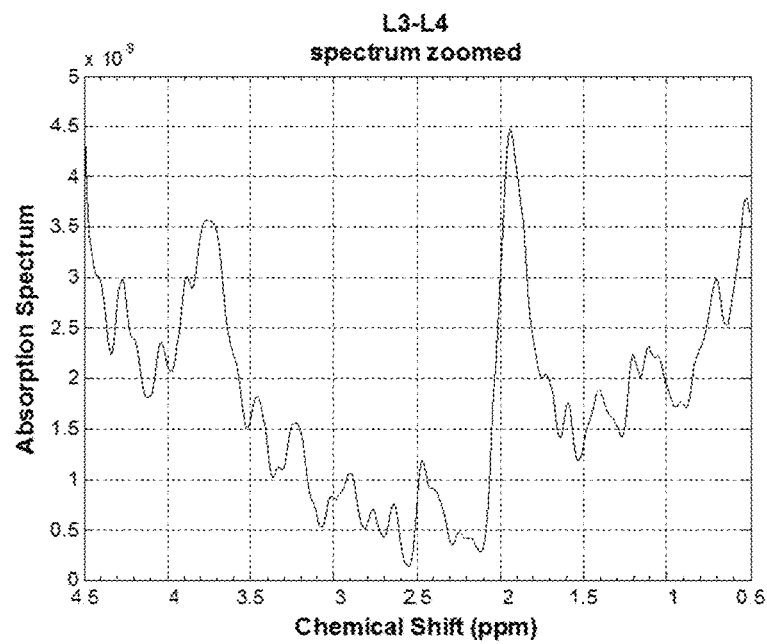
FIG. 26B shows the input spectrum of Example 3 shown in FIG. 26A, in zoomed spectrum range.

FIG. 19 shows the up-field spectra and the mirrored down-field spectra after coarse and file alignment, but without baseline correcting these respective spectra prior to adjustment. FIG. 20A-B show the adjusted up-field spectra after applying the downfield subtraction, which is shown pre- (FIG. 20A) and post- (FIG. 20B) baseline correction following the adjustment, respectively.

Further examples are similarly illustrated in FIGS. 21A-25C, 26A-30C, and 31A-35C, respectively, for three additional clinical test cases involving 3 T acquisitions from other discs at other lumbar levels in other subject exams.

Spectral results are evaluated by plotting the adjusted up field spectrum in the range of metabolic interest PPM, and generally limiting the Y axis values to provide optimal observation between (e.g. +10%) of the maximum and minimum in the defined range. Comparison is then made vs. final post-processed spectra without the downfield subtraction to understand possible contribution of the artifact being evaluated, and general spectral quality analysis (e.g. SNR). Metrics, such as comparison of resulting SNR of signal region of interest pre- vs. post-adjustment, or correlation measurement of the reflected aligned downfield signals with the upfield signals, may also be used according to further embodiments to then determine whether the adjusted result, or non-adjusted result, should be used.

It is also appreciated that measurement data of downfield artifact signal may be subtracted from upfield metabolic ranges of interest, vs. performing spectral adjustments. This may relate to the same alignment approaches as above for spectral adjustment, but simply not change the shape of the spectrum but rather simply adjust the spectral measurements to account for estimated downfield reflected artifact contribution. Among other benefits of this approach, this does not require a "step" change in the resulting spectrum at the edge(s) where subtraction is used versus not used.

This data subtraction approach may be conducted as follows. Similar range "alignment" approaches may be used as with spectral subtraction adjustment approach above. However, then this is merely used to determine ranges of up-field and reflected downfield artifact measurements to take for subtraction adjustment. This may involve measuring peak and/or areas under the curve (AUC) for metabolic regions of interest, and reflected similar ranges on downfield side of water (e.g. other side of 4.7, or as reflected and aligned, either coarse or finely). Then the values for downfield ranges are subtracted from aligned upfield ranges, providing "corrected" measurements. This may also be evaluated versus upfield ranges measured prior to correction to determine artifact contribution.

The robust basis and approach for reflected downfield artifact correction in upfield signal ranges of MRS spectra is supported by way of this description and illustrative examples shown. It is also appreciated that this may be further developed through refinements over larger sample sizes of data. In particular, custom variations may be employed to address certain particular types of reflected artifact signals observed, and establish criteria by which to either use different approaches, and/or whether to use an adjusted spectrum (or measurement) or not in particular cases.

v. Validation of Mirroring Function

Subtracting reflected downfield signals from upfield metabolite range of interest is done according to the present embodiments principally based upon the presumed principles that that downfield signal is in fact artifact which is mirrored into the upfield range at the place where reflected downfield is aligned for subtraction. Accordingly, if mirroring of the input spectrum for downfield correction is not appropriately aligned to where real artifact is, the subtraction will inappropriately adjust the upfield signal by newly induced artifact by the inappropriately conducted subtraction. Accordingly, the mirrored reflection approach can be validated for proper alignment as intended, which is a useful approach to take as mis-alignment could confound results as stated. To validate this function, a further aspect of the present disclosure provides validation approach that comprises a simple test vector that is submitted to the operation, for its mirror image to be examined. The test vector is designed to simulate an input signal, and which may be for example the real part of a complex spectrum.

One particular example of such a validation is provided herein as follows. For simplicity of illustration, this example simulates a 16-point real spectrum. With this signal, DC is at bin 9 (16/2+1) and there are 7 (16/2−1) bins upfield from DC and 8 (16/2) bins downfield from DC. As there is not the same number of upfield and downfield bins; there is one "odd" bin, the furthest downfield, without a corresponding upfield bin. One issue thus presented by this approach is how to handle the "odd" bin. If the input vector were truly mirrored, then the mirrored vector would have 7 bins downfield and 8 bins upfield of DC. This would put DC at bin 8. The signals would be mirrored but the DC locations would be different. Alignment of the DC points could be forced by prefixing the mirrored sequence with one bin with amplitude zero, but then the test and its mirror would be different lengths. The other option, and the method implemented, is to mirror the entire spectrum except the "odd" bin. The leaves the DC bins aligned and the vectors are the same length.

Figure 27A:
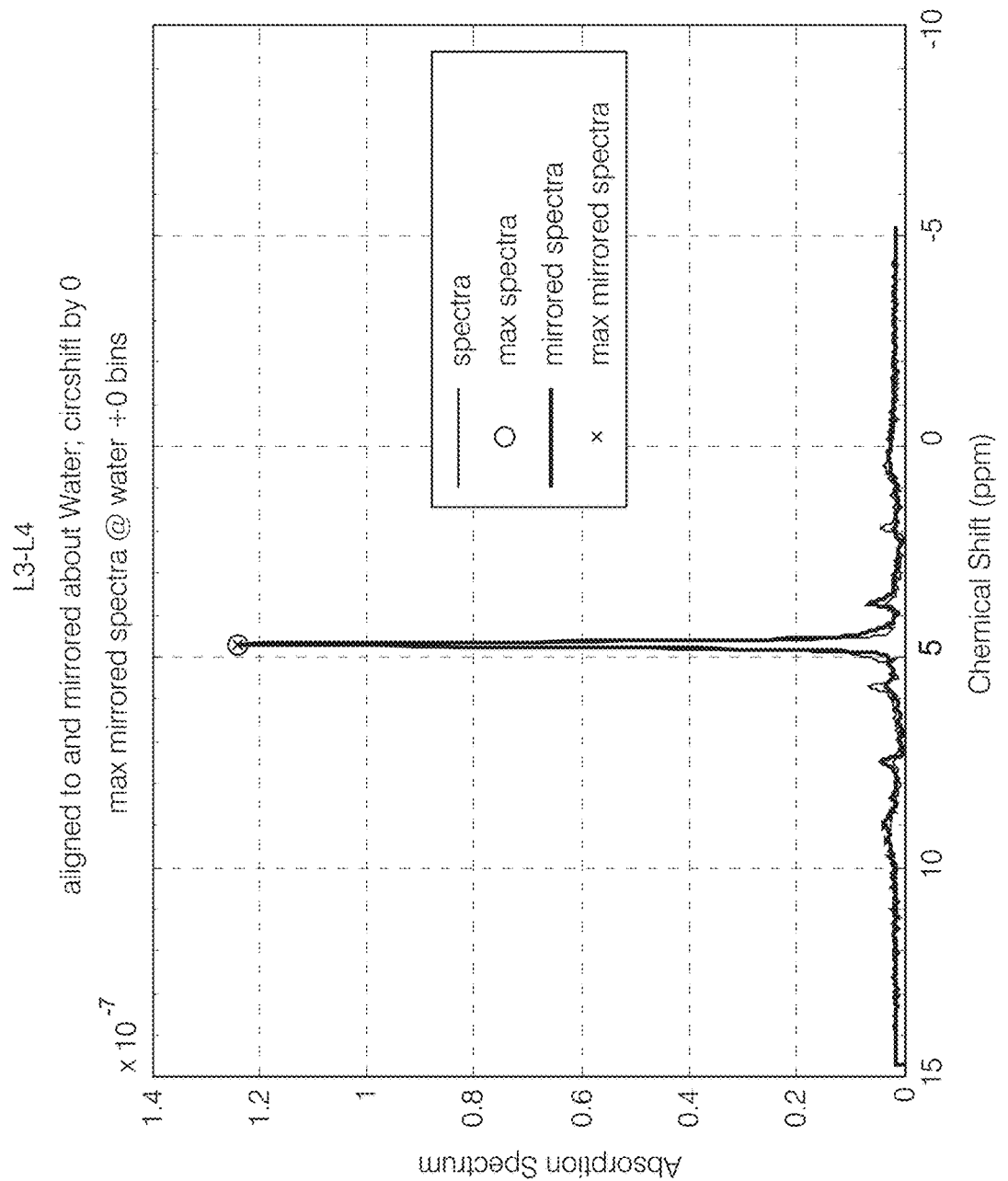
FIG. 27A shows the same spectrum of Example 3 shown in FIG. 26A, but in overlay with a reflected spectrum mirrored around water signal, with coarse alignment, in full spectrum range.
Figure 27B:
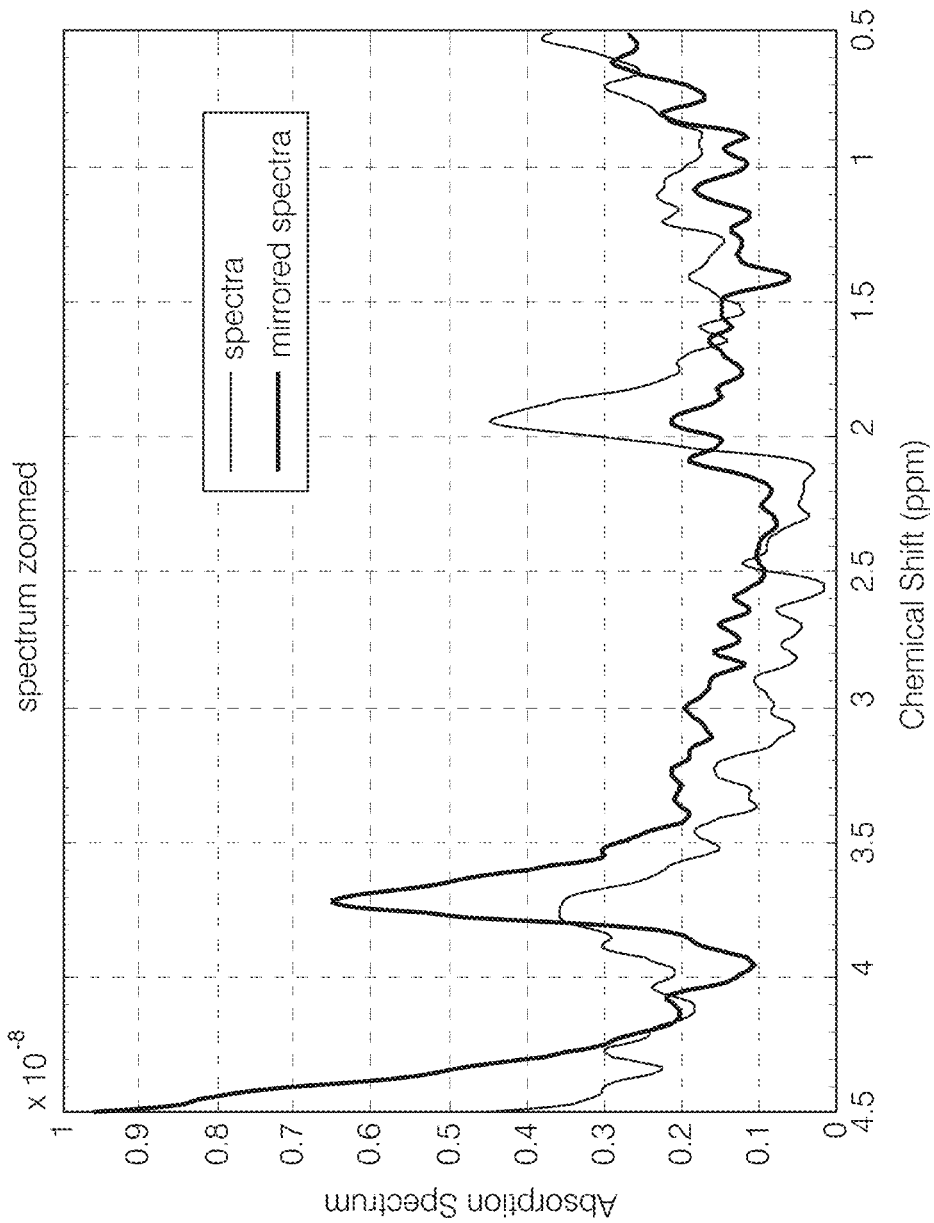
FIG. 27B shows the same overlaid spectra of Example 3 shown in FIG. 27A, in zoomed metabolite range.

FIG. 27 shows the discrete sampled test vector ("Input") in dashed line and its mirror ("tupnI") in dotted line. The signal is zero except at DC (amplitude=5), DC+5 (amplitude=1), DC−3 (amplitude=2), and the "odd" bin DC−8 (amplitude=3). The mirrored test vector shows that the mirroring function is correct: The "odd" bin has not moved; the DC bins are aligned, and the upfield and downfield components are mirrored about DC.

Figure 28A:
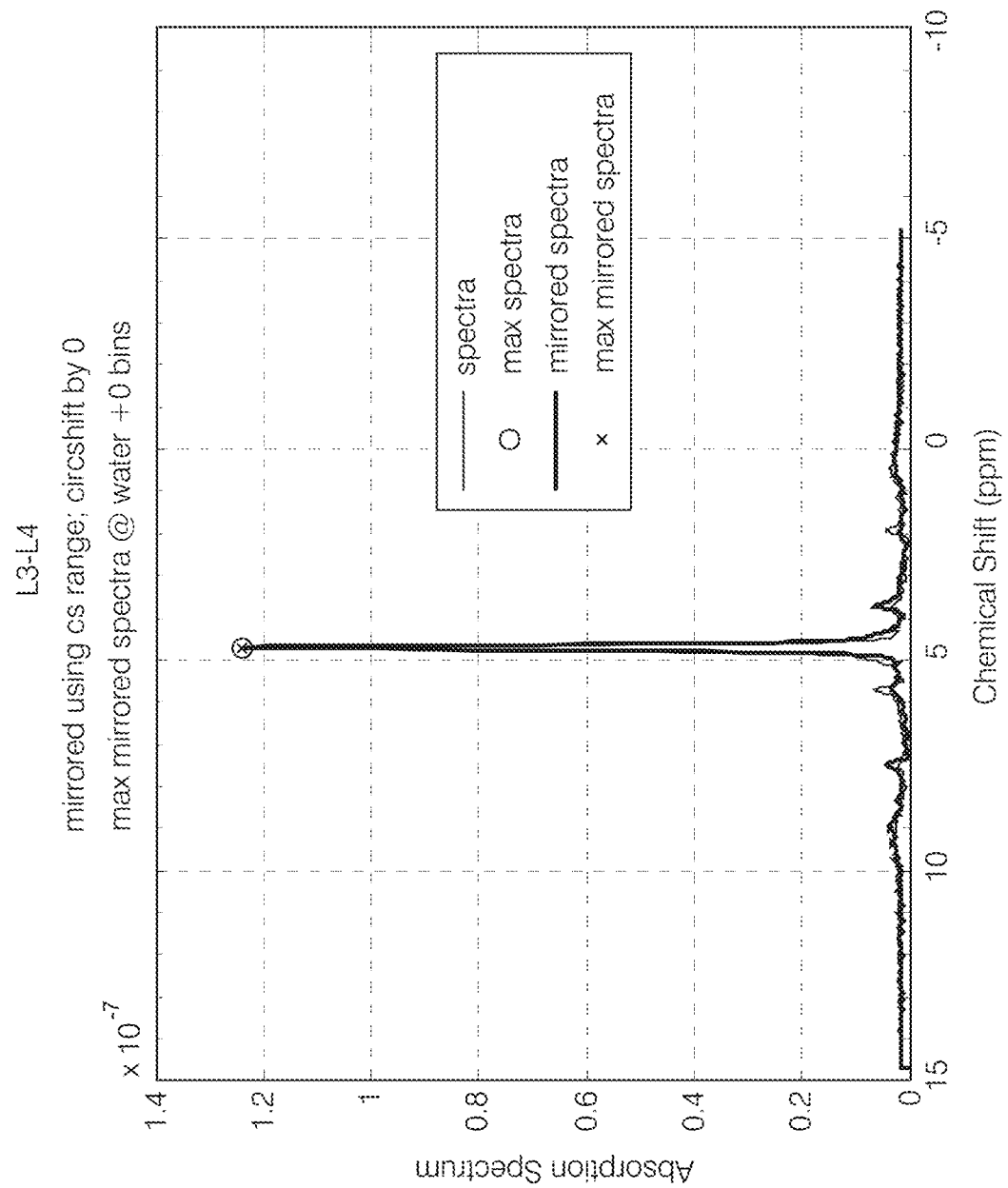
FIG. 28A shows the same overlaid spectra of Example 3 shown in FIG. 27A, but after fine alignment adjustment along the chemical shift X-axis, in full spectrum range.
Figure 28B:
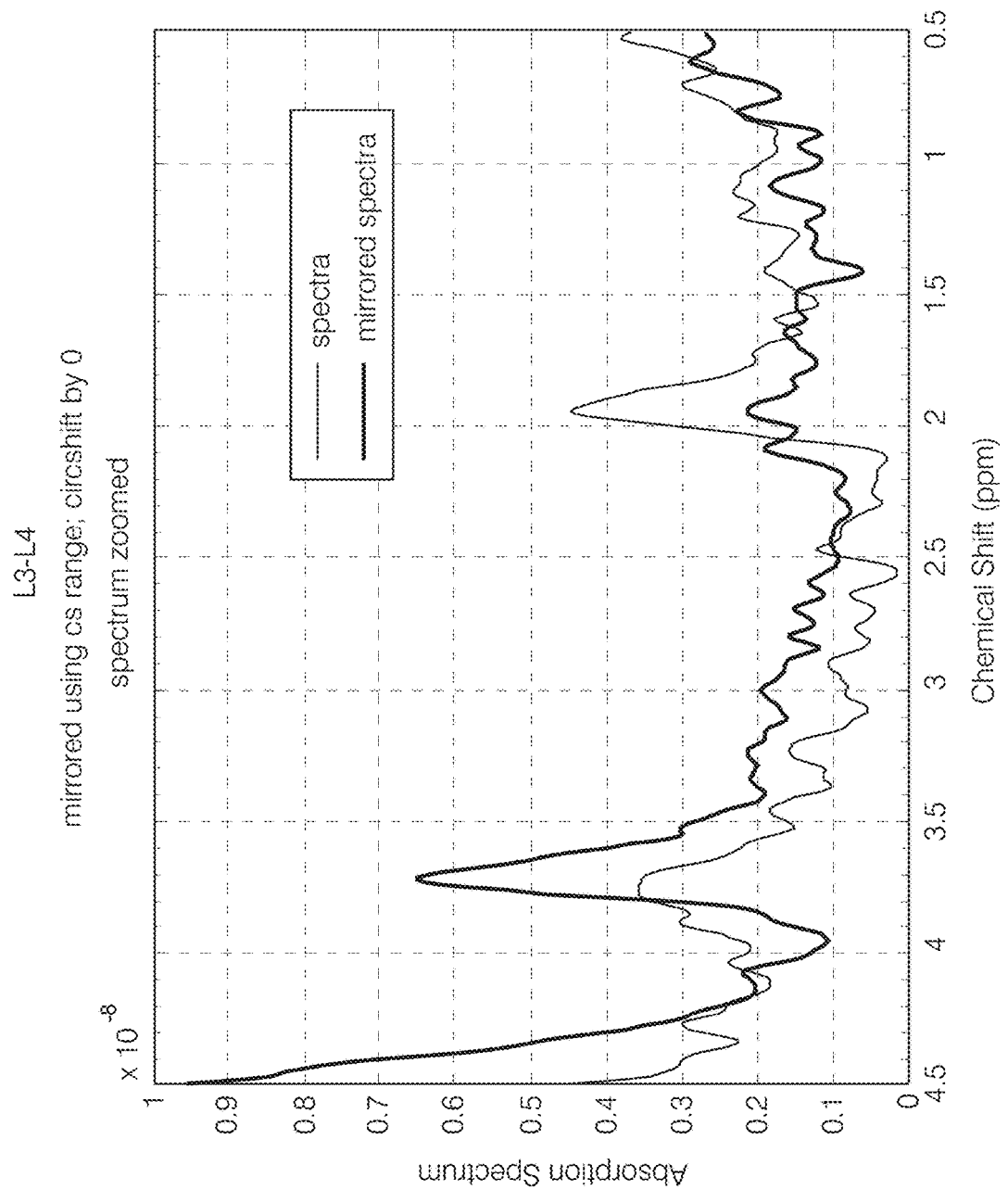
FIG. 28B shows the same overlaid spectra post-fine alignment of Example 3 shown in FIG. 28A, in zoomed metabolite range.
Figure 29A:
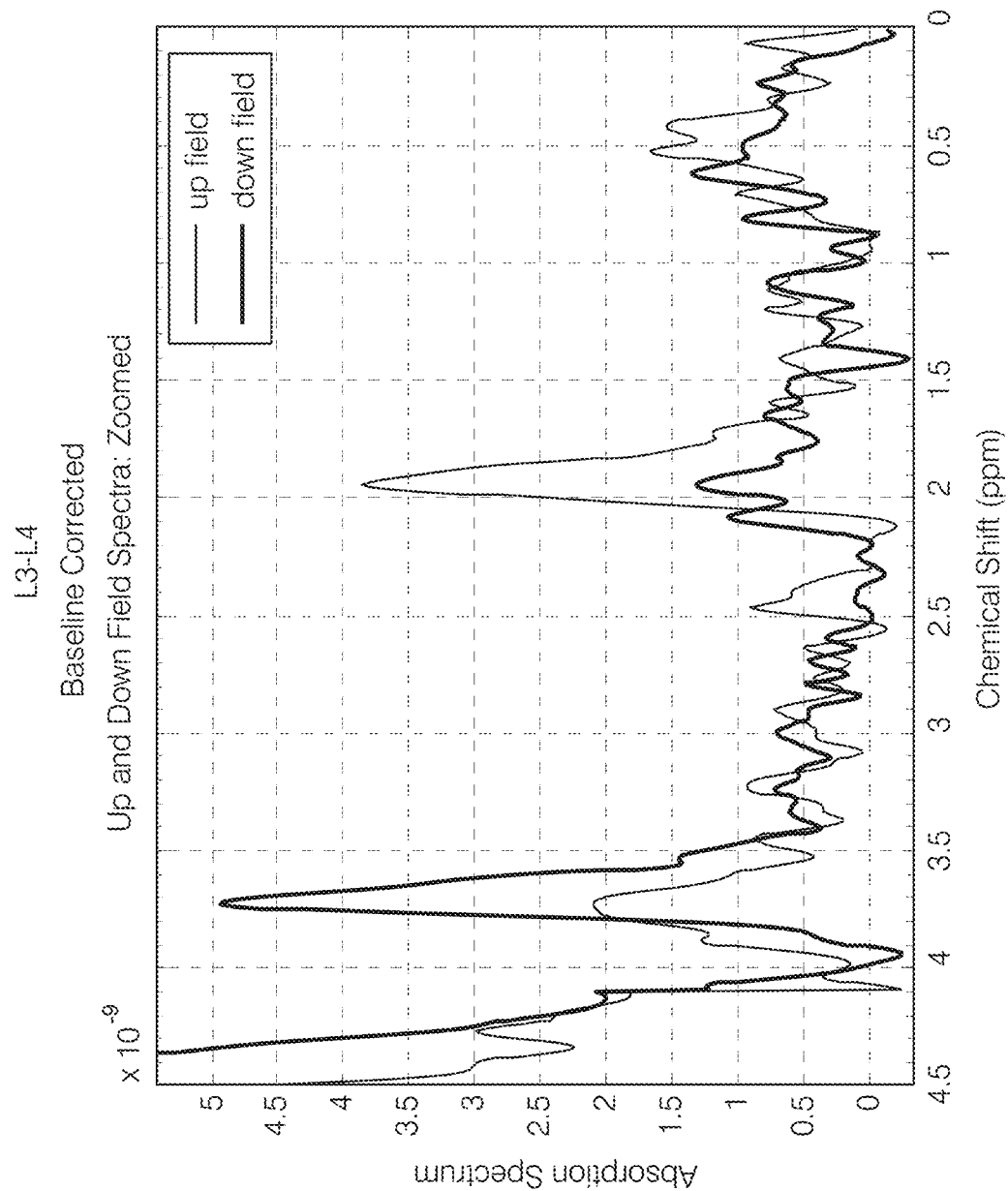
FIG. 29A shows the overlaid spectra post-fine alignment under Example 3 shown in FIG. 28B, after baseline correction, in zoomed metabolite spectrum range.
Figure 29B:
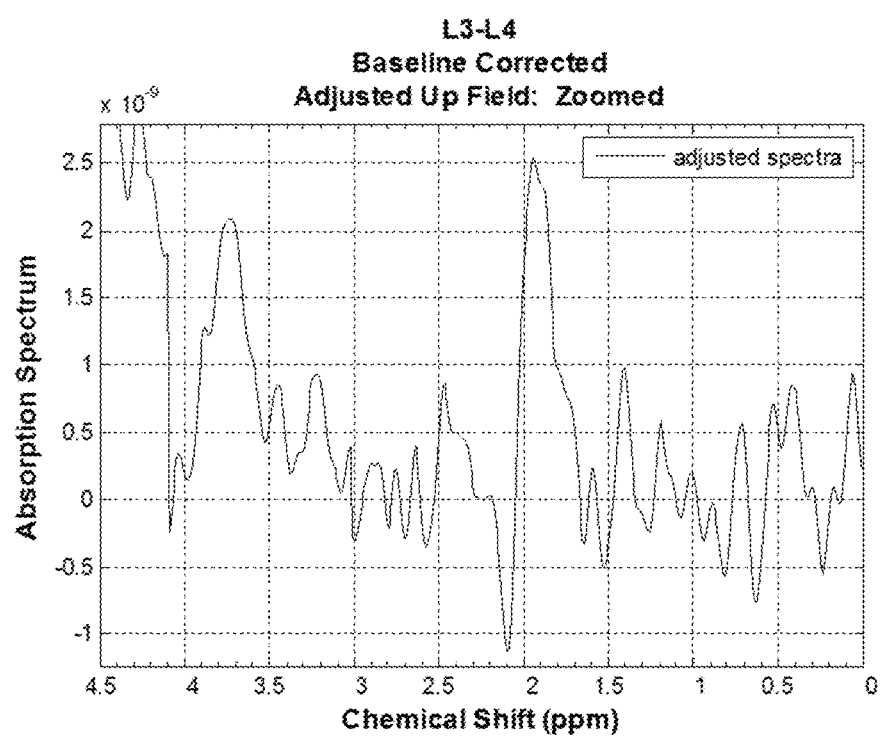
FIG. 29B shows an adjusted spectrum result under Example 3 after subtracting the fine aligned baseline corrected spectra shown in overlay in FIG. 29A, and after baseline correction, in zoomed metabolite spectrum range.
Figure 30A:
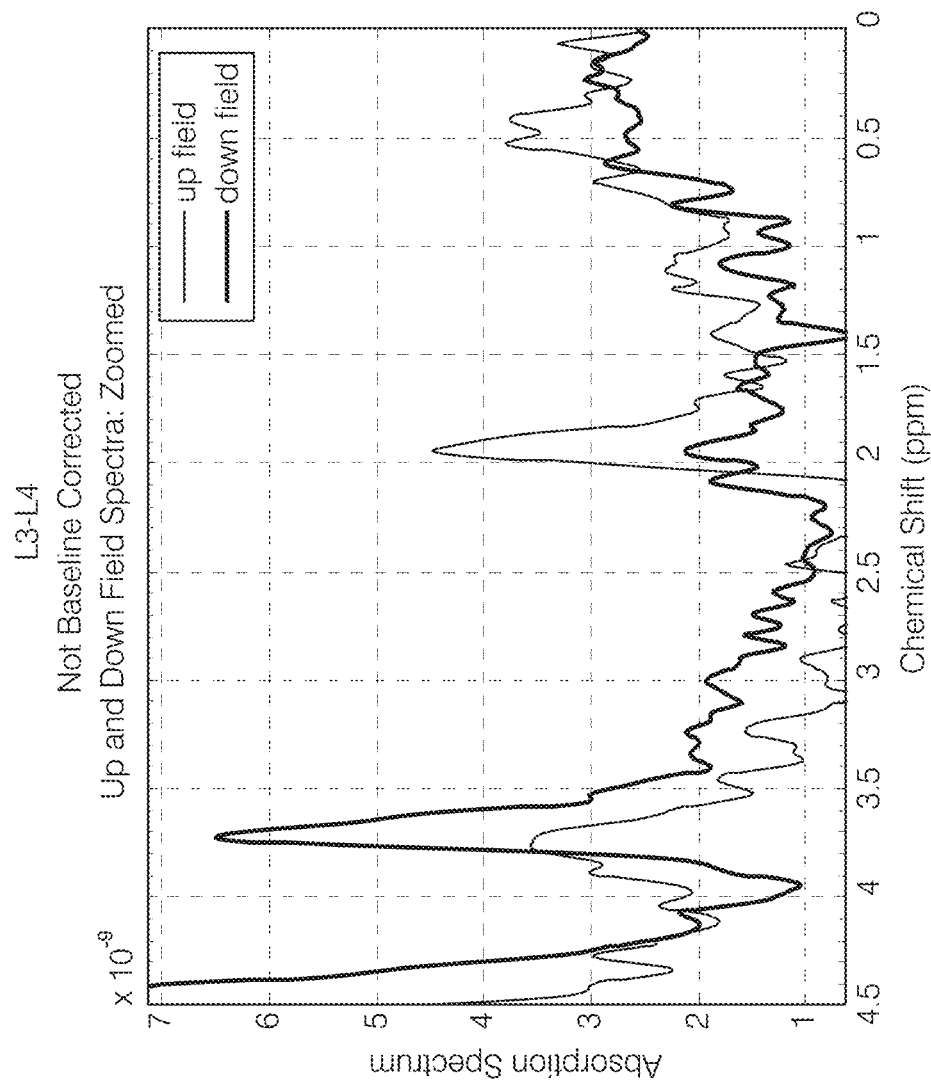
FIG. 30A shows overlay plot of the Example 3 spectrum and reflected downfield spectrum, without baseline correction, in zoomed metabolite range.
Figure 30B:
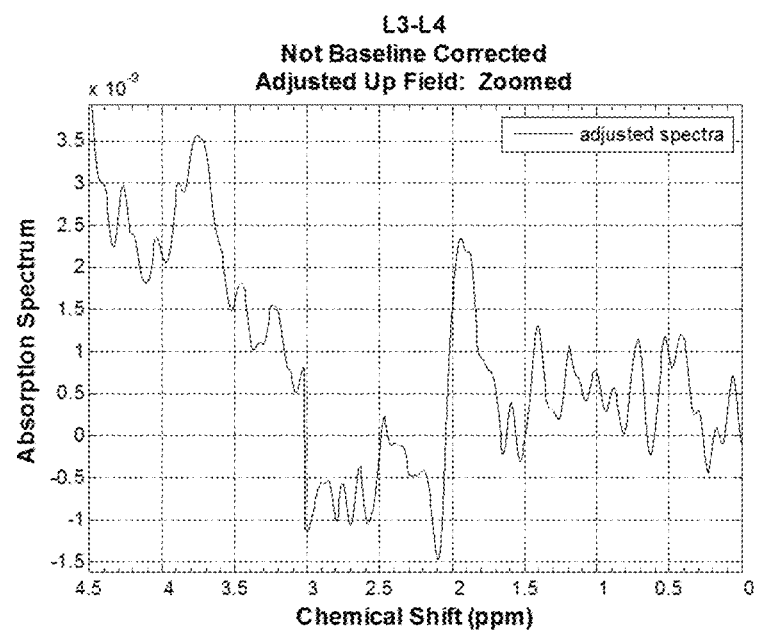
FIG. 30B shows an adjusted spectrum derived after subtracting the reflected from the upfield spectra shown in FIG. 30A, post-fine alignment but without baseline correction, in zoomed metabolite spectrum range.
Figure 30C:
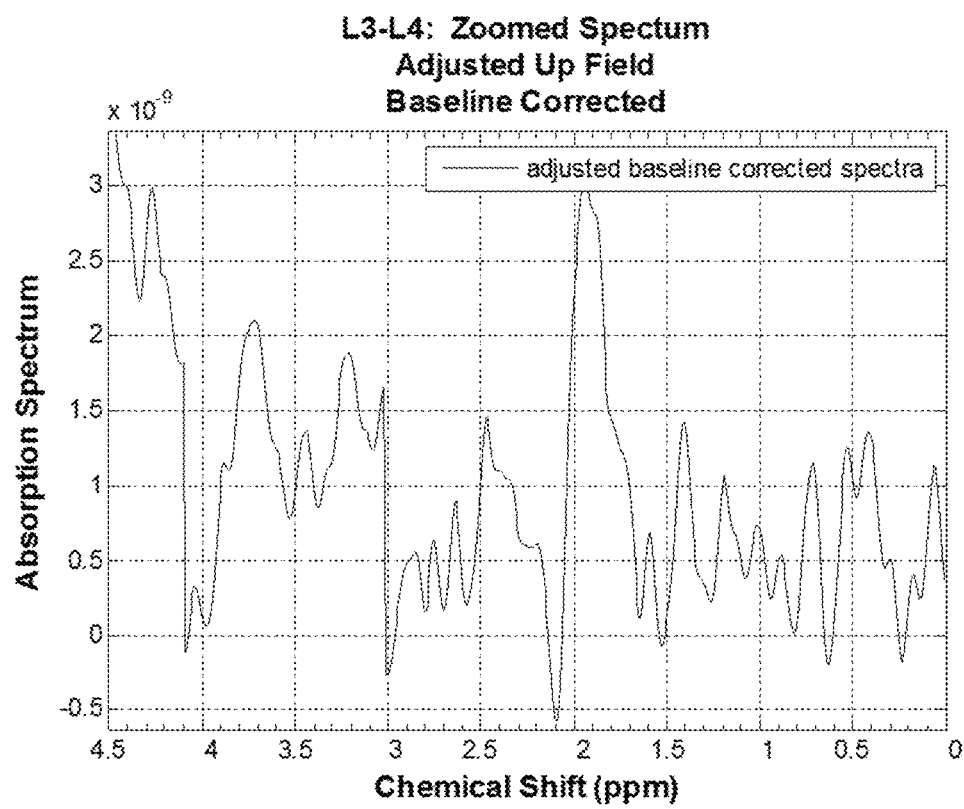
FIG. 30C shows the adjusted spectrum shown in FIG. 30B, but after baseline correction, in zoomed metabolite spectrum range.
Figure 31A:
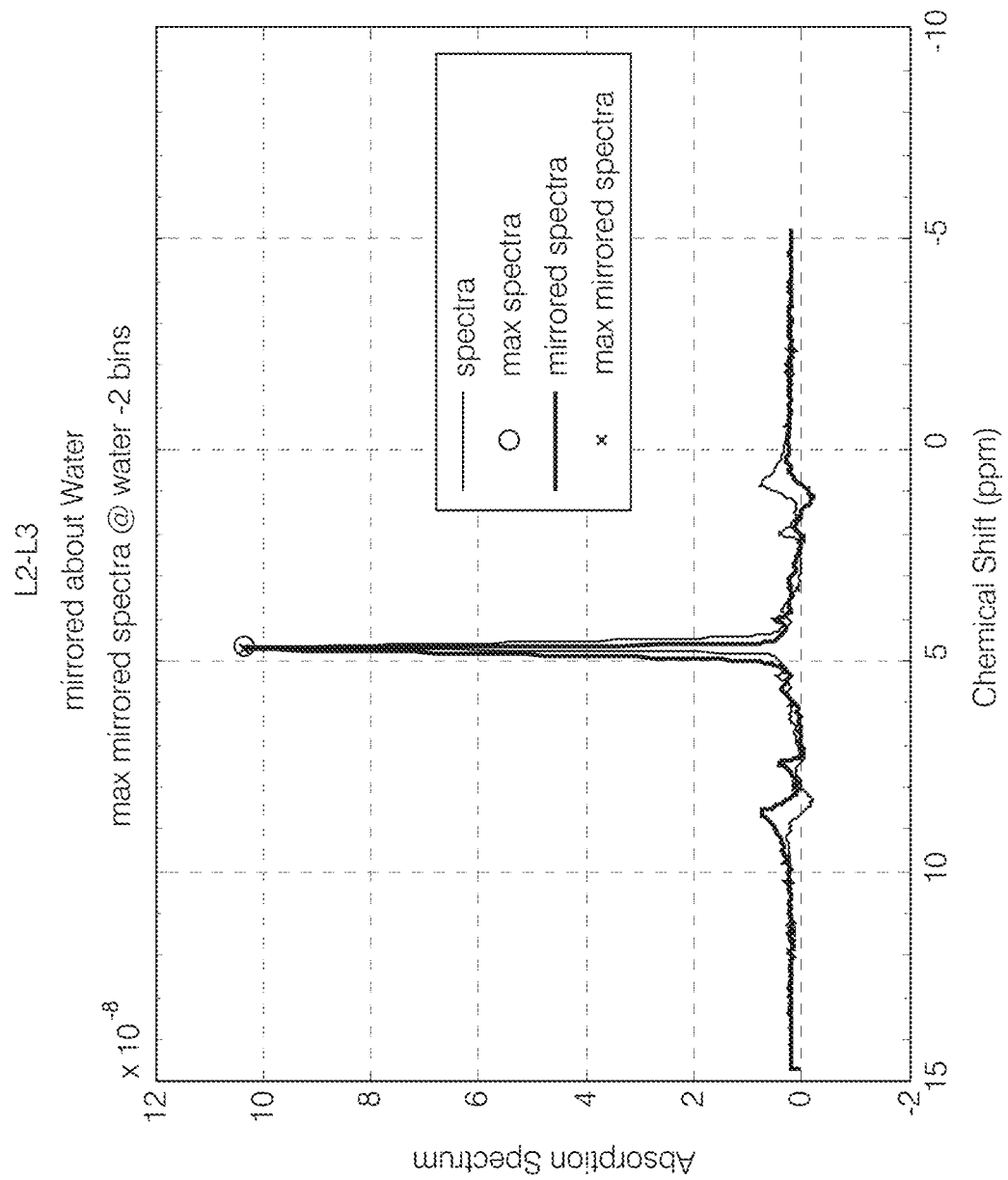
FIG. 31A shows an input spectrum and reflected spectrum thereof mirrored about water according to another Example 4, post processed (but without baseline correction or downfield adjustment), full spectrum range.
Figure 31B:
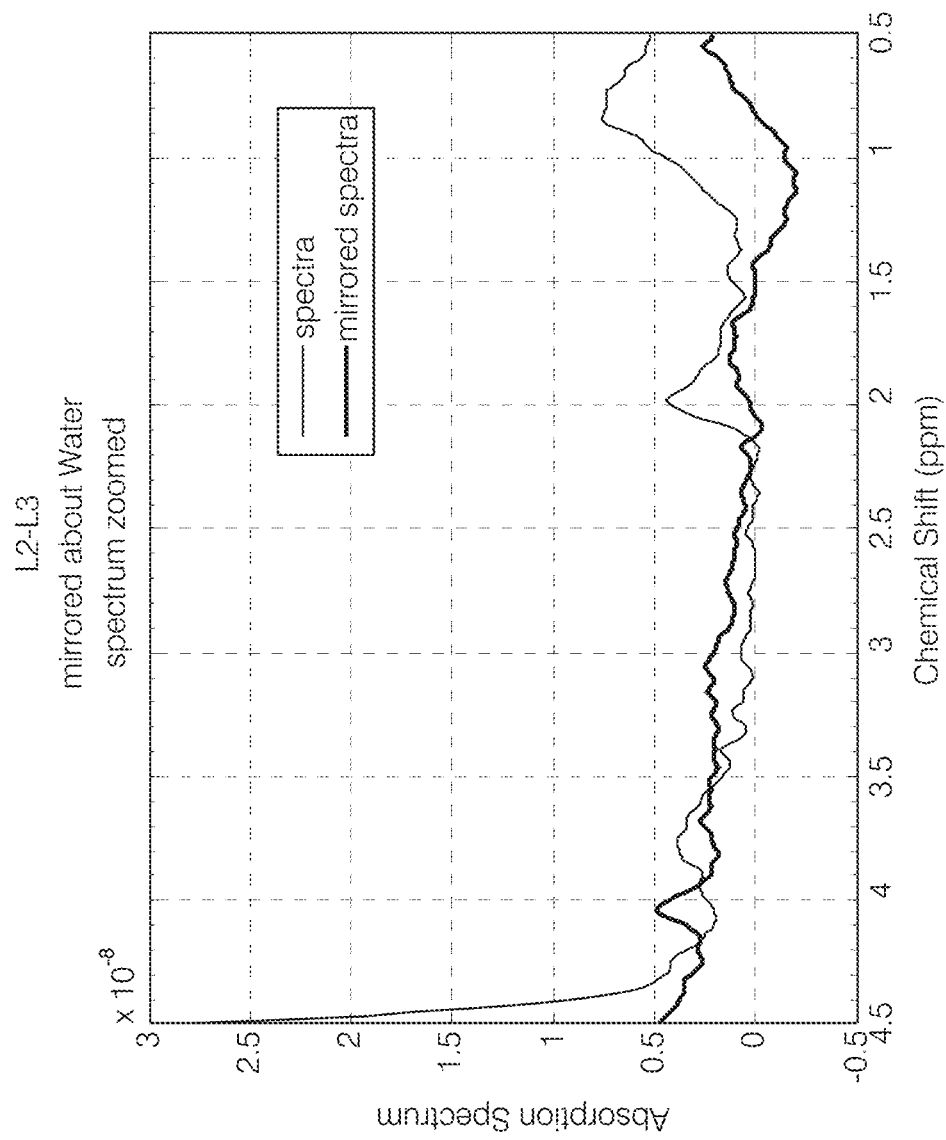
FIG. 31B shows the same input spectrum and reflected spectrum in overlay as shown in FIG. 31A, but in zoomed metabolite range.
Figure 32A:
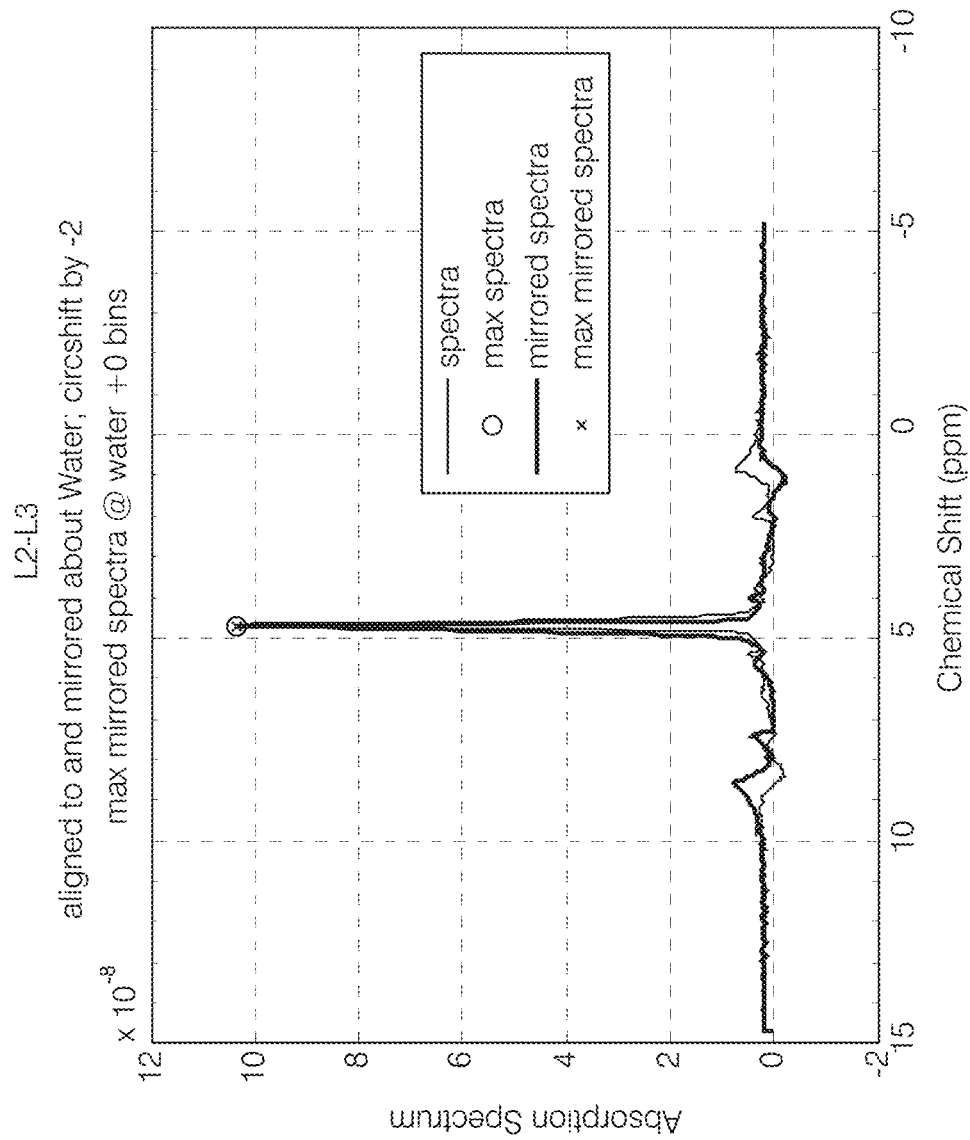
FIG. 32A shows the same overlaid spectra as shown in FIG. 31A, but after coarse alignment, in full spectrum range.
Figure 32B:
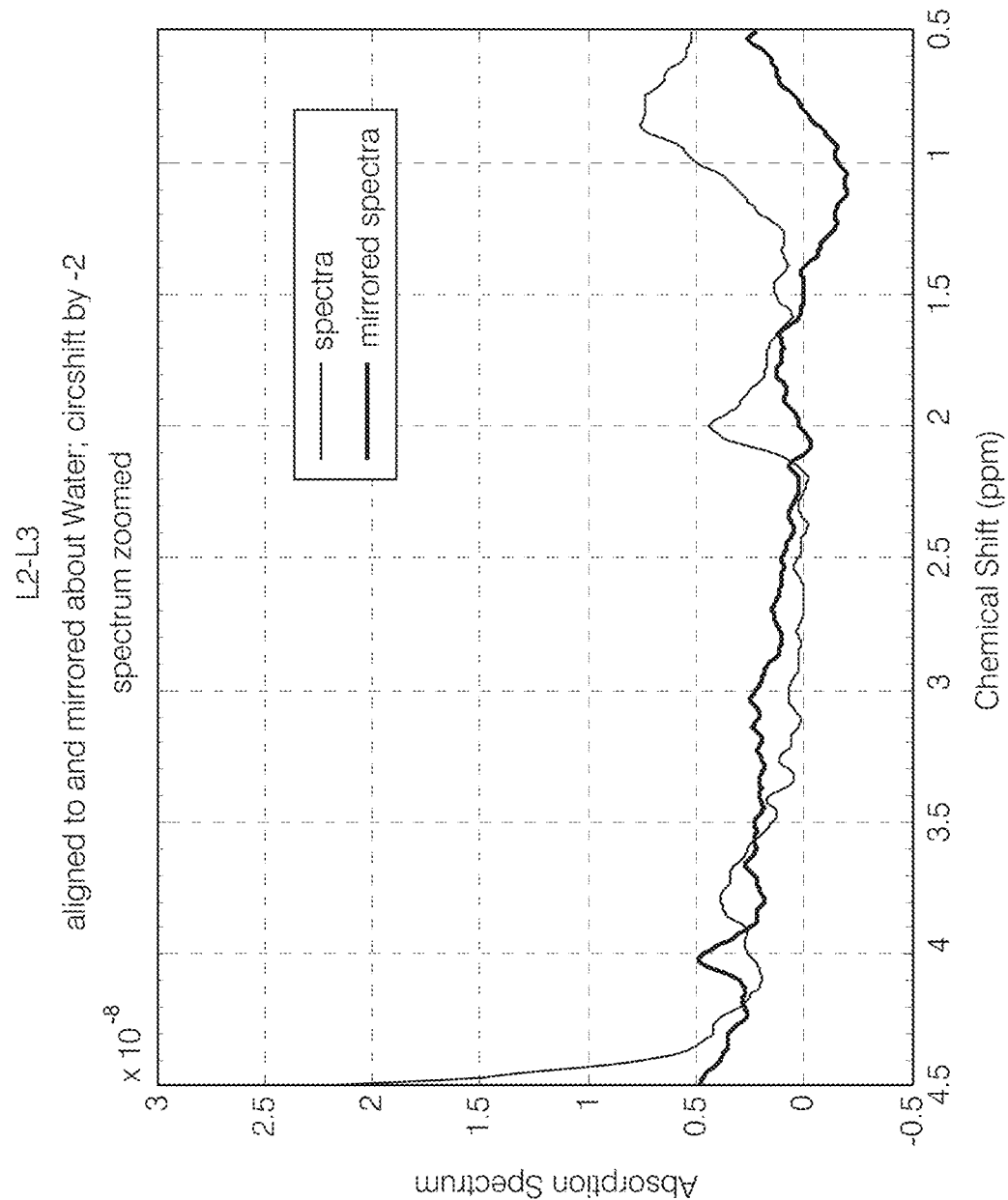
FIG. 32B shows the same spectral overlay after coarse alignment of Example 4 shown in FIG. 32A, in zoomed metabolite spectrum range.
Figure 33A:
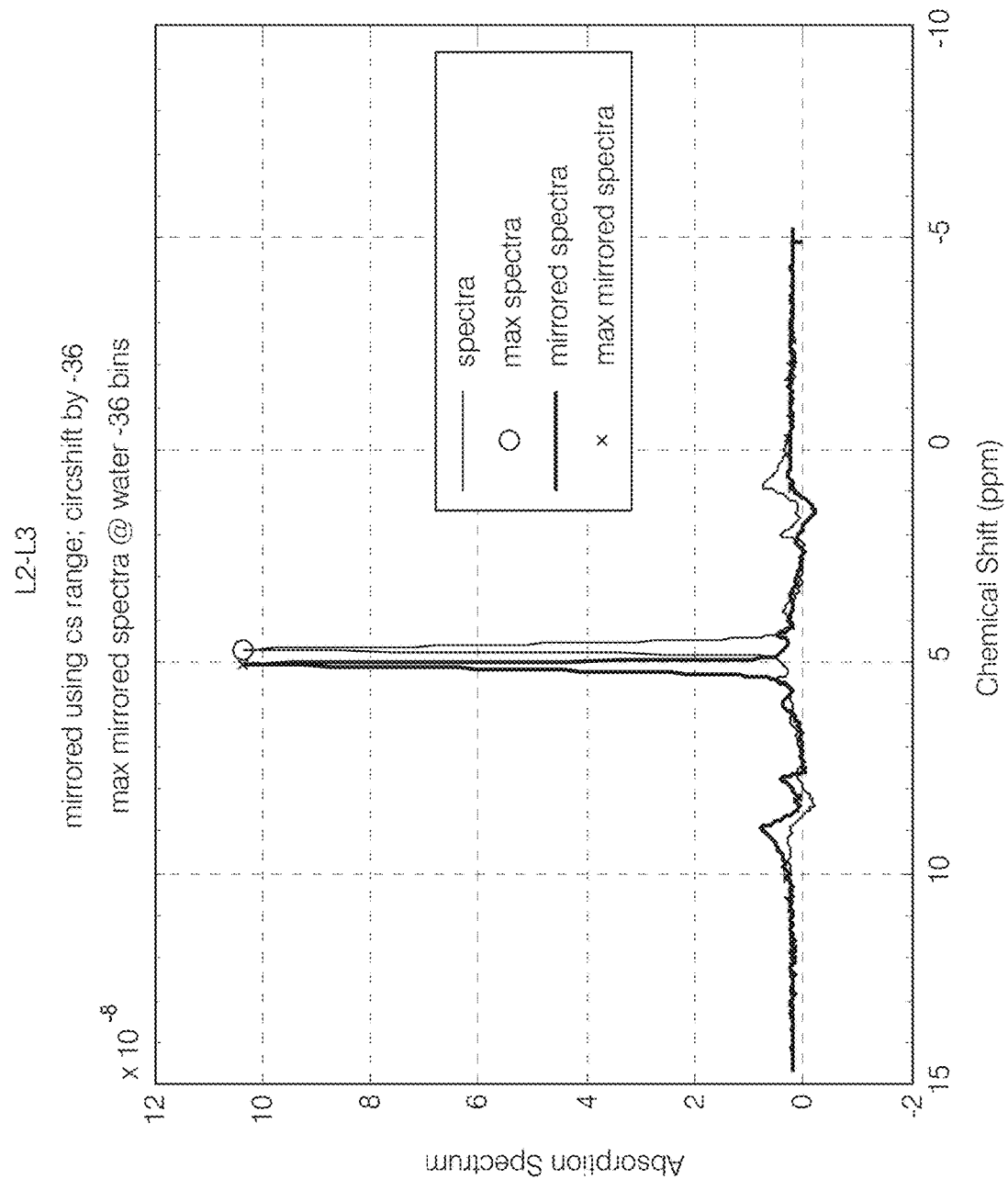
FIG. 33A shows the same overlaid spectra of Example 4 shown in FIG. 32A, after fine alignment, in full spectrum range.
Figure 33B:
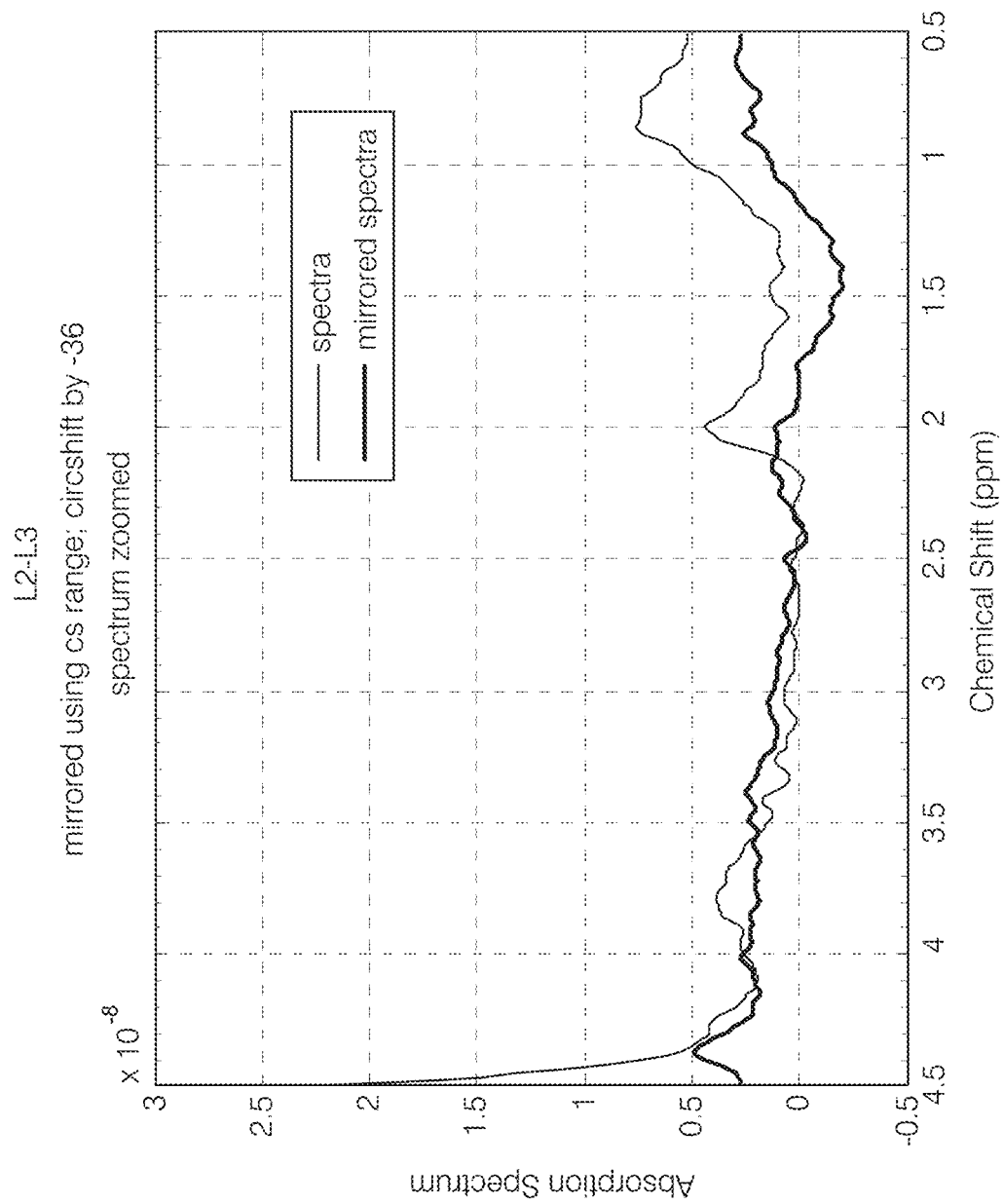
FIG. 33B shows the same overlaid spectra of Example 4 shown in FIG. 33A, in zoomed metabolite range.
Figure 34A:
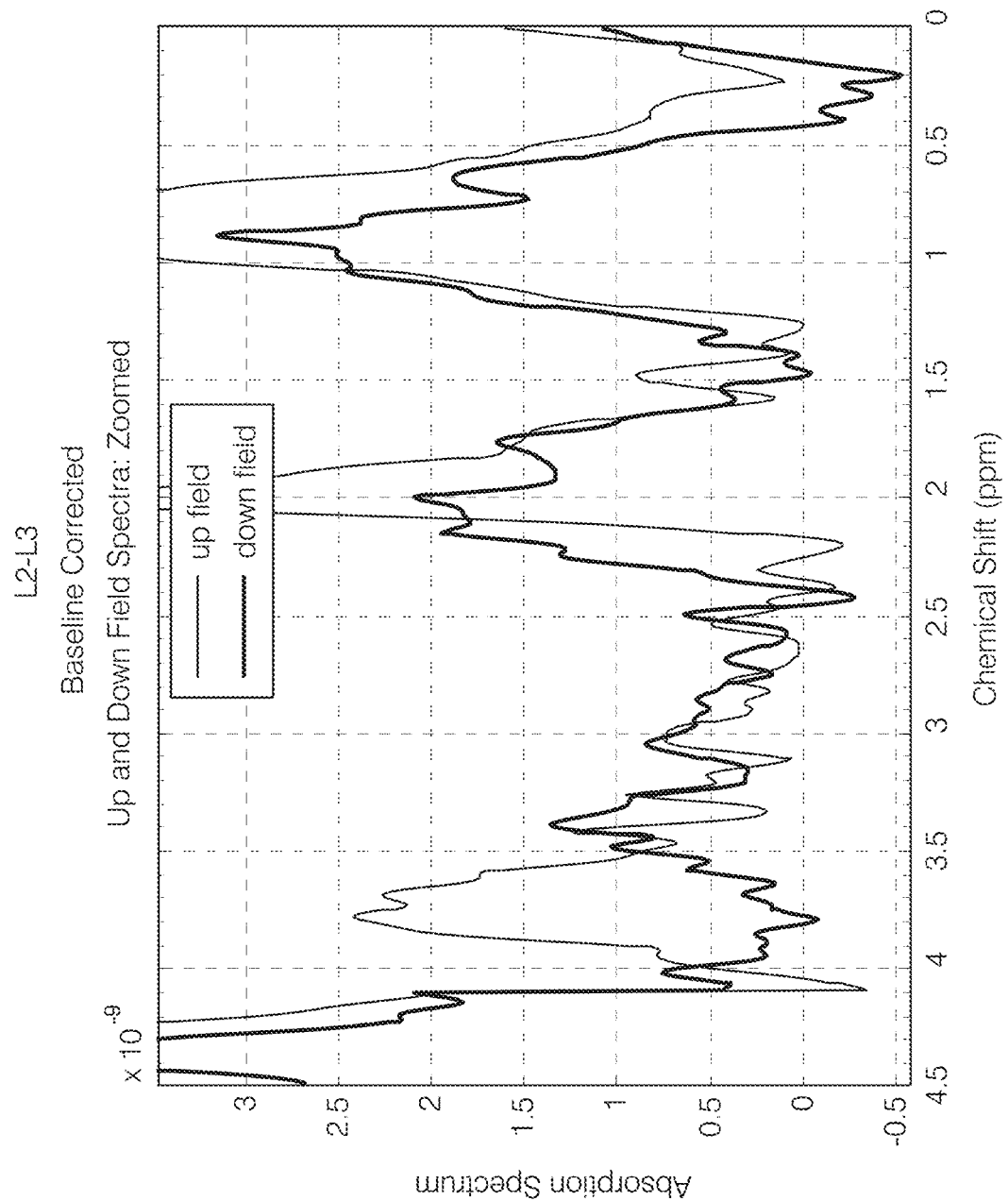
FIG. 34A shows the same overlaid spectra of Example 4 shown in FIG. 33A, each after baseline correction, in zoomed metabolite spectrum range.
Figure 34B:
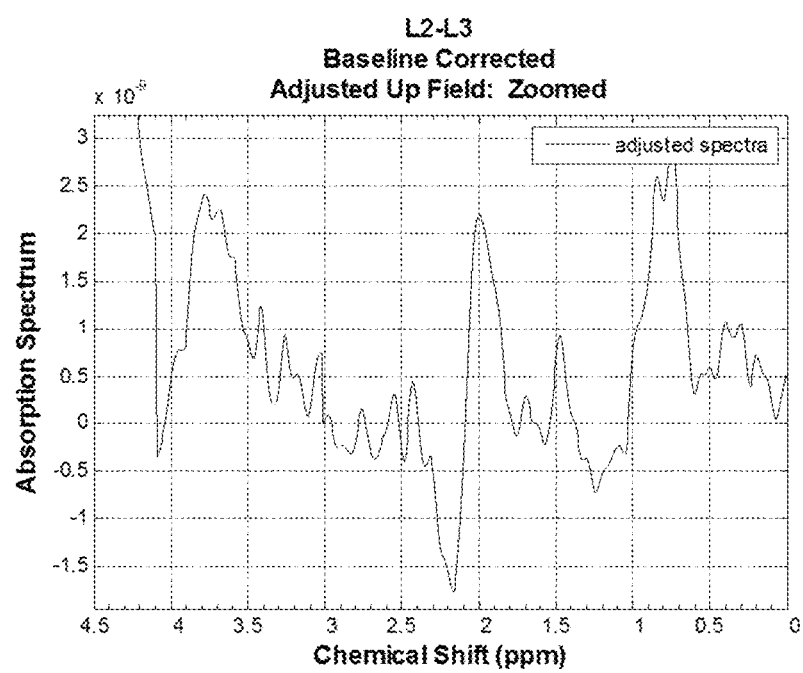
FIG. 34B shows an adjusted spectrum of Example 4 after subtracting the fine-aligned, baseline spectra overlaid in FIG. 34A, zoomed metabolite range.
Figure 35A:
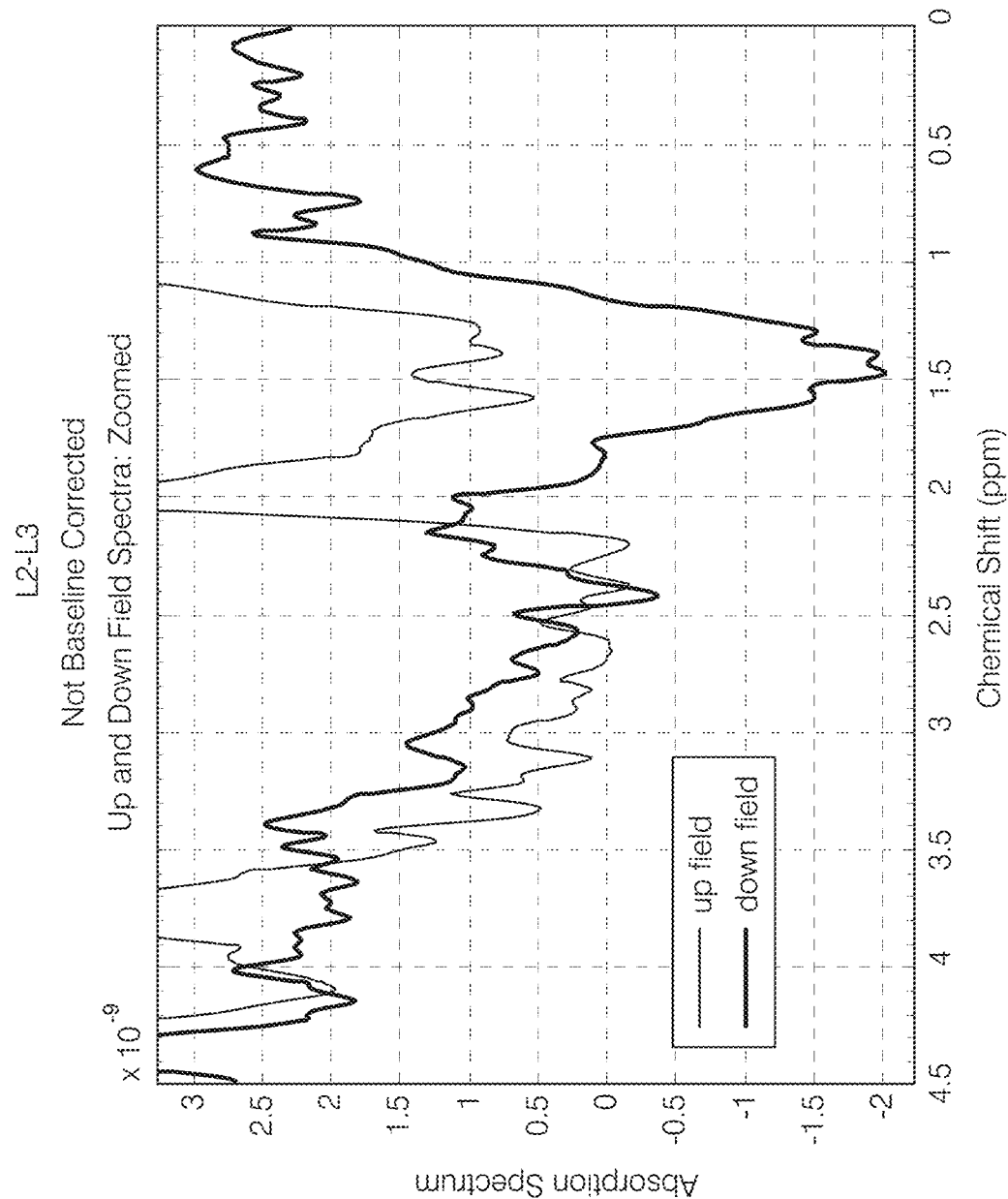
FIG. 35A shows a graph overlay of reflected downfield vs. upfield spectra of Example 4, post-fine alignment, but without baseline correction, in zoomed spectrum range.
Figure 35B:
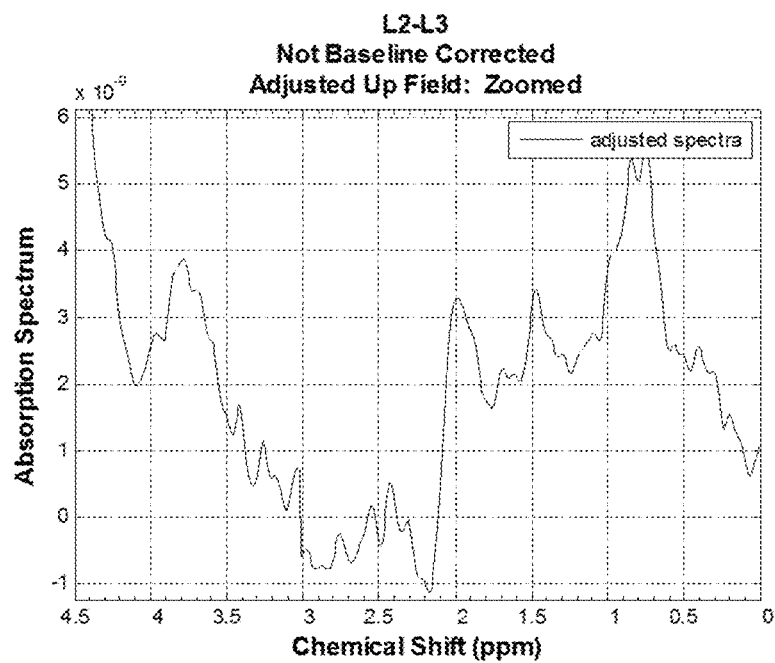
FIG. 35B shows adjusted spectral results after subtracting the overlaid spectra shown in FIG. 35A of Example 4, without baseline correction, zoomed metabolite spectrum range.
Figure 35C:
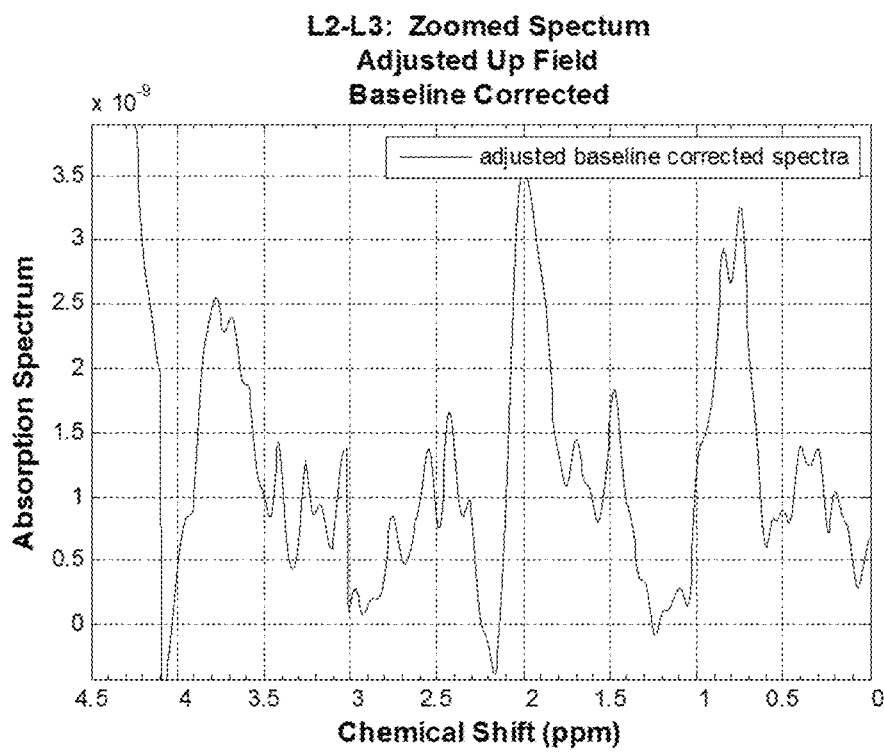
FIG. 35C shows the same adjusted spectrum as shown in FIG. 35B under the Example 4, but after post-adjustment baseline correction, in zoomed metabolite spectrum range.
Figure 36:
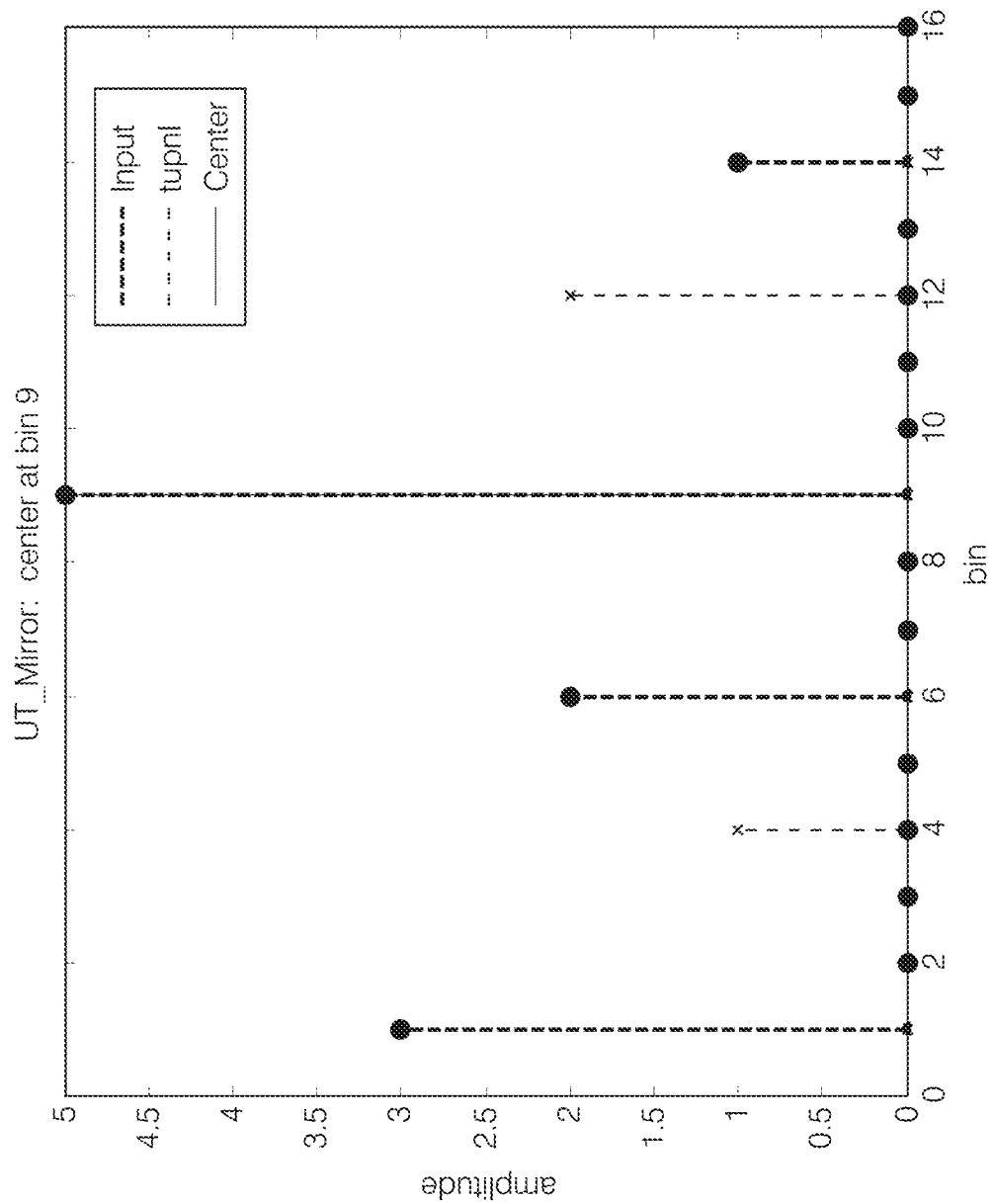
Figure 37:
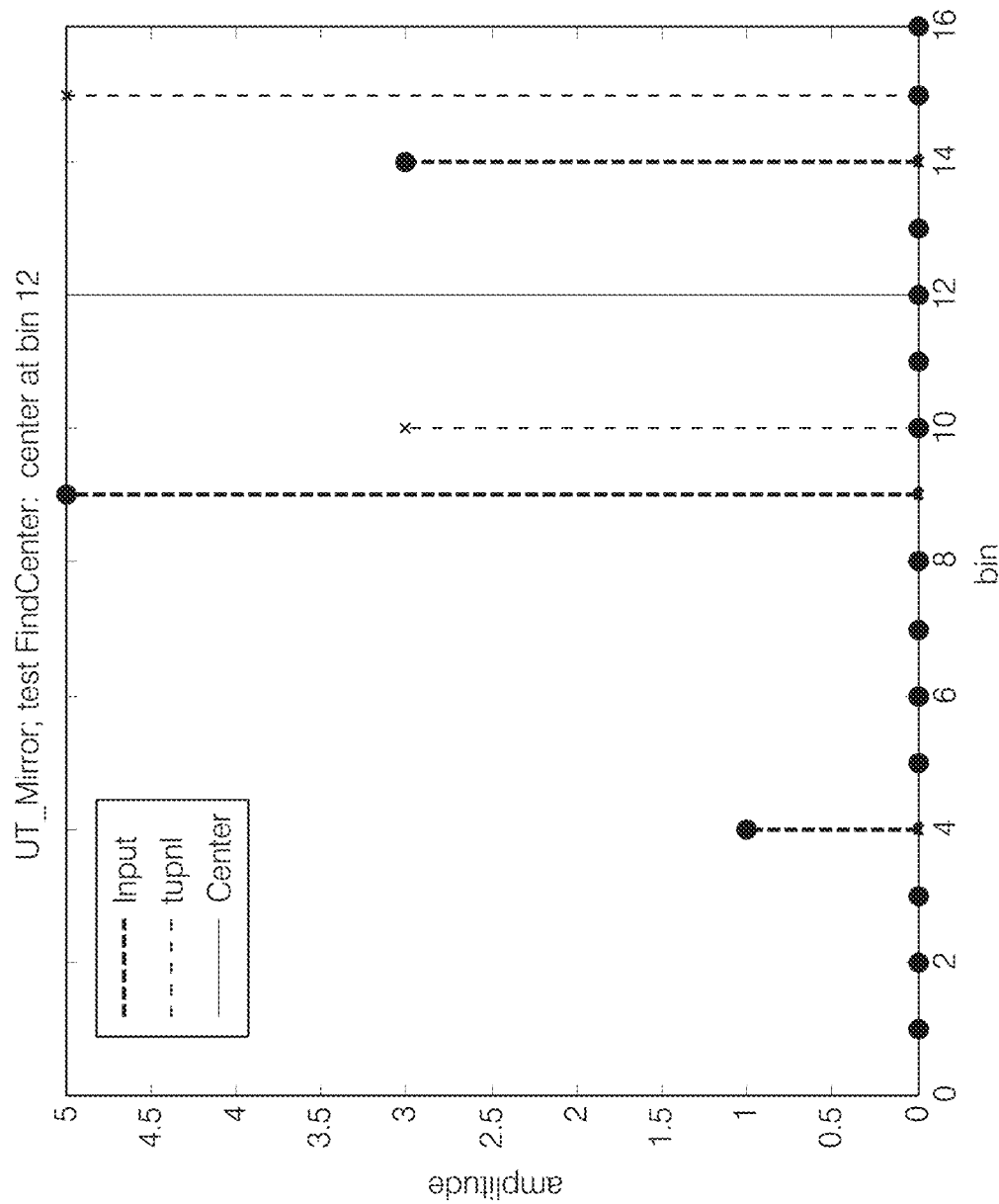

FIG. 28 shows the results of a test around bin 12, with center finding function validated.

VIII. MRS Pulse Sequence Protocol—Water Suppression & Shimming

Another aspect of the present disclosure provides certain enhancements to an MRS pulse sequence protocol for optimally acquiring robust spectra in clinical applications, and considered to be particularly beneficial in single voxel spectroscopy (SVS)(though also applicable to multi-voxel), and in particular to MRS acquisitions in relatively small voxels, and still more particularly in musculoskeletal joints. This is especially beneficial with respect to MRS performed in intervertebral discs and furthermore in particular in such discs of discogenic low back pain patients where MRS may be deployed for Dx purposes to help identify painful versus non-painful discs.

Water varies dramatically in intervertebral discs, in particular between normal healthy discs and degenerated discs. Accordingly, in discogenic low back pain patients in particular, a wide range of water signal power may be found, including between discs of the same patients. As water is used in certain MRS analysis, and processing, this water variance between discs, and water suppression approaches that may be uniformly appropriate, can be an issue. More specifically, in highly hydrated discs, such as normal discs, water content is obviously high. No water suppression used in MRS pulse sequence studies of such discs may result in water signal that is too strong and may overshadow the metabolite ranges of interest via "tails" of the water signal. In highly desiccated (dehydrated) degenerated discs, water content is obviously low. Water suppression may remove any water signal that may exist, thereby to the detriment of any processing or analysis approaches relying on water signal.

Accordingly, one aspect of this disclosure provides an MRS pulse sequence exam configuration and protocol that comprises a degree of water suppression that is set to "moderate" suppression (e.g. between full suppression and no suppression). This may be achieved, for example, for a third flip angle in a CHESS/PRESS MRS pulse sequence of about 60 to about 120 degrees, and in particular about 85+/−10 degrees. It is to be appreciated though that the appropriate exact settings may vary between MR system and from different vendors, per different considerations in their overall operation and also specific water suppressions approaches employed. However, in general, such moderate suppression has been observed to be appropriate in the most cases. Nonetheless, even this has been observed to be inappropriate in other cases, as either too strong or too weak (per the situations noted above).

According to another aspect, water suppression is controlled to meet a given case. In one embodiment, a disc is evaluated as to its degree of hydration. This may be done for example via review of T2-weighted imaging, T2-mapping, or T1rho imaging and/or mapping, of the disc. Based upon the degree of hydration, a degree of water suppression is selected. For highly hydrated discs, more aggressive suppression is selected, and for less hydrated discs lower suppression is selected and set, for the MRS exam configuration and protocol customized to that disc. This may be done automatically, such as via a look up table correlating hydration metric to water suppression level, or manually (either by the same process, or otherwise).

Another issue observed with water suppression is the range upon which it is applied. This may be for example 50 Hz (e.g. in case of 3 T), or 25 Hz (e.g. in the case of 1.5 T). While such range is typically provided in default setting around an expected "zero" center line for water (about 4.7 ppm in the CS spectrum), this does not always function as intended. In particular, water side lobes may result outside of that range post-suppression—giving rise to issues noted above with respect to such lobes providing additive artifact in other metabolite ranges of interest outside of the water suppression band. This is in particular the case where there is a wide water line resulting from an inadequate shim. A combination of a broad shim, and narrow water suppression band, has been observed to produce compromised spectra believed to be due to this phenomena. Many MRS pulse sequence protocols are configured and conducted using only automatic shimming. However, this is based upon certain defaults that are not always sufficient, in particular in the high susceptibility area of the lumbar spine for example. Observation of this in the clinical environment has been further observed to result in the issues noted above.

Another detrimental effect of the relatively narrow water suppression pulse is that it can introduce a bias error in the frequency shift estimator. The spectral shape of the water suppression pulse is typically Gaussian; the spectral shape of the residual water shape is similar. When the water signal falls on the slope of the water suppression signal, the spectral shape of the water is distorted and its apparent peak, as sensed by the frequency shift estimator, will not be its true energy peak. This effect is mitigated by the more gentle slope of a wider water suppression pulse.

According to another aspect of this disclosure, an MRS pulse sequence acquisition configuration and protocol provides for a manual shim, which may be a default approach for the pulse sequence or override in settings where autoshim is insufficient. This has been observed to overcome the shortcomings of the default autoshim in many lumbar disc acquisitions, providing more robust results and often avoiding the interrelated issues noted with respect to wider water peaks and a fixed water suppression band.

Another aspect of this disclosure is an MRS pulse sequence acquisition configuration and protocol which provides for wider water suppression. As opposed to the typical bands noted above, increasing these is believed, and has been observed in certain clinical cases, to provide improved results with respect to reducing water suppression side lobe artifacts, though while not compromising metabolite regions of interest. According to one embodiment, the water suppression band is set to more than about 50 Hz (for 3 T), and more than about 25 Hz (for 1.5 T). In one further variation of this embodiment, the band is set to no more than about 100 Hz (for 3 T) and no more than about 50 Hz (for 1.5 T). In still a further variation, it is set to about 75 Hz (for 3 T) or about 37.5 Hz (for 1.5 T). These values are considered reached within about +/−10 Hz. Specifically, settings of 75 Hz and 100 Hz are both expected (and have both been observed in limited cases tested) to provide robust resulting spectra for highly hydrated discs with strong water signal, and without compromising spectral ranges of interest including preserving robust carbohydrate signal (which is particularly exposed as closer to water, e.g. up to about 3.5 ppm), and without appreciable side lobe artifact of note.

Notwithstanding these ranges as potential limits, however, even these ranges can expand in certain circumstances. For example, where metabolites further outside of water are not necessary for a particular measurement purpose, the bandwidth can expand to ensure no water artifact while still preserving other spectral peaks further away. For example, if NAA (e.g. proteoglycan) and/or metabolites to its right (e.g. hypoxia metabolites, e.g. lactic acid and/or alanine, or lipids, etc.) are of interest, and other data between the NAA peak region (around 2 ppm) and water (around 4.7 ppm) are not needed, water suppression bandwidth can extend much wider than these limits up to a span that would compromise the NAA signal region.

While this aspect of increased water suppression band is believed to provide a robust solution, in particular for disc MRS (and especially lumbar), a further embodiment of the present disclosure provides for an adjustable water suppression band in custom manner to accommodate a given test case. According to one further more specific embodiment, the band is adjusted based upon the value of at least one parameter of the water signal, such as for example peak amplitude and/or FWHM of the shim result. According to another more detailed embodiment, a default water suppression band setting is used for an initial acquisition sufficient to evaluate the result and determine an appropriate adjustment for the setting. This may relate to a "trial and error" approach around certain desired result. In still another more particular embodiment, the downstream field of the spectrum is analyzed for peaks considered to be side lobe artifacts of suppression. The suppression is adjusted to a value to reduce this artifact. Other metrics, such as upfield effects, may also be used (either alone or in combination).

IX. MRS Diagnostic Processing—Intervertebral Discs

Other aspects of the present disclosure provide certain new and improved systems and methods for diagnostic interpretive processing of MRS spectral information from MRS spectra that are post-processed (such as for example according to one or more, or all, of the various signal processing aspects disclosed herein) from MRS pulse sequence applications and induced signal acquisitions in and from intervertebral discs, respectively.

One such aspect measures one or more parameters (e.g. peak height, area under the curve or AUC, FWHM, etc.) for n-acetyl (NAA) and carbohydrate (CA) peak regions, and computes a ratio therebetween. According to one mode of this aspect, this ratio is combined with at least one additional ratio comprising such measurements for at least one of these regions and a second measurement comprising the lactic acid region (LA). In one embodiment of this mode, the second measurement comprises the combined lactic acid and alanine (AL)(together "LAAL") region. The multiple relative ratios between these several peak regions are provided in relative context, which is expected to provide diagnostic value in certain cases, such as for example in diagnosing degenerative disc disease and/or discogenic low back pain based there upon and via the uniquely induced MRS pulse sequence signals acquired, post-processed, and measured (such as according to the various other embodiments herein disclosed).

Another aspect of this disclosure calculates a "peakiness" value for the carbohydrate region, which is believed to relate to degree of complex carbohydrate breakdown into constituent component molecules. This is done according to one mode by curve fitting the region and calculating a correlation coefficient therefrom. This calculated measurement may also be used, either alone or in combination with other metrics, in a manner useful for assisting in diagnosing disc disease or pain.

It is also appreciated that each such measured spectral feature may provide valuable information on its own and without necessarily being required to be taken in combination with other features (such as per the illustrative embodiments described herein). Moreover, other chemical regions may be of diagnostic interest in certain applications, also either alone or in various combinations, as would be apparent to one of ordinary skill.

IX. Phase Group Processing & Combinations of Embodiments

The following reference is herein incorporated in its entirety by reference thereto: Bolan, Patrick J., et al., "Measurement and Correction of Respiration-Induced $B_0$ Variations in Breast $^1H$ MRS at 4 Tesla," Magnetic Resonance in Medicine 52:000-000 (2004).

Additional embodiments including phase step cycling of MRS serial frame data acquisition and related processing, and certain combinations of various embodiments herein described, are further disclosed as follows. An MRS system is configured to perform an MRS spectral acquisition with phase changes stepped along a cycle corresponding to a sub-set of sequential FID frames. This is typically repeated over the course of the acquisition, such that the total number F of FID frames in the acquisition divided by the number of steps S in the cycle will typically be equal to a whole number. A post-processor is then configured to post-process FID frames comprising similar phase steps within "groups", though the result of which processing may be later combined for further processing.

MRS systems will frequently employ phase cycling, wherein serial acquisition frames are stepped through different phases. These are typically done by even numbers of "phase groups" across the acquisition series. Certain additional present embodiments that are considered advantageous, although not necessary in all cases, integrate frequency shift estimation (& subsequent correction) and frame selection with phase group processing. The broad scope of the present disclosure contemplates a variety of approaches for this beneficial processing method (and related systems and processors), as would be apparent to one of ordinary skill.

One particular example embodiment however integrates a spectral cross-correlation based frequency estimator with phase group processing and frame selection. These are integrated according to this embodiment for two primary reasons.

(1) The frames from each phase group contain artifact with different phasing. This artifact can introduce a phase-group dependent bias in our frequency shift estimator. For example, if one is +2 Hz and the other is −2 Hz, and the correction is applied with this bias, then when the frames are combined, the composite spectrum will be the combination of the two shifted spectra and split peaks mat result. This is avoided by frequency adjusting the groups separately, then performing an absolute frequency correction on each before combining.

(2) Frame selection can adversely interact with phase grouping. The basis of achieving artifact cancellation via phase cycling is that an equal number of frames from each phase group be combined. Frame selection can upset that balance by upsetting that equality and introducing a bias. This is avoided by having the last step be forming the mean of each phase group, and then the mean of those means. A test must be performed to verify that each group is adequately represented, otherwise, phase groups are not processed individually and all the frames are treated as if from a single phase group.

The following describes integrating a spectral cross-correlation based frequency estimator with phase group processing and frame selection. These are integrated for two primary reasons.

The frames from each phase group contain artifact with different phasing. This artifact can introduce a phase-group dependent bias in our frequency shift estimator. For example, if one is +2 Hz and the other is −2 Hz, and the correction is applied with this bias, then when the frames are combined, the composite spectrum will be the combination of the two shifted spectra and split peaks mat result. This is avoided by frequency adjusting the groups separately, then performing an absolute frequency correction on each before combining.

Figure 38:
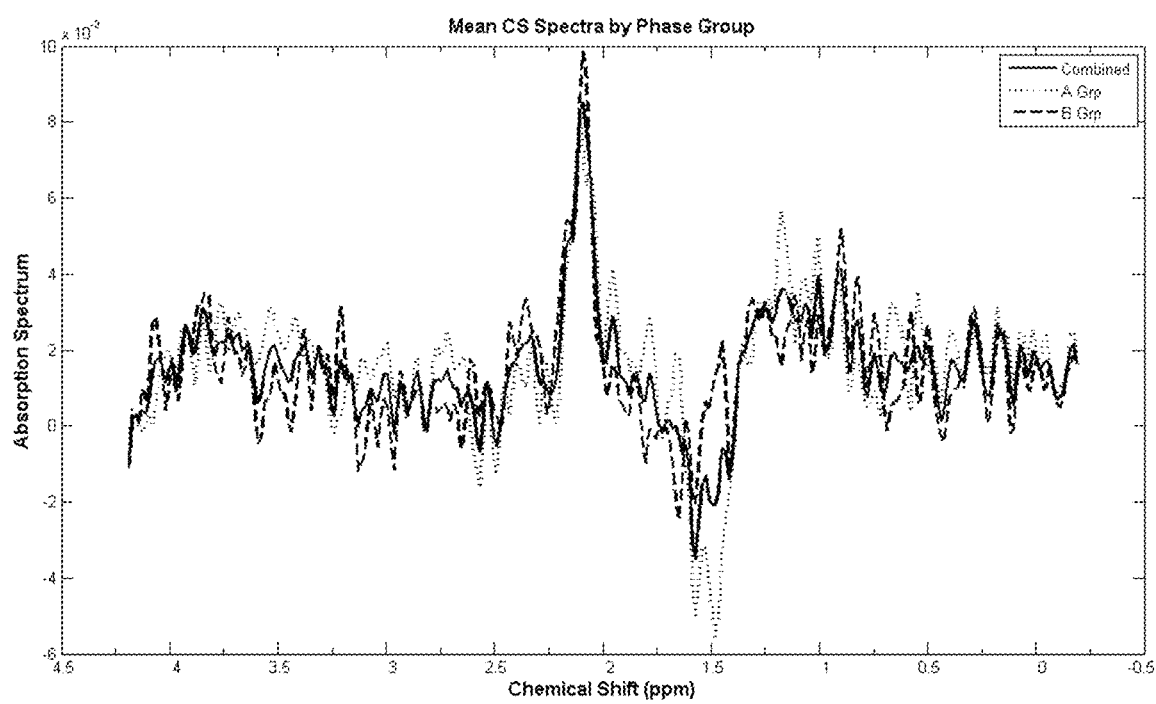

FIG. 38 shows a spectrum from a lumbar disc acquisition in overlay between multiple different aspects of the acquired data as follows. This is an example of the differences in the chemical shift spectra from a series of acquisitions with 2-step phase cycling. The dotted line is the average of 128 frames from one phase group, and the dashed line is the average of 128 frames from the other phase group. The portions of the spectra where these traces are of opposite polarity represent the artifact components that phase cycling attempts to mitigate. The solid line shows the average of these two sep"/showing the cancellation, albeit imperfect, of these artifact signals.

Figure 39:
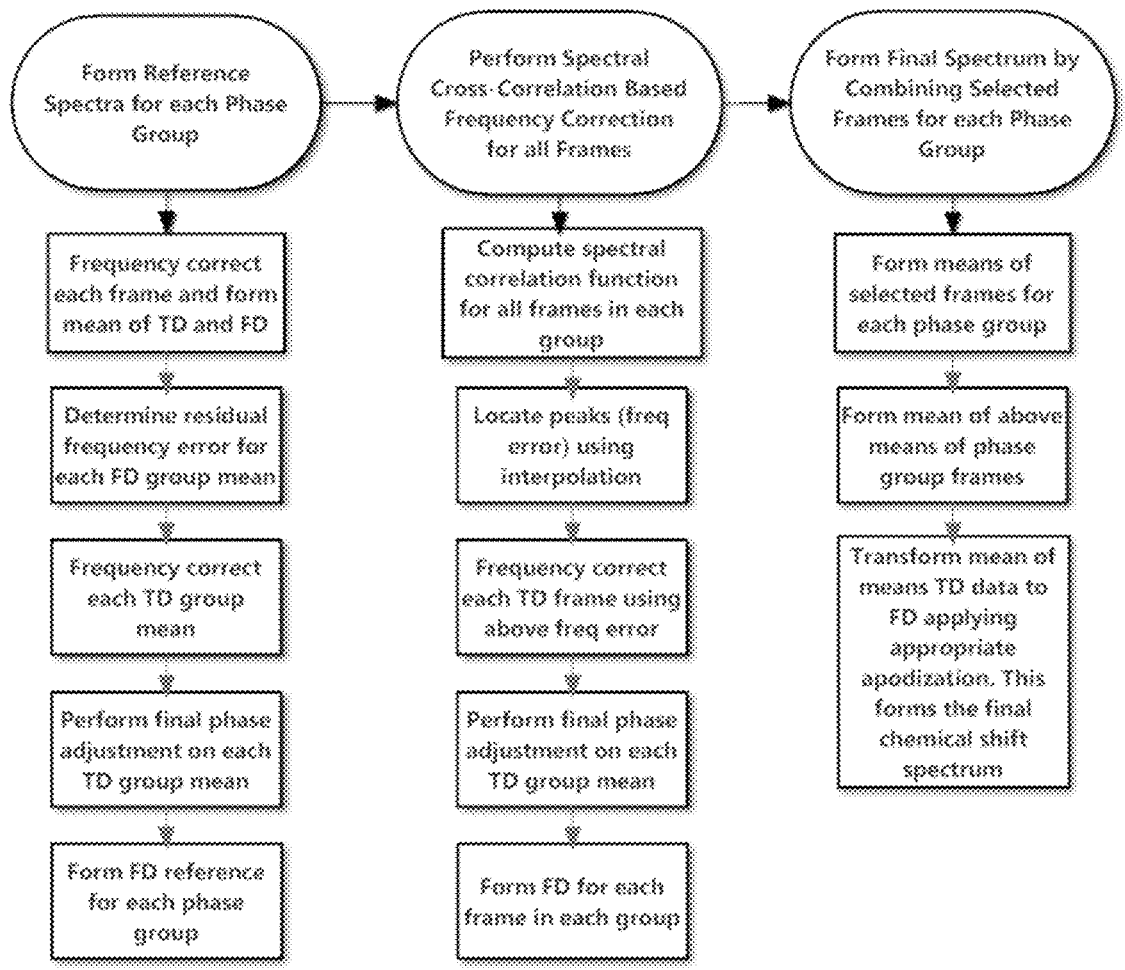

FIG. 39 shows a flow diagram of an automated method to perform frequency shift estimation and correction, and frame selection in the context of phase group processing. It uses the spectral cross-correlation method of frequency shift estimation but could be based on the spectral peak method just as well. The first step is to form reference spectra for each phase group. For the second step, all the frames from the corresponding phase group will be aligned in frequency by the spectral cross-correlation method. The third associates frame selection and phase group membership to form the mean of the frequency-corrected and frame-selected frames for each phase group, and then the mean of these means. This is performed in the time domain (TD) and then transformed, with appropriate apodization to the frequency domain (FD) to form the final chemical shift spectrum.

One step (the first step of this illustrative embodiment) is represented in the first column of FIG. 39 and is to form the reference spectra for each phase group. Within this process, a first sub-step comprises frequency correcting each qualified frame by aligning the spectral peak to zero in the complex frequency domain, and to form the TD and FD means for each group. The next sub-step is to perform interpolated spectral peak frequency shift estimation to determine the residual frequency error. This is done using cubic spline interpolation to increase the precision of the estimate by a factor of 10, for example. This frequency error estimate is then used to correct the frequency of the TD mean for each group. Because the preceding operations may have resulted in a small phase shift, a final fine-grain phase adjustment is performed in the TD. The final FD reference data is formed and both the TD and DF references for each phase group are available for spectral cross-correlation based frequency correction. Invoking the function "makePh-GrpRef.m" in MATLAB, the commercially available processing utility by MathWorks, teaches how this is mechanized.

Another step, and which is step 2 of the particular illustrative embodiment shown, is represented in the second column of FIG. 39, performs frequency correction using the spectral cross-correlation method on all frames. The first sub-step is to compute the complex spectral cross-correlation coefficient function between each frame and its corresponding group reference. This is done for a specified number of lags, which may be typically for example about 200 for data from about a 3 Tesla system, sufficient to accommodate the largest frequency (for example about 50 Hz) shifts anticipated. Next, the correlation data is evaluated to locate the peak of the real part of the complex correlation function. Cubic spline interpolation is employed to increase the precision by a factor of about 10 and the interpolated lag of the peak is expressed as a frequency shift in Hz. Next, the frequency shift estimation just determined is used in performing frequency correction on the corresponding TD frame. The final step is to form the FD data for each frame in each phase group. The MATLAB functions freqAdjSC.m, spectCorr.m, spectCorrInterp.m and cmnFreqAdjTD.m teach how these operations are mechanized.

Another step, which is step 3 in the illustrative embodiment shown, is represented in the third column of FIG. 39, and comprises forming the final spectrum by first combining the qualified frames by group in a manner to avoid introducing phase group cancellation bias due to the frame selection process. The mathematical means (or averages) of qualified TD frames for each phase group are formed and then the mean of these means is computed. This provides the final (unless further steps are desired) composite TD data from which the final chemical shift spectrum is formed by applying appropriate apodization and transforming to the FD.

FIG. 39 shows a software flow diagram 500 of an automated method to perform frequency shift estimation and correction, and frame selection in the context of phase group processing. It uses the spectral cross-correlation method of frequency shift estimation but could be based on the spectral peak method of other approaches, including other embodiments elsewhere herein described, just as well. The first function 510 is to form reference spectra for each phase group. All the frames from the corresponding phase group will be aligned in frequency by the spectral cross-correlation method 520. The last step 530 associates frame selection and phase group membership to form the mean of the frequency-corrected and frame-selected frames for each phase group, and then the mean of these means. This is performed in the time domain ("TD") and then transformed into frequency domain ("FD"), with appropriate apodization applied to the FD used to form the final chemical shift spectrum (or interim aggregate spectrum as the case may be, to the extent other additional post-processing may be done, e.g. baseline correction, other filtering, curve fitting, etc.).

To form the reference spectra for each phase group 510, the first step 511 according to the current illustrative embodiment is to frequency correct each "qualified frame" (frames which have passed frame editing as "selected" vs. "excluded" frames) using the peak grabbing & location estimation method (such as for example, but not limited, according to other embodiments herein disclosed). That is used to form the TD and FD means (e.g. averages) for each phase group. The next step 512 is to perform interpolated spectral peak frequency shift estimation to determine the residual frequency error. This is done using cubic spline interpolation to increase the precision of the estimate by a factor of 10. This frequency error estimate is then used to correct the frequency of the TD mean for each group 513. Because the preceding operations may have resulted in a small phase shift, a final fine-grain phase adjustment 514 is performed in the TD. The final FD reference data is formed 515 and both the TD and DF references for each phase group are available for spectral cross-correlation based frequency correction. The MATLAB function makePhGrpRef.m teaches how this is mechanized.

Frequency correction using the spectral cross-correlation method 520 is now performed on all frames. The first step is to compute the complex spectral cross-correlation coefficient function between each frame and its corresponding group reference 521. This is done for a specified number of lags, typically 200 for data from a 3 Tesla system, sufficient to accommodate the largest frequency shifts anticipated. Next, the correlation data is evaluated to locate the peak of the real part of the complex correlation function 522. Cubic spline interpolation is employed to increase the precision by a factor of 10 and the interpolated lag of the peak is expressed as a frequency shift in Hz. Next, the frequency shift estimation just determined is used in performing frequency correction on the corresponding TD frame 523. The final step is to form the FD data for each frame in each phase group 524. The MATLAB functions freqAdjSC.m, spectCorr.m, spectCorrInterp.m and cmnFreqAdjTD.m teach how these operations are mechanized.

The final spectrum is formed 530 by combing the qualified frames by group in a manner to avoid introducing phase group cancellation bias due to the frame selection process. The means (averages) of qualified TD frames for each phase group are formed 531 and then the mean of these means 532 is computed. This is the final composite TD data from which the final chemical shift spectrum is formed 533 by applying appropriate apodization and transforming to the FD.

Figure 40A:
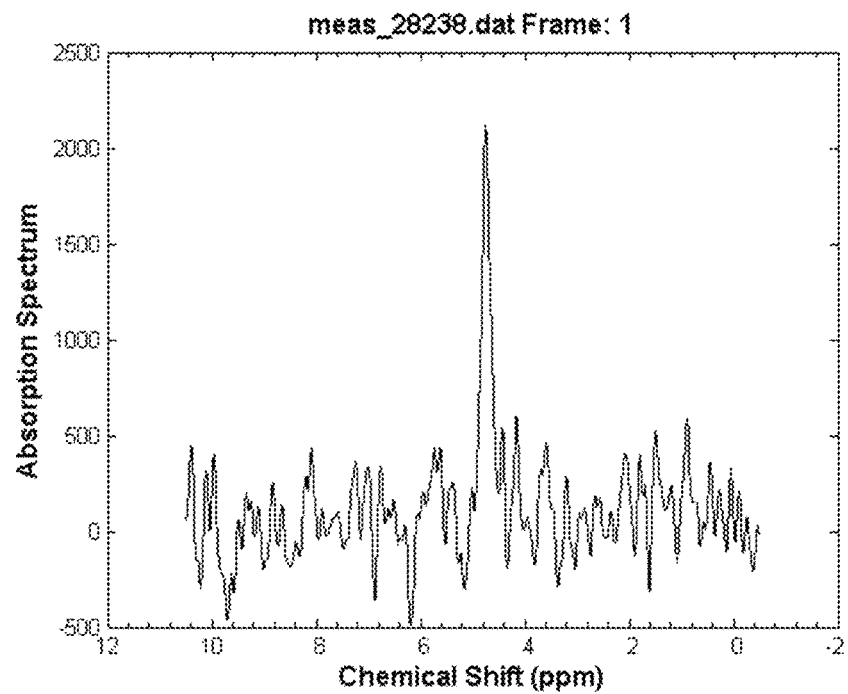
FIG. 40A shows the full spectrum of a single frame from a lumbar MRS disc acquisition.

FIGS. 40A-41D show raw spectral data to illustrate the benefits of advanced post processing to obtain usable results. Only phase correction and apodization have been performed. In the following discussion, 'full spectrum" refers to an extended chemical shift range to include the residual water signal. FIG. 40A shows the extended chemical shift spectrum while "metabolite spectrum" shows an expanded plot of the chemical shift range in which important metabolite signals occur.

Figure 40B:
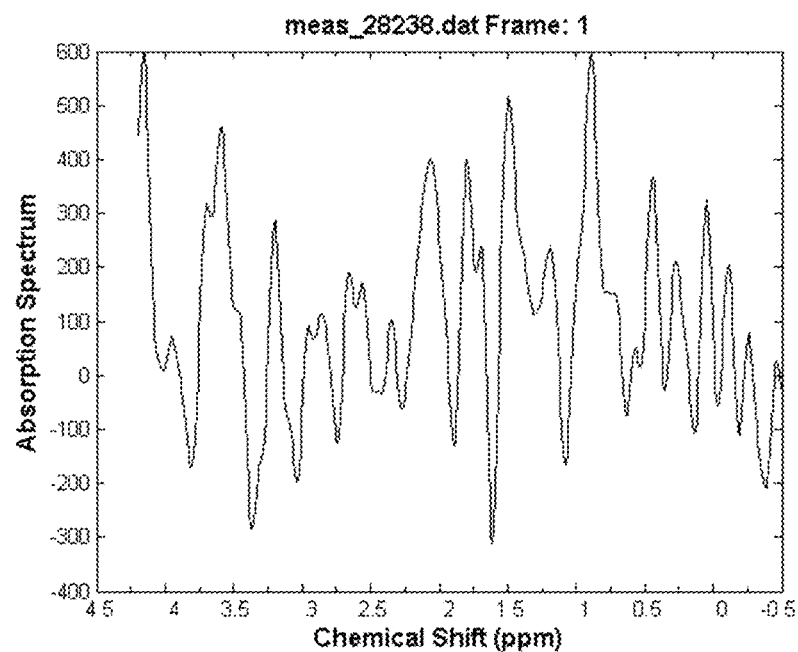
FIG. 40B shows the metabolite range for this same frame shown in FIG. 40A.

FIG. 40A shows the full spectrum of a single frame with an appropriate level of the residual water signal at chemical shift (CS) 4.7. The principal metabolite of interest at CS 2.01 is hardly seen. This represents a generally good quality frame. FIG. 40B shows the metabolite range for this same frame.

Figure 40C:
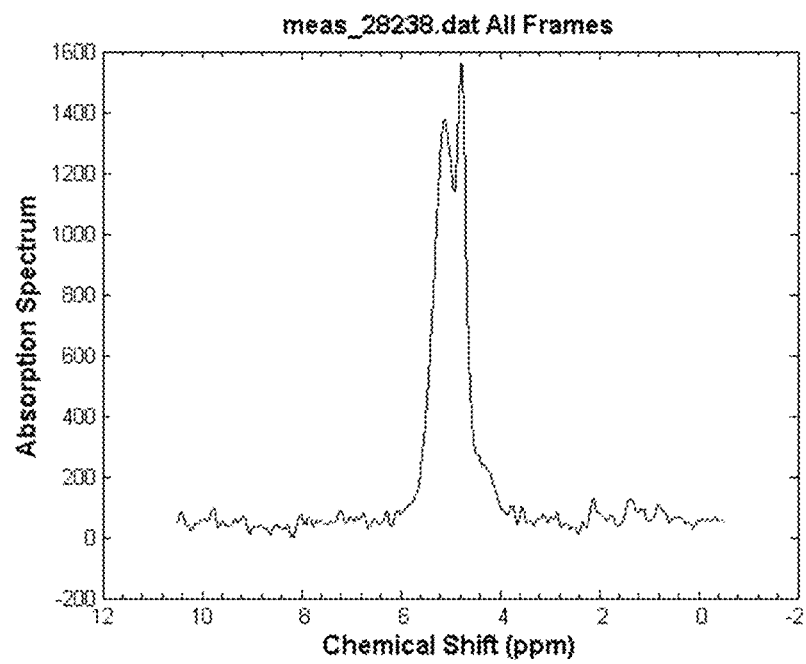
FIG. 40C shows a spectrum representing the average of all 192 frames collected in the series featured in FIGS. 40A-B, and with only very slight phase correction and apodization processing.
Figure 40D:
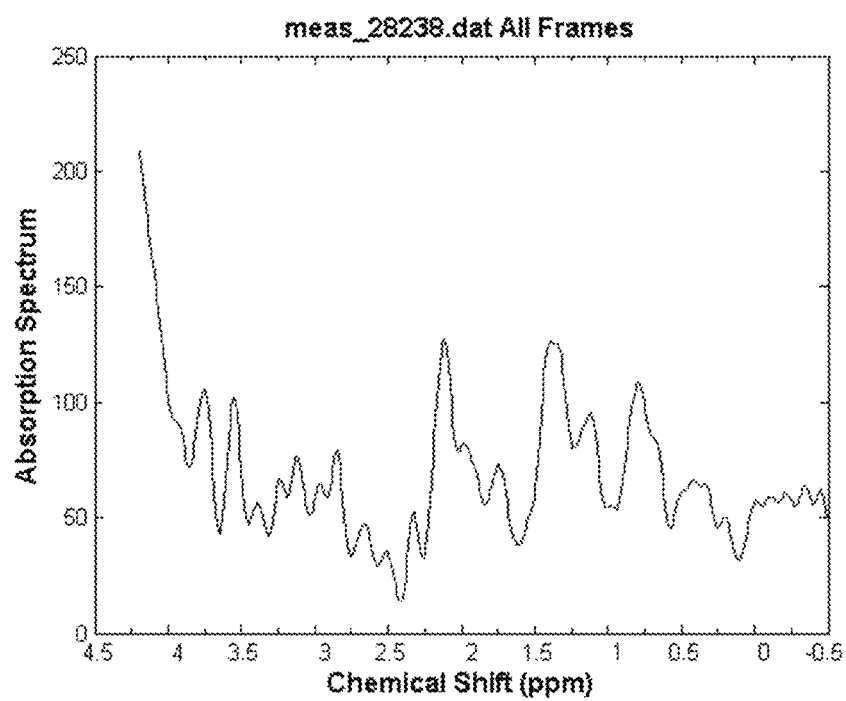
FIG. 40D shows this same spectrum shown in FIG. 40C, but in a zoomed view of a metabolite range of interest.

FIG. 40C shows the average of all 192 frames collected in this series and with only this very slight processing. Although the signal to noise ratio is greatly improved as expected by such averaging, the quality of the signal is greatly degraded by the inclusion of aberrant frames. In the metabolite range plot of the same spectrum shown in FIG. 40D, the metabolite peak which should be at CS 2.01 is broadened and shifted to the left. This degradation reflects the need for frame quality screening to exclude the aberrant frames and frequency correction to align the frequency of the selected frames so they will combine constructively.

X. Baseline Correction

Baseline correction removes variations in the final spectral due to large macromolecules in the acquisition. Various approaches to baseline correction are contemplated as applicable with other embodiments of this disclosure, though they may not be expressly herein shown or described, as would be apparent to one of ordinary skill. One particular beneficial embodiment however is described by reference to the following baseline correction steps.

According to one step, the baseline is estimated using a "ranked order filter" ("ROF") method. According to one further embodiment, the ranked order filter is designed to find the local minimums of the spectra. However, other settings may be used to modify the portions or features of the spectrum tracked by or impacting the ROF results.

According to another step, outliers are removed from the ROF output. The output of the ROF varies slowly and is influenced by large amplitude metabolites. Adjacent points in the output of the ROF with relatively high derivatives indicate large (and abrupt) changes. These will often represent real chemical peak regions, vs. baseline bias artifact. Accordingly, to distinguish baseline offset trends from real target chemical peak offsets from baseline, and thus avoid "correcting" to flatten (and thus artificially reduce or lose) real peak regions to be redrawn along a baseline objective, points bounded by large amplitude metabolites and points with high derivatives are considered outliers and are removed from the ROF output. This allows the next polynomial fit step to track only on "non peak" offsets from a rolling baseline, and thus correct only for the baseline variances while preserving the peaks rising above it. A polynomial is fit to the ROF output without the outliers. A polynomial is fit to the remaining points in the ROF. In another step, the polynomial is used to compute the baseline estimate. The baseline estimate is subtracted from the pre-baseline corrected spectrum to derive the final baseline corrected spectrum.

Figure 41A:
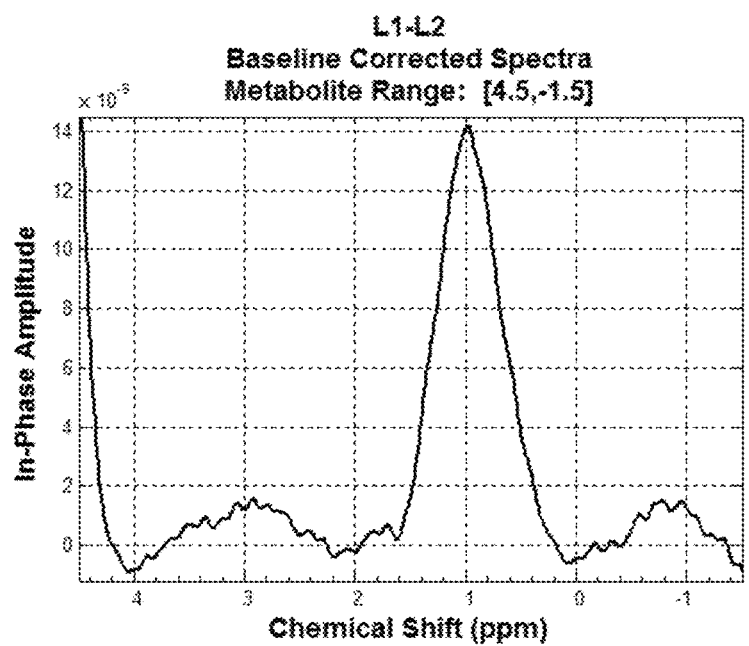
FIG. 41A shows a post-processed spectrum from an MRS acquisition from a lumbar disc, baseline corrected using polynomial fit to an ROF incorporating all spectral data in the range (including outliers).

For further illustration, an example is provided by reference to FIGS. 41A-4D as follows. FIG. 41A shows a post-processed spectrum from an MRS acquisition from a lumbar disc, baseline corrected using polynomial fit to an ROF incorporating all spectral data in the range (including outliers).

Figure 41B:
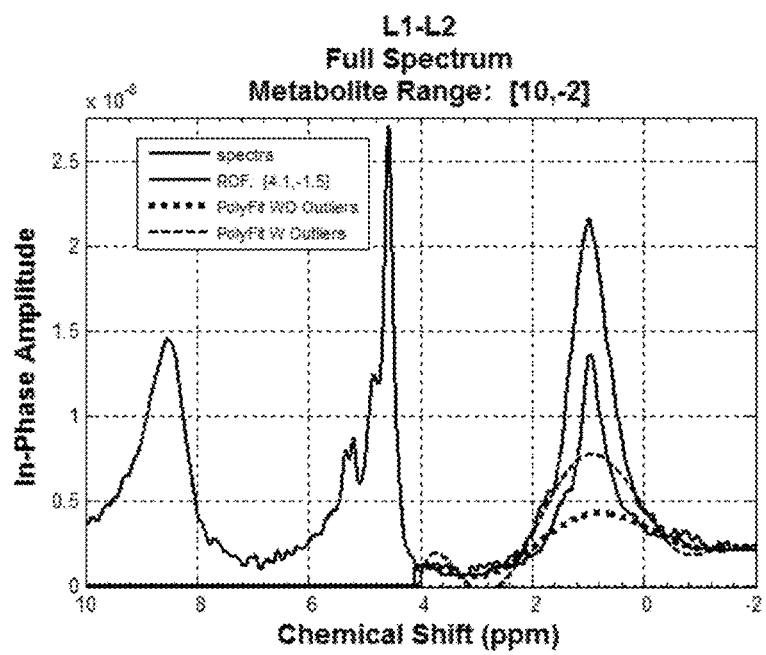
FIG. 41B shows certain baseline correction details overlaid to the spectrum, full spectrum range, for the acquisition featured in FIG. 41A, with the ROF is shown below the spectrum in the metabolite range, the bold dotted line showing polynomial ft to the ROF without outliers, versus the narrower dashed line that shows the polynomial fit with outliers.

FIG. 41B shows certain baseline correction details overlaid to the spectrum, full spectrum range. More specifically, the ROF is shown below the spectrum in the metabolite range. The bold dotted line shows polynomial ft to the ROF without outliers, versus the narrower dashed line that shows the polynomial fit with outliers.

Figure 41C:
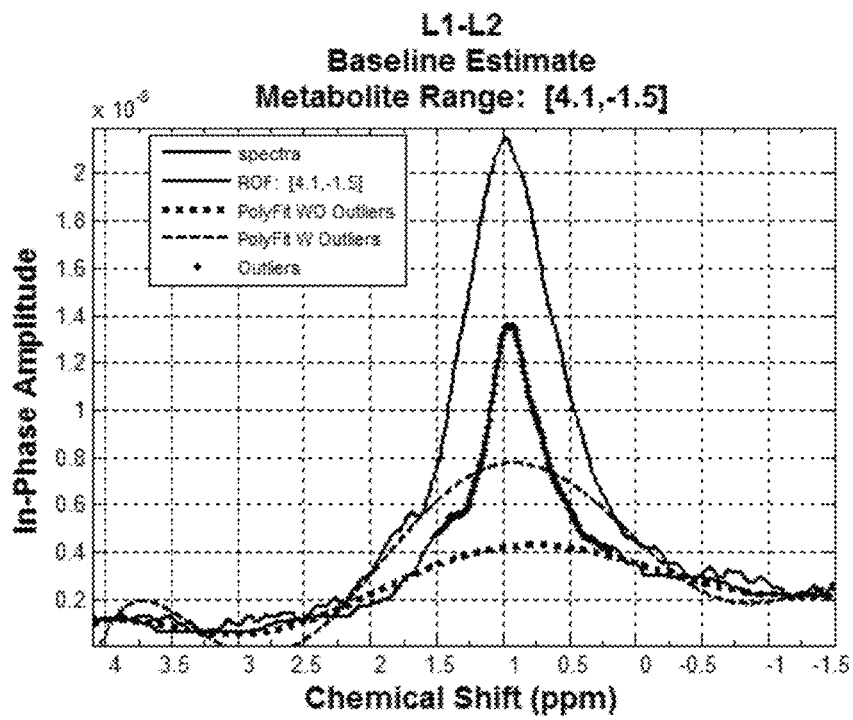
FIG. 41C shows these baseline correction details shown in FIG. 41B, in a zoomed view more narrowly drawn to a metabolite range of interest from the spectrum.

FIG. 41C shows these baseline correction details in a zoomed view more narrowly drawn to a metabolite range of interest from the spectrum.

Figure 41D:
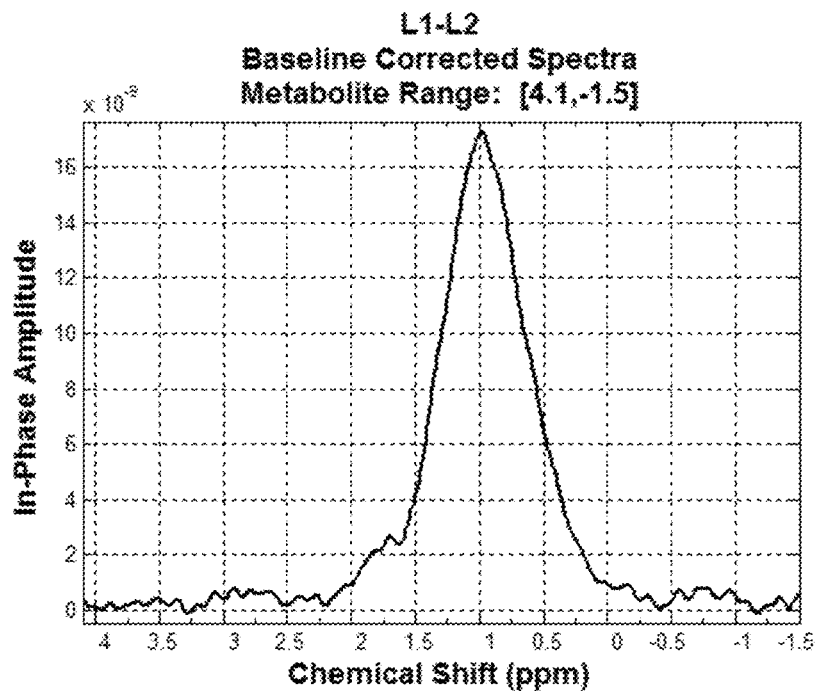
FIG. 41D shows a final spectra post baseline correction using the polyfit without outliers contributing to the ROF used for the fit.

FIG. 41D shows a final spectra post baseline correction using the polyfit without outliers contributing to the ROF used for the fit.

Figure 42A:
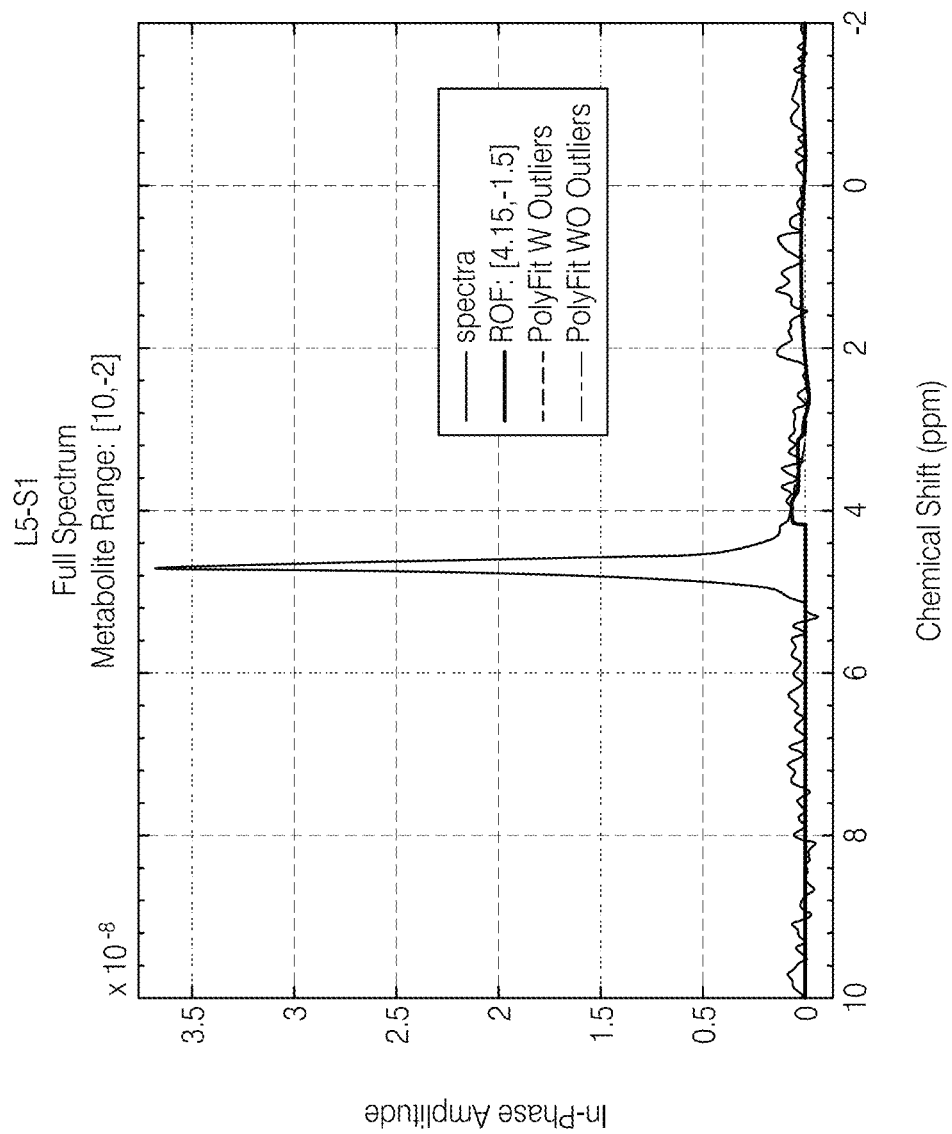
FIG. 42A shows a full range spectrum from an intravertebral disc MRS acquisition, post-processed according to a combination of multiple embodiments of the current disclosure.

Additional examples that illustrate various of the foregoing aspects in various combinations are provided as follows:

FIG. 42A shows a full range spectrum from an intravertebral disc MRS acquisition, post-processed according to a combination of multiple embodiments of the current disclosure.

Figure 42B:
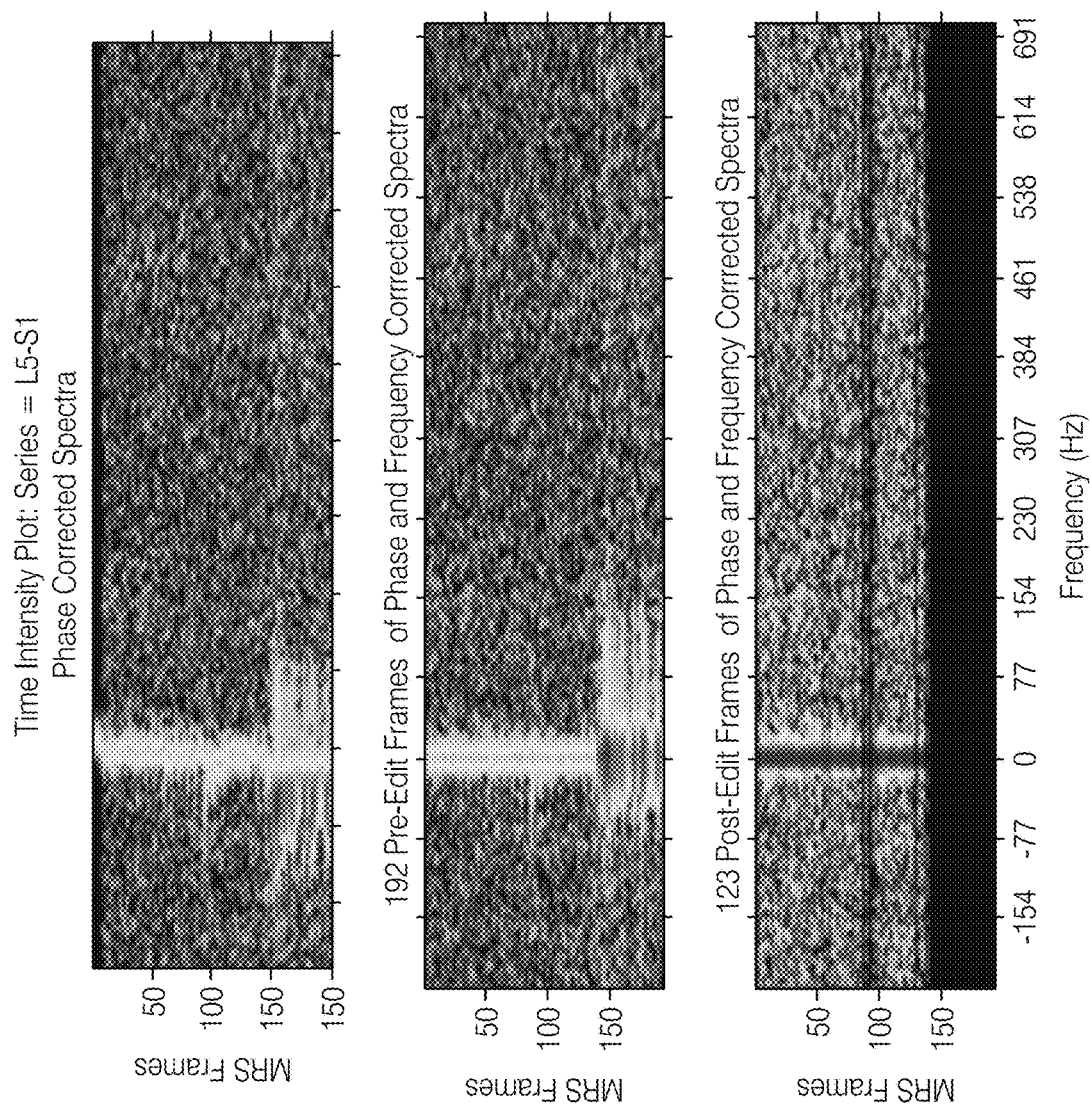
FIG. 42B shows a time-intensity plot of the individual frames along the acquisition series providing the post-processed spectrum shown in FIG. 42A, and shows prior to processing (top), with frame editing (middle), and after frequency correction of the retained qualified frames (bottom)(unqualified screened out frames replaced with dark horizontal lines in the plot).

FIG. 42B shows a time-intensity plot of the individual frames along the acquisition series providing the post-processed spectrum shown in FIG. 42A, and shows prior to processing (top), with frame editing (middle), and after frequency correction of the retained qualified frames (bottom)(unqualified screened out frames replaced with dark horizontal lines in the plot)

Figure 42C:
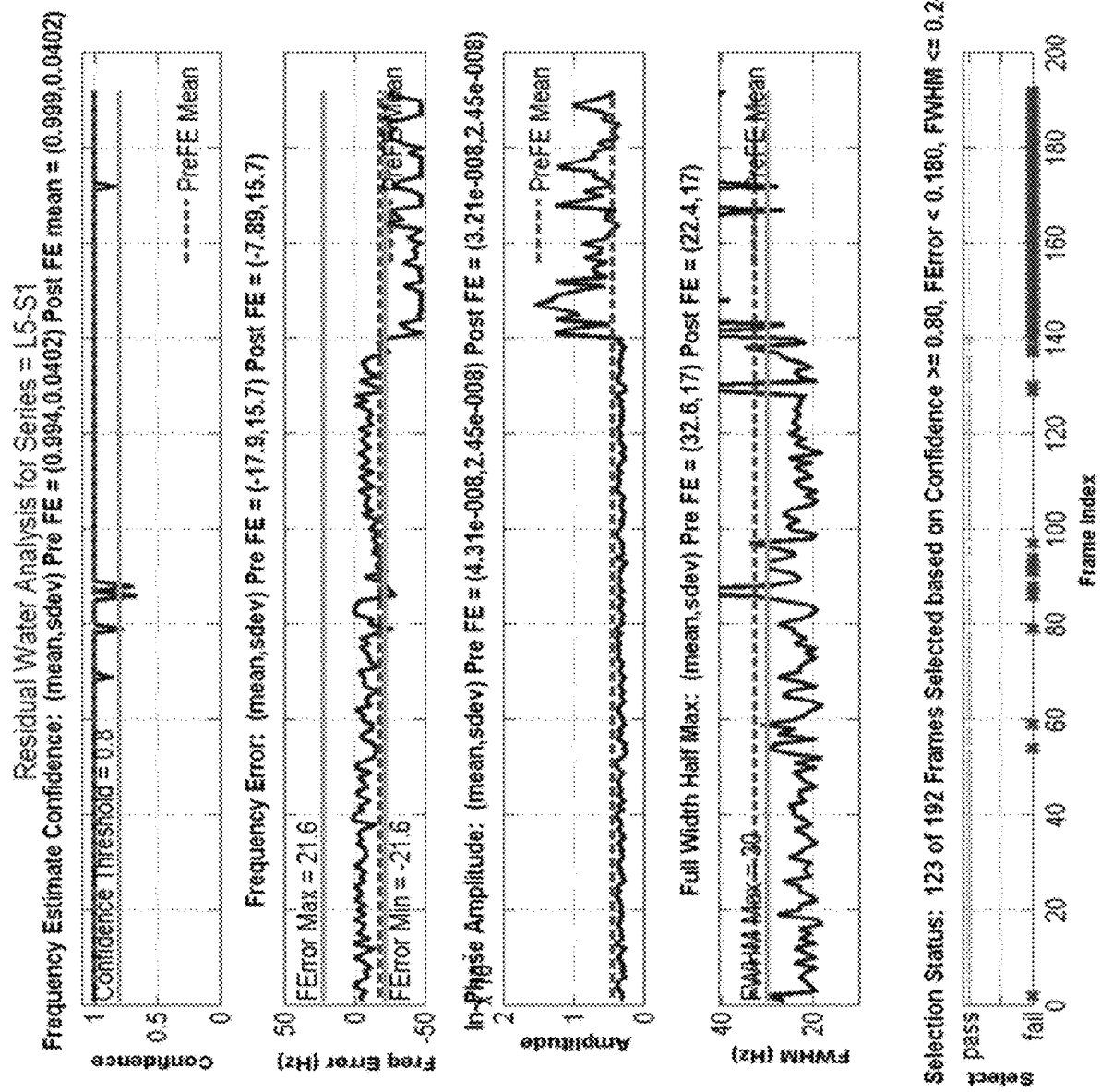
FIG. 42C shows a frame editing panel comprising a series of water signal analyses comprising per-frame plots of "frequency estimate confidence" (confidence of peak location), frequency error, in-phase amplitude, FWHM, and finally qualified retained vs. excluded unqualified (red) frames at bottom.

FIG. 42C shows a frame editing panel comprising a series of water signal analyses comprising per-frame plots of "frequency estimate confidence" (confidence of peak location), frequency error, in-phase amplitude, FWHM, and finally qualified retained vs. excluded unqualified (red) frames at bottom.

Figure 43A:
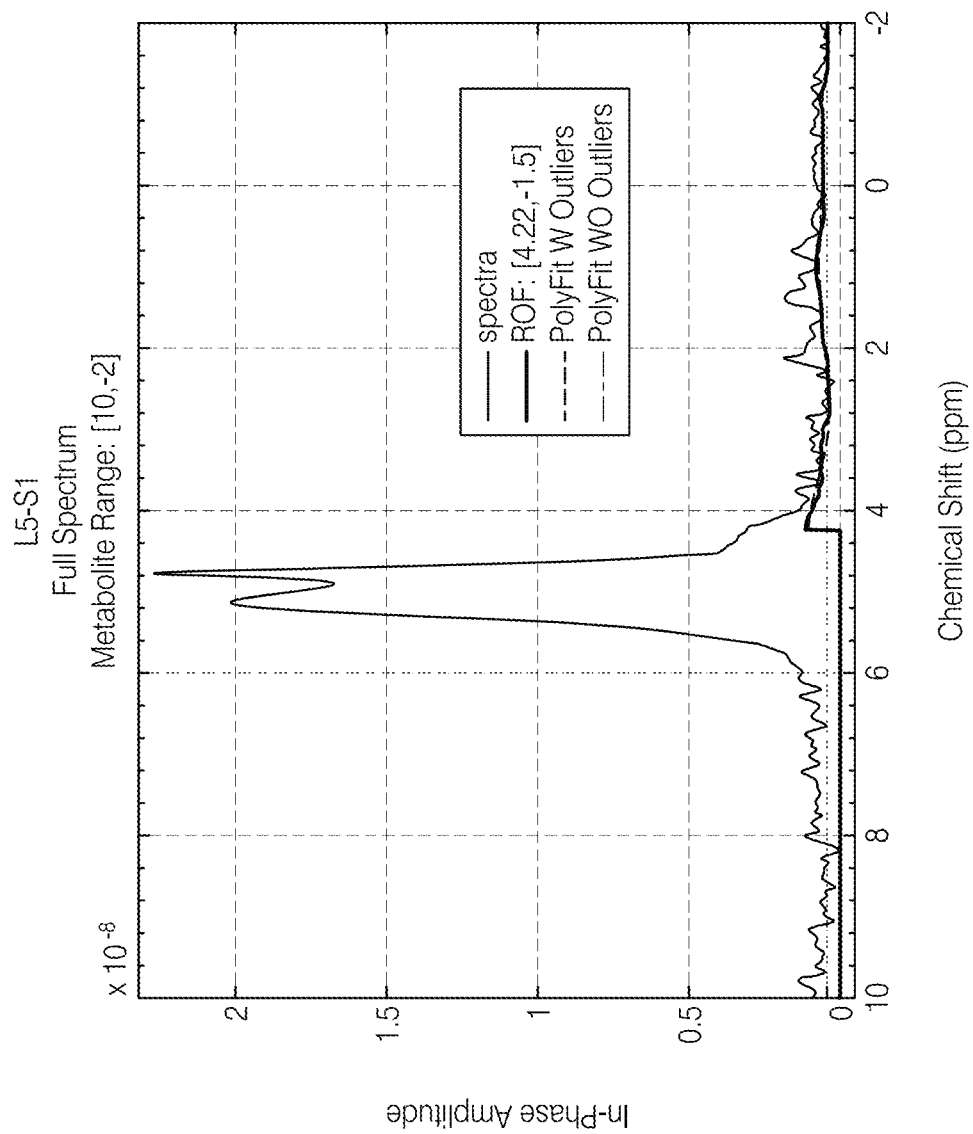
FIG. 43A shows a similar spectral plot for the same acquisition shown in FIG. 42A, but bypassing frequency correction by setting the FWHM threshold criteria below the FWHM of all frames (e.g. excluding them all thus bypasses frame editing and frequency correction all together).

FIG. 43A shows a similar spectral plot for the same acquisition shown in FIG. 42A, but bypassing frequency correction by setting the FWHM threshold criteria below the FWHM of all frames (e.g. excluding them all thus bypasses frame editing and frequency correction all together).

Figure 43B:
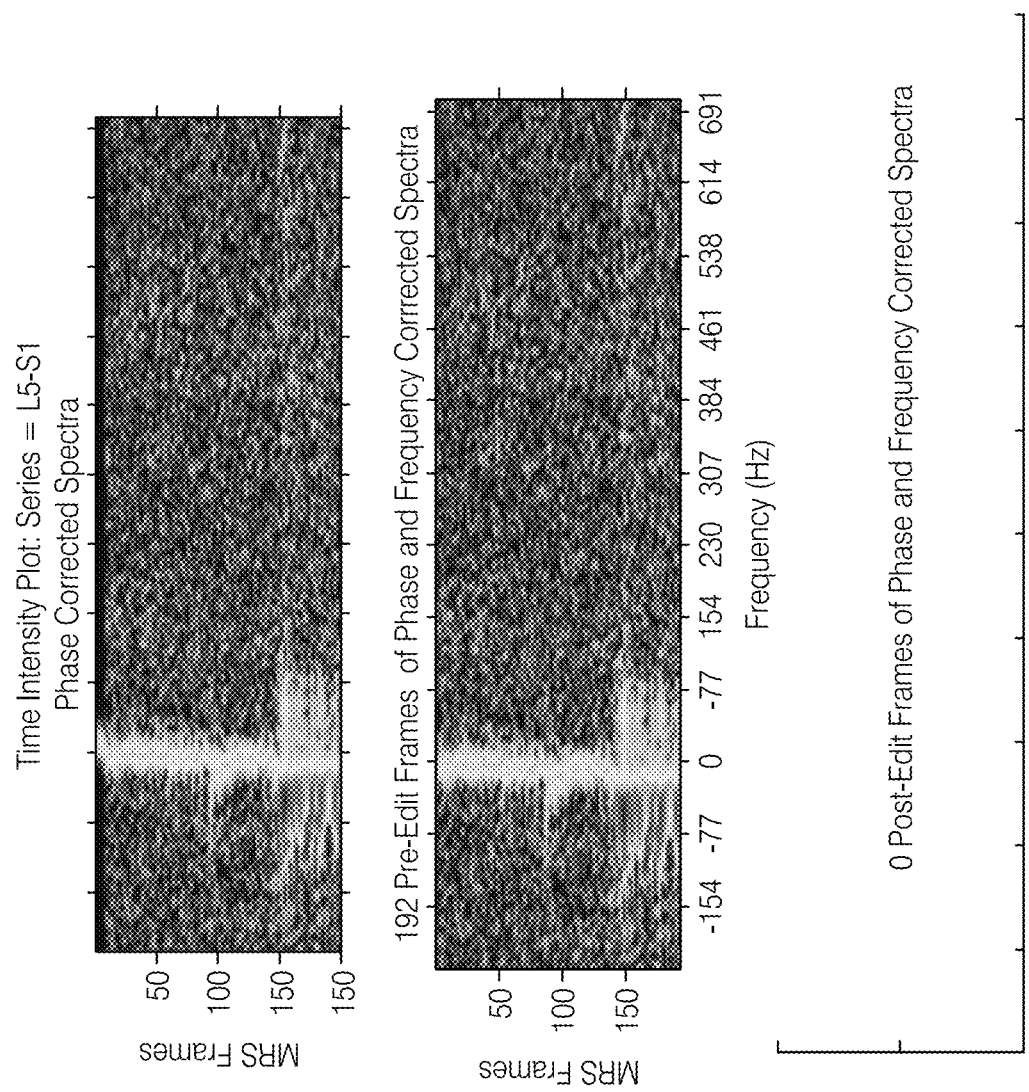
FIG. 43B shows a time intensity plot for the same series of phases of the same acquisition shown in FIG. 43B.

FIG. 43B shows a time intensity plot for the same series of phases of the same acquisition shown in FIG. 43B.

Figure 43C:
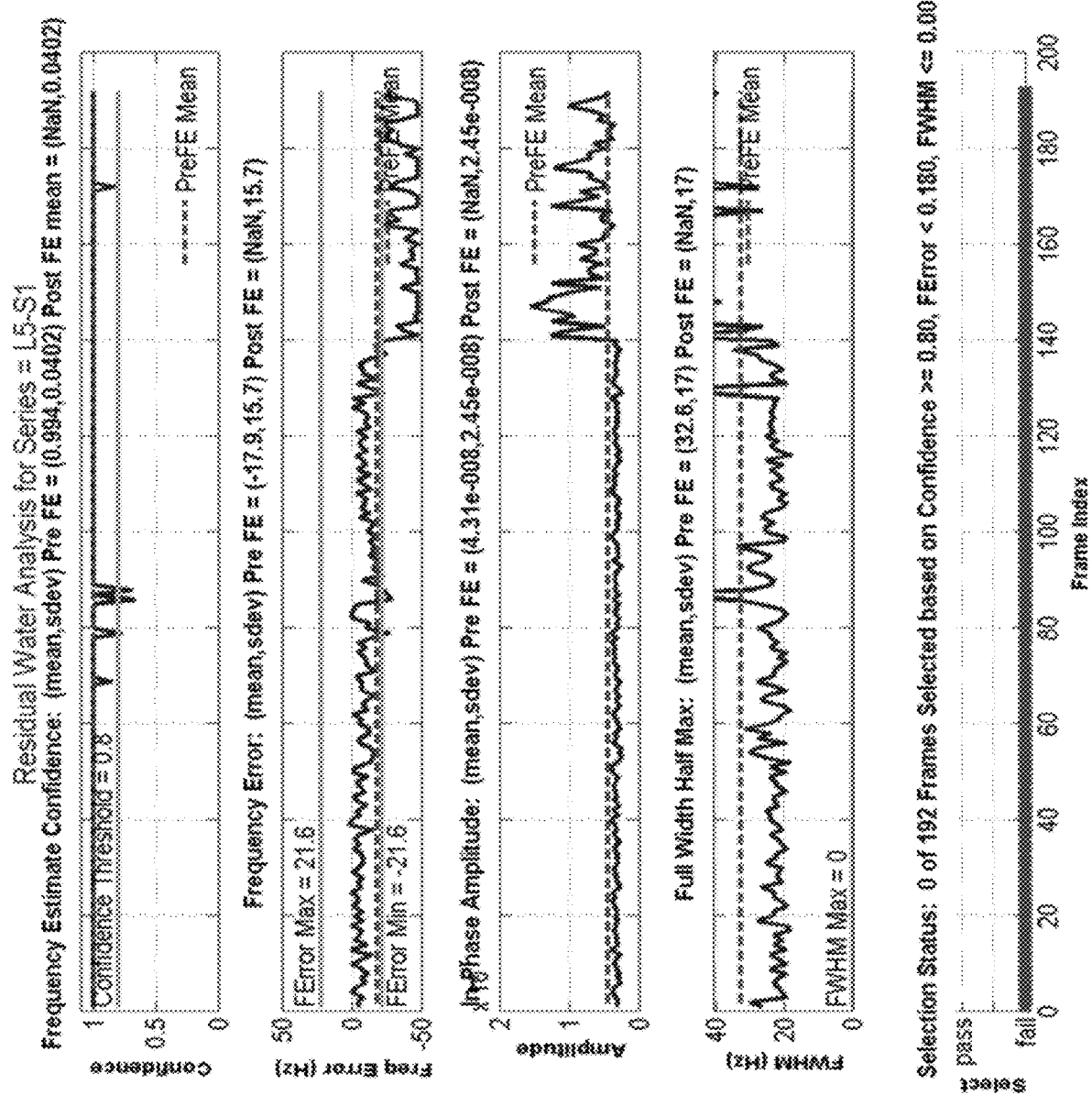

FIG. 43C shows a frame editing panel comprising the water signal analyses similar to that shown in FIG. 42C, and on the same acquisition featured in FIG. 42C, but related to the different frame editing and frequency correction thresholds and related processing featured in FIGS. 43A-B.

While certain embodiments of the disclosure have been described, these embodiments have been presented by way of example only, and are not intended to limit the scope of the broader aspects of the disclosure. Indeed, the novel methods, systems, and devices described herein may be embodied in a variety of other forms. For example, embodiments of one illustrated or described MRS system post-processing component may be combined with embodiments of one or more illustrated or described MRS system processing components. Moreover, the MRS system components described herein, e.g. pulse sequence, signal processor, or diagnostic processor, may be deployed for particular beneficial use for intervertebral discs, or utilized for other purposes. For example, an MRS system (or component sequence, signal processor, or diagnostic processor useful therewith or therein), may be configured and used in manners consistent with one or more broad aspects of this disclosure for diagnosing other tissue environments or conditions than pain within an intervertebral disc. Or, such may be usefully employed for diagnosing pain or other tissue environments or conditions in other regions of interest within the body. Such further applications are considered within the broad scope of disclosure contemplated herein, with or without further modifications, omissions, or additions that may be made by one of ordinary skill for a particular purpose. Furthermore, various omissions, substitutions and changes in the form of the methods, systems, and devices described herein may be made without departing from the spirit of the disclosure. Components and elements may be altered, added, removed, or rearranged. Additionally, processing steps may be altered, added, removed, or reordered. While certain embodiments have been explicitly described, other embodiments will also be apparent to those of ordinary skill in the art based on this disclosure.

In one further embodiment contemplated, a computing system, comprising one or more microprocessors receiving at least one signal responsive to data collected in an MR scanner, is configured to implement a magnetic resonance spectroscopy (MRS) processing system configured to process a repetitive multi-frame MRS spectral acquisition series generated and acquired for a voxel principally located within an intervertebral disc via an MRS pulse sequence, and acquired at multiple parallel acquisition channels of a multi-coil spine detector assembly, in order to provide diagnostic information associated with the disc. According to one still further embodiment, this comprises: an MRS signal processor comprising a channel selector, a phase shift corrector, a frequency shift corrector, a frame editor, and a channel combiner. The system of this embodiment is configured to receive and process the MRS spectral acquisition series for the disc and to generate a processed MRS spectrum for the series with sufficient signal-to-noise ratio (SNR) to acquire information associated with identifiable features along MRS spectral regions associated with unique chemical constituents in the disc. An MRS diagnostic processor is configured to extract data from identifiable chemical regions in the processed MRS spectrum in a manner that provides diagnostic information for diagnosing a medical condition or chemical environment associated with the disc.

In another embodiment, a non-transitory physical computer readable medium encoded with a computer executable computer program or code is operable by a processor to run the computer program or code to cause a computing system to implement a magnetic resonance spectroscopy (MRS) processing system configured to process a repetitive multi-frame MRS spectral acquisition series generated and acquired for a voxel prescribed to correspond with a tissue region of interest in the body of a patient. The computer program or code comprises one or more (in various combinations) of the processing embodiments disclosed hereunder. According to a further embodiment, the voxel is principally located within an intervertebral disc via an MRS pulse sequence, and acquired at multiple parallel acquisition channels of a multi-coil spine detector assembly, in order to provide diagnostic information associated with the disc. According to still another further embodiment, the computer program or code comprises an MRS signal processor that further comprises one or more (in combination) of the following: a channel selector, a phase shift corrector, a frequency shift corrector, a frame editor, and a channel combiner. This is configured to receive and process the MRS spectral acquisition series for the disc and to generate a processed MRS spectrum for the series with sufficient signal-to-noise ratio (SNR) to acquire information associated with identifiable features along MRS spectral regions associated with unique chemical constituents in the disc. An MRS diagnostic processor is provided under still another further embodiment, and is configured to extract data from identifiable chemical regions in the processed MRS spectrum in a manner that provides diagnostic information for diagnosing a medical condition or chemical environment associated with the disc.

In another further embodiment, a magnetic resonance spectroscopy (MRS) processing method is used for processing a repetitive multi-frame MRS spectral acquisition series generated and acquired for a voxel principally located within an intervertebral disc via an MRS pulse sequence, and acquired at multiple acquisition channels of a multi-coil spine detector assembly, and for providing diagnostic information associated with the disc. According to certain further embodiments, the MRS processing method comprises one or more (in combination) of the other processing component embodiments disclosed hereunder. The method according to another particular embodiment comprises: receiving the MRS spectral acquisition series from the multiple acquisition channels; and signal processing the MRS acquisition series. The signal processing component of this method comprises: selecting one or more channels among the multiple channels based upon a predetermined criteria, estimating and correcting phase shift error among multiple frames within the series of a channel acquisition, estimating and correcting a frequency shift error between multiple frames within the series of the channel acquisition, flagging and editing out sub-optimal frames from the series based upon a predetermined criteria frame selection criteria, combining selected and corrected channels for a combined average processed MRS spectrum. Another method embodiment comprises adjusting spectral signal upfield of water signal by subtracting artifact derived from downfield signal components generally mirrored opposite about a water peak center line. Still further method embodiments comprise diagnostically processing the processed MRS spectrum by extracting data from identifiable chemical regions in the processed MRS spectrum and processing the extracted data in a manner that provides MRS-based diagnostic information for diagnosing a medical condition or chemical environment associated with the disc.

It is further contemplated that other processing approaches known in the art may be also combined with the aspects, modes, and embodiments expressly shown and described hereunder, such as for example eddy current correction, other apodization techniques etc. Moreover, other types of MRS acquisitions, such as multi-voxel for example, may be used. Still further, the processors and related methods disclosed may be embedded into the controller or processing environments of the MR systems themselves used in the acquisitions, or may be stored, operated, and conducted remotely. For example, such may be stored and/or operated via a separate server, either co-located or remote from the MR acquisition system, such as via data received electronically via the internet, PACS, FTP uploading, or tangible physical media such as mobile hard drives or CDs/DVDs. It is further contemplated that notebook computers, PDAs, mobile phones, etc. may also provide at least in part the processing, communicating, and/or display functions according to the present aspects, modes, and embodiments of this disclosure.

TABLE 1

Range of Optimization Thresholds.

| Parameter | Range of Values | Number of Values |
| --- | --- | --- |
| Confidence Threshold | 0.5:0.1:0.7 | 3 |
| FWHM Threshold | 0.15:0.05:0.35 | 5 |
| Frequency Error | 0.15:0.05:0.30 | 4 |

What is claimed is:

1. A method for processing a set of multiple serially acquired magnetic resonance spectroscopy (MRS) free induction decay (FID) frames from a multi-frame MRS acquisition series from a region of interest (ROI) in a subject, and for providing a post-processed MRS spectrum, comprising:
receiving the set of multiple serially acquired MRS FID frames from the multi-frame MRS acquisition series from the ROI in a subject;
associating first and second groups of FID frames within the set with first and second different relative phases, respectively, of a phase step cycle along the MRS acquisition series;
processing the first and second groups separately;
averaging the first and second groups separately to form first and second average interim spectra; and
averaging the first and second average interim spectra to provide the post-processed MRS spectrum.

2. The method of claim 1, further comprising performing at least one of phase shift correction, frame editing, and frequency shift correction separately for the first and second groups.

3. The method of claim 1, further comprising:
performing the method on a number equal to N groups of FID frames, the FID frames comprising similar phasing within each group but different than in other groups;
processing each of the N groups separately;
averaging the FID frames separately within each group;
averaging the group averages together; and
wherein N equals an integer more than two.

4. The method of claim 1, wherein:
the MRS acquisition series comprises a number F of FID frames;
the different relative phases comprise a unique number S of phase steps; and
F divided by S equals N, which comprises a whole number.

5. A method performed according claim 1 using a processor, wherein the method further comprises controlling the processor to perform said method using a computer program stored in a non-transitory computer readable medium.

6. The method of claim 1, wherein the ROI comprises a portion of a musculoskeletal joint.

7. The method of claim 6, wherein the joint comprises a skeletal joint.

8. The method of claim 7, wherein the skeletal joint comprises a spinal joint.

9. The method of claim 8, wherein the ROI comprises at least a portion of an intervertebral disc.

10. A method performed according to claim 1, wherein:
said MRS acquisition series is acquired from a single voxel positioned within the ROI according to a single voxel spectroscopy pulse sequence.

11. A method performed according to claim 1, wherein said MRS acquisition comprises a multi-voxel spectroscopy acquisition comprising multiple said MRS acquisition series corresponding to each said voxel, and performing the method on each said MRS acquisition series.

12. A method for processing a set of multiple serially acquired magnetic resonance spectroscopy (MRS) free induction decay (FID) frames from a multi-frame MRS acquisition series from a region of interest (ROI) in a subject, and for providing a post-processed MRS spectrum, comprising:
receiving the set of multiple serially acquired MRS FID frames from the multi-frame MRS acquisition series from the ROI in a subject;
partially post-processing the set of FID frames to produce an interim MRS spectrum;
generating a first baseline estimate using a rank order filter (ROF) on a range of interest of the interim MRS spectrum partially post-processed from the set;
fitting a polynomial to at least a portion of the first baseline estimate to generate a baseline curve; and
subtracting the baseline curve from the interim MRS spectrum to provide the post-processed MRS spectrum.

13. The method of claim 12, further comprising:
determining first and second regions of the first baseline estimate to be included and excluded, respectively, for the polynomial fit; and
fitting the polynomial to only the first regions of the baseline estimate.

14. A method performed according claim 12 using a processor, the method further comprising controlling the processor to perform said method using a computer program stored in a non-transitory computer readable medium.

15. The method of claim 12, wherein:
the ROI comprises a portion of a musculoskeletal joint.

16. The method of claim 15, wherein the joint comprises a skeletal joint.

17. The method of claim 16, wherein the skeletal joint comprises a spinal joint.

18. The method of claim 17, wherein the ROI comprises at least a portion of an intervertebral disc.

19. A method performed according to claim 12, wherein:
said MRS acquisition series is acquired from a single voxel positioned within the ROI according to a single voxel spectroscopy pulse sequence.

20. A method performed according to claim 12, wherein said MRS acquisition comprises a multi-voxel spectroscopy acquisition comprising multiple said MRS acquisition series corresponding to each said voxel, and performing the method on each said MRS acquisition series.

* * * * *